US012343540B2

(12) United States Patent
Netoff et al.

(10) Patent No.: US 12,343,540 B2
(45) Date of Patent: Jul. 1, 2025

(54) HIERARCHICAL OPTIMIZATION OF NEUROMODULATOR SETTINGS

(71) Applicant: Regents of the University of Minnesota, Minneapolis, MN (US)

(72) Inventors: Theoden I. Netoff, Minneapolis, MN (US); Andrew Lamperski, Minneapolis, MN (US); David Darrow, Minneapolis, MN (US); Tyler Lekang, Minneapolis, MN (US); Zixi Zhao, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 319 days.

(21) Appl. No.: 17/835,608

(22) Filed: Jun. 8, 2022

(65) Prior Publication Data
US 2022/0387800 A1    Dec. 8, 2022

Related U.S. Application Data

(60) Provisional application No. 63/208,375, filed on Jun. 8, 2021.

(51) Int. Cl.
*A61N 1/36*     (2006.01)
*A61N 1/372*    (2006.01)
(52) U.S. Cl.
CPC ..... *A61N 1/36132* (2013.01); *A61N 1/37241* (2013.01)

(58) Field of Classification Search
None
See application file for complete search history.

(56) References Cited

U.S. PATENT DOCUMENTS

2005/0060008 A1*  3/2005  Goetz ............... A61N 1/36071
                                                    607/48
2020/0391037 A1   12/2020 Grado et al.

OTHER PUBLICATIONS

Banjević, D., & Kim, M. J. (2019). Thompson sampling for stochastic control: The continuous parameter case. IEEE Transactions on Automatic Control, 64(10), 4137-4152.

Brochu, E., Cora, V. M., & De Freitas, N. (2010). A tutorial on Bayesian optimization of expensive cost functions, with application to active user modeling and hierarchical reinforcement learning. arXiv preprint arXiv:1012.2599; 1-49.

(Continued)

*Primary Examiner* — Ankit D Tejani
(74) *Attorney, Agent, or Firm* — QUARLES & BRADY LLP

(57) ABSTRACT

User-specific neurostimulation settings are efficiently determined and optimized based on an optimized set of population-based neurostimulation settings. The population data are clustered and a set of test settings for a new user are selected as settings that efficiently discriminate between the clusters. User preference of the test settings are used to map the user to a particular cluster of settings, which can be used to determine user-specific neurostimulation settings. The user-based settings can be iteratively updated and/or optimized using information from the population data, such as by using average preference score surfaces in the population data to identify and/or filter new test settings for the user.

19 Claims, 41 Drawing Sheets

(56) References Cited

OTHER PUBLICATIONS

Bubeck, S., Eldan, R., & Lehec, J. (2018). Sampling from a log-concave distribution with projected Langevin Monte Carlo. Discrete & Computational Geometry, 59, 757-783.

Chau, N. H., Moulines, E., Rásonyi, M., Sabanis, S., & Zhang, Y. (2021). On stochastic gradient langevin dynamics with dependent data streams: The fully nonconvex case. SIAM Journal on Mathematics of Data Science, 3(3), 959-986.

Dalalyan, A. S. (2017). Theoretical guarantees for approximate sampling from smooth and log-concave densities. Journal of the Royal Statistical Society Series B: Statistical Methodology, 79(3), 651-676.

Durmus, Alain, and Eric Moulines. "Nonasymptotic convergence analysis for the unadjusted Langevin algorithm." (2017): 1551-1587.

Grado L. L., et al. Bayesian adaptive dual control of deep brain stimulation in a computational model of Parkinson's disease. PLOS Comput Biol. Dec. 6, 2018;14(12): e1006606. doi: 10.1371/journal.pcbi. 1006606. PMID: 30521519; PMCID: PMC6298687; 1-23.

Kim, M. J. (2017). Thompson sampling for stochastic control: The finite parameter case. IEEE Transactions on Automatic Control, 62(12), 6415-6422.

Raginsky, M., Rakhlin, A., & Telgarsky, M. (2017, June). Non-convex learning via stochastic gradient langevin dynamics: a nonasymptotic analysis. In Conference on Learning Theory (pp. 1674-1703). PMLR.

Shahriari, Bobak, et al. "Taking the human out of the loop: A review of Bayesian optimization." Proceedings of the IEEE 104.1 (2015): 148-175.

Srinivas, N. (2010). Gaussian process optimization in the bandit setting: No. regret and experimental design, in Proceedings of the 27th International Conference on International Conference on Machine Learning, Omnipress, pp. 1015-1022.

* cited by examiner

|  | Cluster 1 | Cluster 2 | Cluster 3 |
|---|---|---|---|
| Patient 1 | <u>0.48</u> | -0.4 | -0.5 |
| Patient 2 | <u>0.81</u> | -0.15 | -0.58 |
| Patient 3 | <u>0.61</u> | -0.43 | -0.43 |
| Patient 4 | 0.31 | <u>0.65</u> | 0.41 |
| Patient 5 | 0.55 | <u>0.77</u> | 0.42 |
| Patient 6 | 0.15 | <u>0.71</u> | 0.55 |
| Patient 7 | -0.45 | 0.62 | <u>0.71</u> |
| Patient 8 | -0.071 | 0.16 | <u>0.67</u> |
| Patient 9 | -0.21 | 0.66 | <u>0.71</u> |

FIG. 14

HIERARCHICAL OPTIMIZATION OF NEUROMODULATOR SETTINGS

BACKGROUND

Neurostimulators are devices that can be implanted in patients for a variety of conditions. The devices deliver mild electrical signals, typically along the spine or in the brain (e.g., in the epidural space of a patient's back, in the neck region of a patient adjacent the Vagus nerve, deep in the brain, etc.), which may provide relief from pain, tremors, epilepsy, other effects from Parkinson's, spinal cord injury, etc. The mild electrical signals delivered by such neurostimulators may be adjusted in various standard ways, including frequency, pulse width, signal amplitude, and stimulation pattern. Different conditions and different patients may be best treated by different patterns of neurostimulation.

SUMMARY OF THE DISCLOSURE

The present disclosure addresses the aforementioned drawbacks by providing a method for generating neurostimulation control settings for controlling a neurostimulation system. The method includes receiving, by a controller of the neurostimulation system, population-based optimized neurostimulation settings. A plurality of clusters of neurostimulation settings is extracted from the population-based optimized neurostimulation settings, and a set of test settings that efficiently discriminate between the plurality of clusters is determined therefrom. The set of test settings is presented to a user via the controller, and user preference data indicative of the user's preference for settings within the set of test settings is received by the controller. User-based neurostimulation settings are determined using the controller to map the user to one of the clusters in the plurality of clusters based on the user preference data. The determined user-based neurostimulation settings are then stored (e.g., on the neurostimulation system and/or remote to the neurostimulation system), and can be used to control operation of the neurostimulation system.

It is another aspect of the present disclosure to provide a method for controlling a neurostimulation system. The method includes accessing, via a controller of the neurostimulation system, population-based optimized neurostimulation settings. For each patient represented in the population-based optimized neurostimulation settings, a set of surface-characterizing data points that characterize a preference score surface for each patient is extracted. A plurality of clusters of neurostimulation settings is then extracted from the population-based optimized neurostimulation settings using the set of surface-characterizing data points for each patient. An average surface for each of the plurality of clusters is generated, where each average surface corresponds to a surface that fits the surface-characterizing data points within each respective cluster. A set of test settings that efficiently discriminate between the plurality of clusters is determined. The set of test settings is presented to a user via the controller and user preference data indicative of the user's preference for settings within the set of test settings is received by the controller. User-based neurostimulation settings are determined using the controller to map the user to one of the clusters in the plurality of clusters based on the user preference data. The user-based neurostimulation settings are iteratively updated, where the average surface associated with the one of the clusters in the plurality of clusters is used to identify and/or filter new test settings in each iteration. The neurostimulation system is then controlled, via the controller, using the updated user-based neurostimulation settings.

The foregoing and other aspects and advantages of the present disclosure will appear from the following description. In the description, reference is made to the accompanying drawings that form a part hereof, and in which there is shown by way of illustration one or more embodiments. These embodiments do not necessarily represent the full scope of the invention, however, and reference is therefore made to the claims and herein for interpreting the scope of the invention.

BRIEF DESCRIPTION OF THE DRAWINGS

FIG. 14 depicts use of Pearson correlation coefficients to map example patients into clusters.

DETAILED DESCRIPTION

Figure 1:
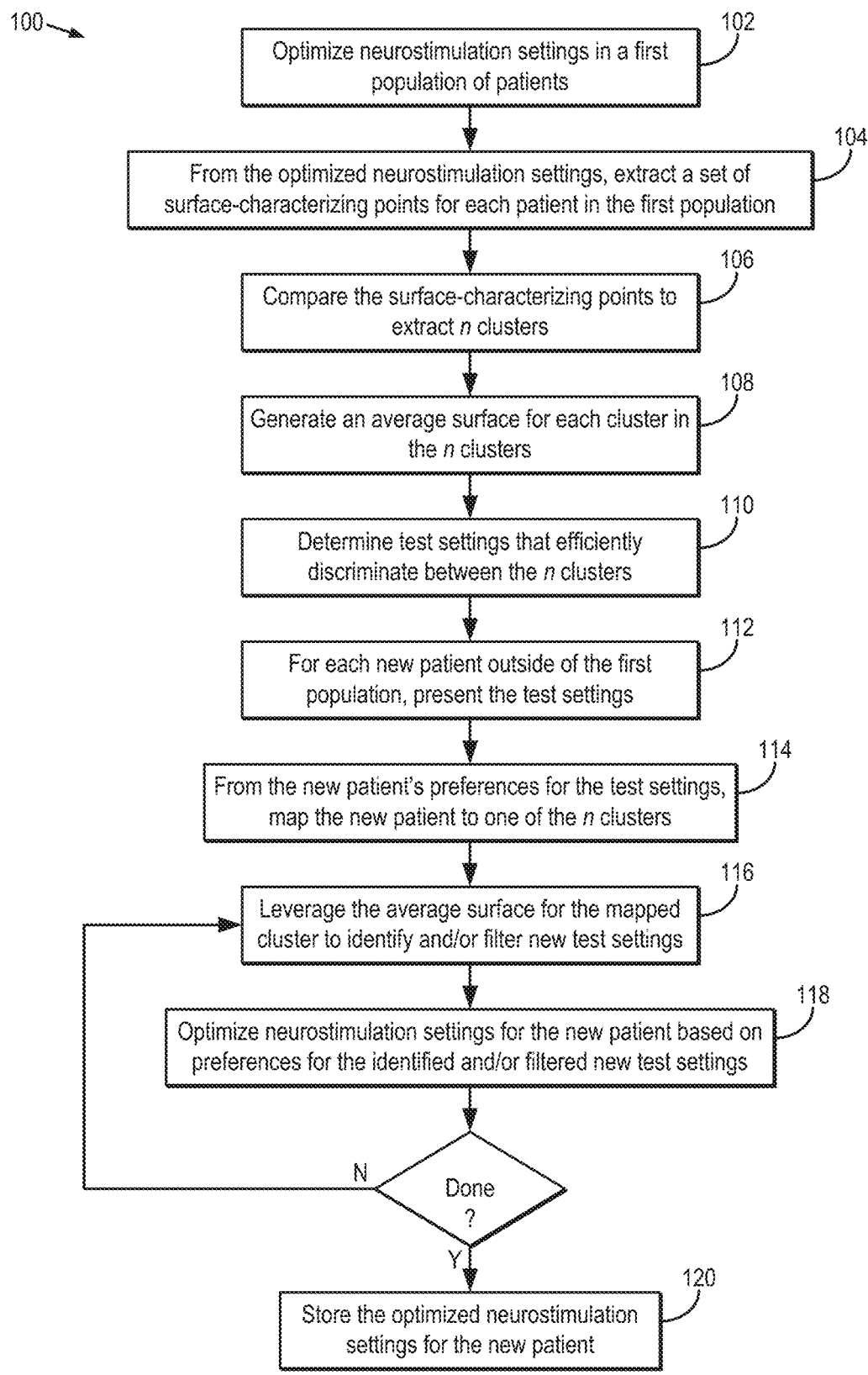
FIG. 1 depicts an example process for optimizing neurostimulation settings.

Specific patients typically have unique experiences with conditions, even conditions that are common to large patient populations. For example, within a large group of patients suffering from chronic pain, each patient within the group may have his or her own set of responses that differ from other patients within the group and that may be influenced by, for example, family history, personal health history, injury, psychological outlook, external support structure, sensitivity to environmental factors, etc. Thus, "personalized medicine," or the tailoring of medical treatment to individual characteristics of specific patients has become an aspiration within the medical community. Described herein are methods and approaches for delivering personalized medicine in a manner that leverages population-level detail and insight, in a manner that delivers therapy to patients faster than would otherwise be possible.

Notwithstanding the fact that specific patients typically have unique experiences with conditions, patients within a large group often fall into categories within the larger group, where patients within each category respond in ways that are similar to each other. In the larger group of, for example, chronic pain patients who experience some level of relief through neurostimulation, different individual patients may experience relief from chronic pain through very different neurostimulation programs. For example, one patient may experience relief from a tonic stimulation pattern (e.g., a consistent stream of pulses), at a set frequency, pulse width and amplitude; another patient may experience relief from a tonic stimulation pattern at a different frequency, pulse width and amplitude; yet another patient may experience relief from a burst pattern of stimulation (e.g., a group of pulses that may have a lower amplitude and/or higher frequency than a typical tonic stimulation pattern); and still other patients may experience relief from another specific pattern or patterns of stimulation.

Relief from chronic pain is described herein as one example condition that may be treated with neurostimulation. Other conditions may benefit from neurostimulation and from the methods and processes outlined herein—such as, for example, spinal cord injury (pain, paralysis), movement disorders, autonomic functions (e.g., blood pressure regulation, bowel function, bladder function, sexual function, temperature regulation), epilepsy, Parkinson's Disease, neuromyopathy, etc.

Finding the specific patterns and parameters that are effective in treating any specific individual patient can be time-consuming. A process of methodical optimization may be required, but such a process can be very time-consuming, and few tools may be available to guide the process. Often, a trial-and-error approach may be employed by clinicians and technicians who may have developed some level of intuition, but who lack a robust toolset or physiological understanding of many of the factors affecting specific patients. For some patients, the optimization process presents an insurmountable barrier to relief that may in fact be possible for the patient. The optimization process may be insurmountable for at least two different reasons.

Patients who do not already have an implanted neurostimulator are typically given a "trial" version for one or two weeks prior to permanent implantation (that is, trial leads are percutaneously implanted, but the neurostimulator portion—the electrical device that generates the signals that are drive to the leads—is not initially implanted); in order to receive a permanent device (e.g., per regulatory and/or insurance coverage requirements), these patients often must experience a significant benefit (e.g., 50% reduction in pain). However, if the settings for the trial device are not appropriately selected for that specific patient, the patient may not experience sufficient relief to justify a permanent implant. For such patients, the trial may end after about two weeks with the trial leads being explanted, with no further possibility for that patient to receive relief from an implanted neurostimulator. This may be the case, even if such an implanted neurostimulator might ultimately benefit the patient. That is, for this class of patients, relief is not experienced quickly enough within a trial period of a typical implant process, even though many patients within the class might ultimately benefit.

A second group of patients may also not get past the optimization process for an entirely different reason. Optimizing neurostimulator settings can take time—in part because it takes time for the therapeutic effect to be perceived. That is, it may take several days for some patients to perceive effective neurostimulation (e.g., because of how the brain processes and perceives pain). Thus, to fully test out various settings may require many days between settings. To facilitate comparison of multiple settings may take even more time, particularly if certain settings must be tested multiple times to confirm effectiveness, rule out any placebo effects, rule out psychosomatic or psychological effects, etc. Some patients have a difficult time, psychologically, handling such an optimization process. That is, the barrier may be psychological (for example, related to a lack of hope, or a short runway during which hope must be experienced, or an issue with stamina and an inability to keep trying different settings without experiencing significant improvement). For these patients, even those who could ultimately benefit from neurostimulation, a maximum, potentially life-changing therapeutic benefit may never be reached.

For at least these aforementioned potential barriers to realizing therapeutic benefit, any method for accelerating the process of optimizing neurostimulation holds great promise. Demonstrating potential relief during a typically narrow trial-period window, prior to permanent implantation of a neurostimulator may provide more patients with potential relief; and optimizing faster for patients with a lower inherent stamina or sense of hope may provide such patients with greater relief.

Described herein are systems and methods for accelerating the optimization of neurostimulation. FIG. 1 depicts one example method 100. As depicted, the method 100 includes optimizing neurostimulation in a first population of patients, as indicated at step 102. In some implementations, optimizing the first population of patients includes optimizing the neurostimulation using a Bayesian optimization process, whereby individual settings are presented to the patients, and the patients make and rank pairs of settings (e.g., by choosing a winner for each pair of settings compared). Such an approach is described in co-application Ser. No. 16/966,390, filed on Jul. 30, 2020, titled "Method for Adaptive Control of a Medical Device Using Bayesian Optimization," and published as US 2020/0391037—the entire contents of which are herein incorporated by reference. Additionally or alternatively, a previously generated set of such population-based optimized neurostimulation settings can be received or otherwise accessed by the controller of the neurostimulation system.

The method 100 further includes deriving, from the population-based optimized neurostimulation settings and/or parameters, a set of surface-characterizing points for each patient in first population, as indicated at step 104. As described below in more detail, the set of surface-characterizing points generally characterize a preference score surface for each patient represented in the population associated with the population-based optimized neurostimulation settings.

The method 100 further includes comparing the surface-characterizing points to extract n clusters, as indicated at step 106. As described below in more detail, the surface-characterizing points can be compared using a number of different possible techniques, including comparisons based on one or more distance metrics. The method 100 further includes deriving an average surface for each cluster in the n clusters, as indicated at step 108. In general, an average surface represents a surface that best fits the surface-characterizing points associated with a cluster.

Test settings that efficiently discriminate between the n clusters are determined, as indicated at step 110. The method 100 further includes presenting determined test settings to each new patient outside of the first population, as indicated at step 112. The method 100 further includes mapping each new patient to one of then clusters, based on that new patient's preferences for the test settings, as indicated at step 114.

The average surface for the mapped cluster can be leveraged to identify and/or filter new test settings, as indicated at step 116. The method 100 further includes updating or otherwise optimizing the patient based on the patient's preferences for the identified/filtered new test settings, as indicated at step 118. The process of leveraging the average surface of the mapped cluster to identify and/or filter test settings and optimizing neurostimulation for the patient based on the patient's preferences for the identified and/or filtered new test settings can then be repeated (e.g., iteratively repeated). In some implementations, this process of leveraging and identifying and optimizing proceeds much more quickly than another method of optimization would without use of average surfaces derived from n clusters. In such implementations, specific patients may benefit from hierarchical or population-based modeling—specifically, by, for example, either successfully navigating through a trial-period implantation, or by experiencing a rapid convergence on therapeutic settings.

After the neurostimulation settings and/or parameters for the patient are optimized, those user-based neurostimulation settings are stored for further use by the neurostimulation device, as indicated at step 120. For instance, the user-based neurostimulation settings and/or parameters can be stored in a memory or other data storage device local to the neurostimulation device. In some other instances, the settings and/or parameters can be stored remotely (e.g., on a server, on a mobile device) and can be transmitted or otherwise communicated (e.g., via a wired communication, via wireless communication) to the neurostimulation device.

An example process for optimizing neurostimulation settings and/or parameters in a first population of patients, which may be implemented in step 102 of FIG. 1, is now described. FIGS. 2A-10K depict a process for optimizing neurostimulation settings for nine example patients—"Patient 11" (FIGS. 2A-2K), "Patient 12" (FIGS. 3A-3K), "Patient 13" (FIGS. 4A-4K), "Patient 21" (FIGS. 5A-5K), "Patient 22" (FIGS. 6A-6K), "Patient 23" (FIGS. 7A-7K), "Patient 31" (FIGS. 8A-8K), "Patient 32" (FIGS. 9A-9K), and "Patient 33" (FIGS. 10A-10K).

FIGS. 2A-2K depict a process for optimizing neurostimulation settings for a first example patient ("Patient 11"). As depicted in the right portion of each figure, a standard "grid" of test settings are presented to the patient. In the right portion of each of FIGS. 2A-2K, these initial settings appear as '+' symbols, and in the implementation shown, they correspond to the following pulse-width/frequency pairs: {(100 uS, 150 Hz), (300 uS, 150 Hz), (600 uS, 150 Hz), (100 uS, 500 Hz), (300 uS, 500 Hz), (600 uS, 500 Hz), (100 uS, 1000 Hz), (300 uS, 1000 Hz), (600 uS, 1000 Hz)}. In this implementation, these pulse-width/frequency pairs are selected for demonstration purposes, to provide a relatively uniform grid; and patient preference data is synthesized based on a model that includes a stochastic noise element. The reader will appreciate other pulse-width/frequency pairs could be selected.

These pulse-width/frequency pairs of stimulation settings (each pulse-width/frequency pair a "setting") can be presented to a patient in pair-wise fashion, such that the patient can express a preference for one setting over another in a binary fashion. This process of receiving binary preferences from the patient over many different settings can be repeated until comparisons have been made and corresponding preferences received for each pair of settings within a set of settings. For example, within a set of five settings (A, B, C, D, E), the following pairs may be compared, and preferences received for the same: {A-B, A-C, A-D, A-E, B-C, B-D, B-E, C-D, C-E, D-E}.

Based on the preferences received, a mathematical surface can be generated, for example, using a probit function.

Gaussian process regression ("GPR") is a stochastic method that operates within finite boundaries of an infinite space. A GPR may include a prior distribution based on the set of observed sample points, θ, and a posterior (also called predictive) distribution that predicts the outcome for all possible parameter settings θ*; both can be used to generate a regression mean and standard deviation at each possible parameter set in the finite space. The prior distribution can be over the objective function f(θ) and can be generated by incorporating prior knowledge or beliefs from the sampled parameter space. Prior information of the space includes the mean, m(θ), and covariance function, K(θ, θ*):

$$f(\theta) \sim GP(m(\theta), K(\theta, \theta^*)) \tag{1}$$

The mean is often initialized to zero everywhere, an appropriate assumption given the hypothesis that motor symptom severity does not depend on stimulation parameters. The covariance function estimates the correlation between settings in the parameter space, enforcing a smoothness controlled by a length constant λ.

The posterior distribution updates the prior distribution using sample points from the parameter space. Given θ, θ*, and sample outcomes y, the mean and variance at each possible parameter set can be calculated as:

$$\mu^* = K(\theta^*, \theta)[K(\theta, \theta) + \eta^2 I]^{-1} y \tag{2}$$

$$\sigma^2 = K(\theta^*, \theta^*) - K(\theta^*, \theta)[K(\theta, \theta) + \eta^2 I]^{-1} K(\theta^*, \theta) + \eta^2 I \tag{3}$$

where K is the same covariance function used to calculate the prior distribution, I is the identity matrix, μ* is the mean of each possible parameter set, and $\eta^2$ is the estimated measurement noise variance. The GPR can be used for functions that intelligently select sample points to improve the regression fit.

Bayesian optimization can be used for intelligent sampling of the parameter space and uses an acquisition function to determine the best setting to sample next. The acquisition function is calculated from the GPR and can guide sampling to the predicted minimum, to where the uncertainty is the highest, or both. One can implement the Expected Improvement with exploration ("EI+") acquisition function.

Expected Improvement ("EI") calculates the expected value between the current lowest estimate, $f_{min}$, and the estimated mean fit given all possible parameter sets, μ*:

$$EI(\theta) = E(\max(f_{min} - \mu^*)) \tag{4}$$

The parameter setting with the largest expected improvement value is sampled next. A problem with EI is that over-exploiting and sampling near the current best minimum can occur. A solution is to include an exploration condition which encourages exploration of the parameter space. To determine if an area is over-exploited, the standard deviation at the next sample point is compared to the estimate of the measurement noise amplitude η multiplied by a value between 0-1, α. If the standard deviation at the next sample point is less than a the length constant of the kernel, λ, is increased to smooth the fit and the sample is estimated again to encourage exploration:

$$\sigma < \alpha^* \eta \tag{5}$$

An optimization algorithm can only be as good as the measure which it attempts to optimize. In the above, an attempt to optimize for a specific parameters is described, which may not tell the whole story. In attempting to optimize one parameter, the goal may not be only to reduce a particular undesirable effect, but also to minimize side effects, and to otherwise improve the overall quality of life for the patient. These can be difficult quantities to measure, and thus to optimize for. Additionally, even if both effects and side effects can be accurately measured, in order to optimize, a function, $f(r, s)$, which took both the effect and side effect scores and combined them into a single, scalar value would need to be chosen. In the simplest model, $f(r, s)$ may be a linear combination of r, s such that $f(r, s)=\alpha s+(1-\alpha)s$, which still leaves the task of determining the appropriate relative weight α, which is likely different for each patient.

Instead, the problem can be reformulated in an attempt to directly optimize for the desired outcome: patient preference. Optimizing for patient preference is not an easy task. Asking patients to provide ratings on a numerical scale is difficult, often inaccurate, and subject to numerous cognitive biases. However, humans do excel at comparing options and expressing preference for one over others, and in applications requiring human judgment, preferences are often more accurate than numerical ratings.

In order to use binary preference data, the GPR can be reformulated into a probit Gaussian process regressor ("pGPR"). Instead of being able to directly sample the objective function, it can be inferred from a set of binary observations. As a non-limiting example, the data can now be a set of ranked pairs, $D_{1:m} = \{\vec{a}_i \succ \vec{b}_i\}_{i=1}^m$, where $\succ$ indicates that a patient prefers setting $\vec{a}$ to setting $\vec{b}$. The n distinct elements in the training data can be denoted as $\vec{x}_{i:n}$, where $\vec{a}_i$ and $\vec{b}_i$ are two elements of $\vec{x}_{i:n}$.

The value function, v(•) for any setting can be modeled as v(•)=f(•)+ε, where ε∼$\mathcal{N}$(0, σ²) is normally distributed noise. The value function describes the value a patient derives from a given setting, with the noise term modeling uncertainty in the preferences. The challenge here is to learn $\vec{f}$, where $\vec{f} = \{f(\vec{x}_i)\}_{i=1}^n$ is the value of the objective function at the training points.

The binary observations can be related back to the latent objective function using binomial-probit regression, as an example. Under this model, the probability that item $\vec{a}$ is preferred to $\vec{b}$ is given by:

$$P(\vec{a}_i \succ \vec{b}_i | f(\vec{a}_i), f(\vec{b}_i)) = P(v(\vec{a}_i) > v(\vec{b}_i) | f(\vec{a}_i), f(\vec{b}_i)) \tag{6}$$
$$= P(f(\vec{a}_i) - f(\vec{b}_i) > \varepsilon_b - \varepsilon_a)$$
$$= \Phi\left(\frac{f(\vec{a}_i) - f(\vec{b}_i)}{\sqrt{2}\sigma}\right)$$

where Φ(•) is the CDF of the standard normal distribution. That is to say that the probability that $\vec{a}$ is preferred to $\vec{b}$ is proportional to the difference between $f(\vec{a})$ and $f(\vec{b})$, divided by the magnitude of the noise, σ.

Now, the posterior distribution of the latent objective function can be estimated. The goal is to find the distribution of the objective function that maximizes the posterior probability of the binary observations, known as the maximum a posteriori ("MAP") estimate. As a non-limiting example, Newton-Raphson recursion can be used to learn $\vec{f}_{MAP}$:

$$\vec{f}_{MAP} = \arg\max_{\vec{f}} P(\vec{f}|D) \propto P(\vec{f}) \prod_{i=1}^m P(\vec{a}_i \succ \vec{b}_i | f(\vec{a}_i), f(\vec{b}_i)). \tag{7}$$

Figure 16:
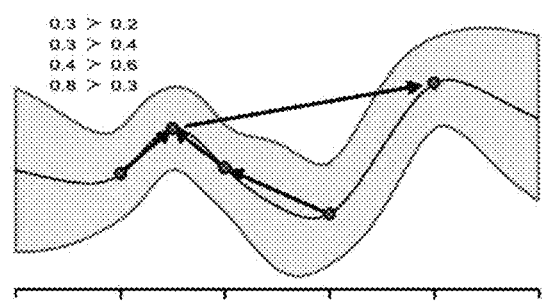
FIG. 16 depicts an example of the probit model applied to preference data.

After computing the model of the objective function, $f_{MAP}$, the acquisition function can be computed and sampling can proceed as described above. FIG. 16 shows an example of the probit procedure used to model a 1D function from a series of preferences. Specifically, FIG. 16 depicts an example of the probit model inferring a GP from a set of preference data. The preference data is shown in the top left, with corresponding arrows.

Returning to FIG. 2A and the subsequent figures, the surface on the left represents a two-dimensional probability surface that has been generated by application of a probit function to the preferences received previously from the patient, with respect to the settings presented to the patient. This two-dimensional probability surface represents a calculated probability (preference score) that specific pulse-width/frequency regions will be therapeutic to a patient. The surface evolves over time, as more preference data is captured from the patient, as depicted in FIGS. 2B-2K for "Patient 11."

A Bayesian optimization process can be applied to an existing data set (e.g., settings tested so far, and corresponding preference data received) to identify a next set of test settings to be used in converging on a true region (e.g., pulse-width/frequency of neurostimulation settings) of therapeutic benefit. The next set of test settings identified by the Bayesian optimization are depicted as an 'x' on the right side of each figure; and these next set of test settings are presented to the patient in the following month. That is, with respect to FIG. 2A, the '+' data settings represent the initial settings tested by "Patient 11" in the first month of testing; and the 'x' data settings represent the next settings to be tested (in month two), as predicted by the Bayesian optimization process.

The Bayesian optimization process can be configured to favor or disfavor specific data settings. In many implementations, a balance will be struck between exploiting regions that are close to high preference scores and exploring regions of the parameter space (e.g., frequency/pulse-width space) that have not been explored previously or sufficiently. A greater focus on exploration may ultimately result in higher-accuracy predictions/identifications of regions of greatest therapeutic benefit in the parameter space, but such a focus may extend the time required for a patient to evaluate settings, and such a focus may force the patient to evaluate many settings that do not provide greatest therapeutic benefit. For many patients, both may be undesirable—testing settings that do not have a high likelihood of providing therapeutic benefit, just to rule out portions of the parameter space; or prolonging the optimization process in order to test a large number of exploratory data settings. Accordingly, it can be advantageous to carefully balance exploration versus exploitation of the parameter space.

In each of the FIGS. 2A-2K (and subsequent figure sets for other example patients), the shading on the right side of the figure corresponds to the calculated probability (preference score); that is, a high preference score corresponds to lighter shading (and a greater surface height on the left portion of the figure), and a lower preference score corresponds to a darker shading (and a lower surface height on the left portion of the figure).

Figure 2A:
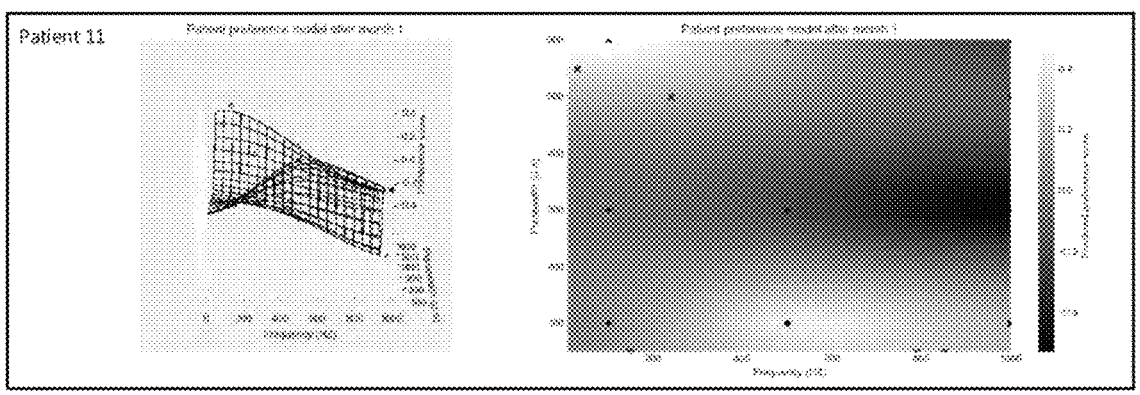
FIGS. 2A-2K depict a process for optimizing neurostimulation settings for a first example patient.
Figure 2B:
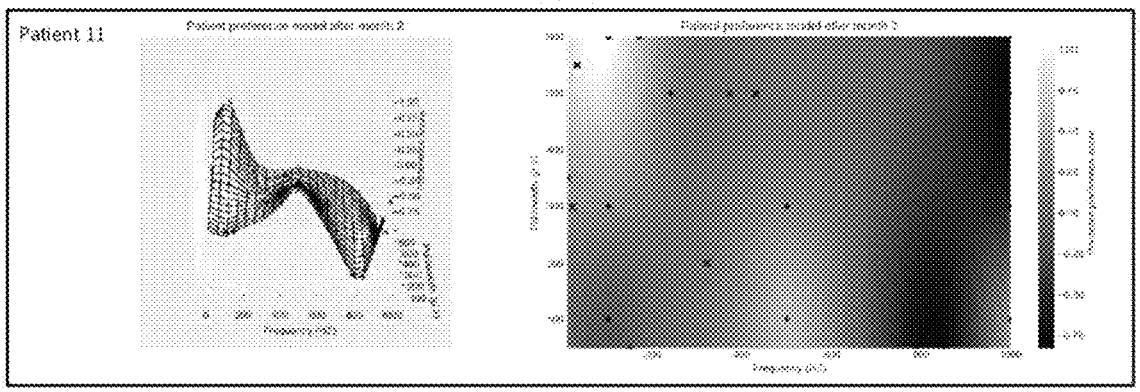
Figure 2C:
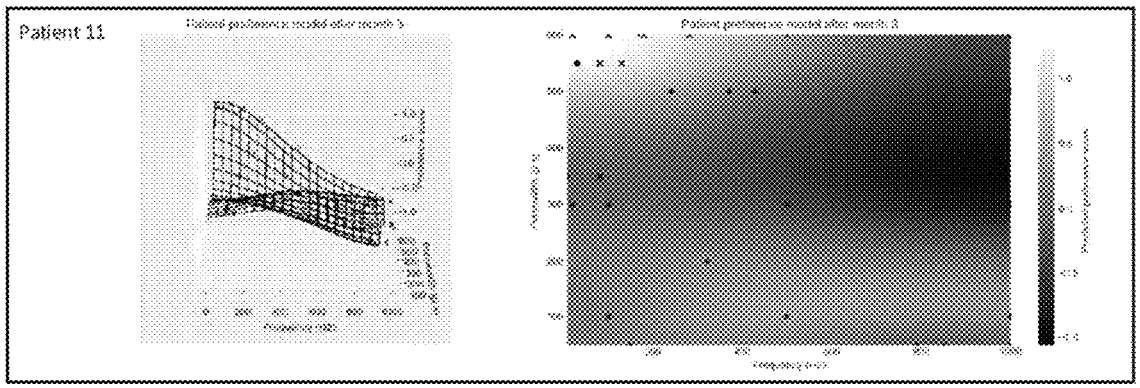

FIG. 2B depicts the cumulative testing after month two—the 'x' data settings from month one become '+' data settings in month two; and additional 'x' test settings are identified by the Bayesian optimization process, for testing in month three, which is depicted in FIG. 2C. In each successive month, the surface on the left and the corresponding grayscale "heat map" on the right are updated to reflect simulated responses by the patient.

Figure 2D:
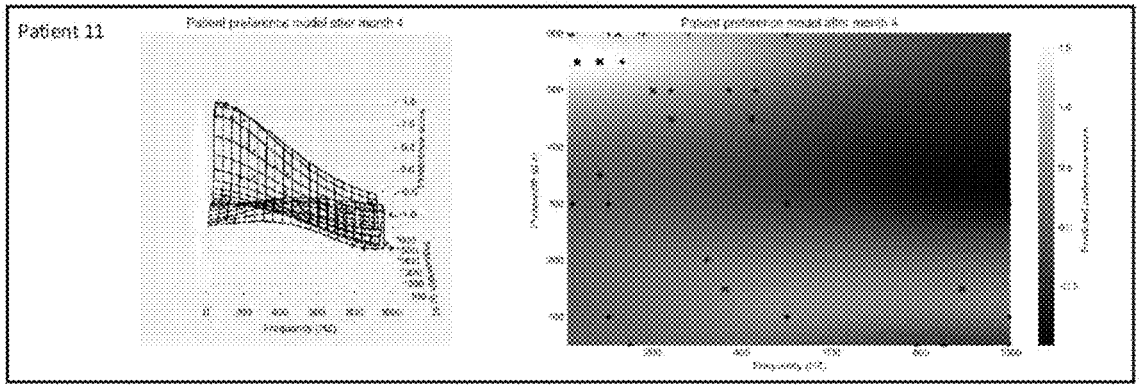
Figure 2E:
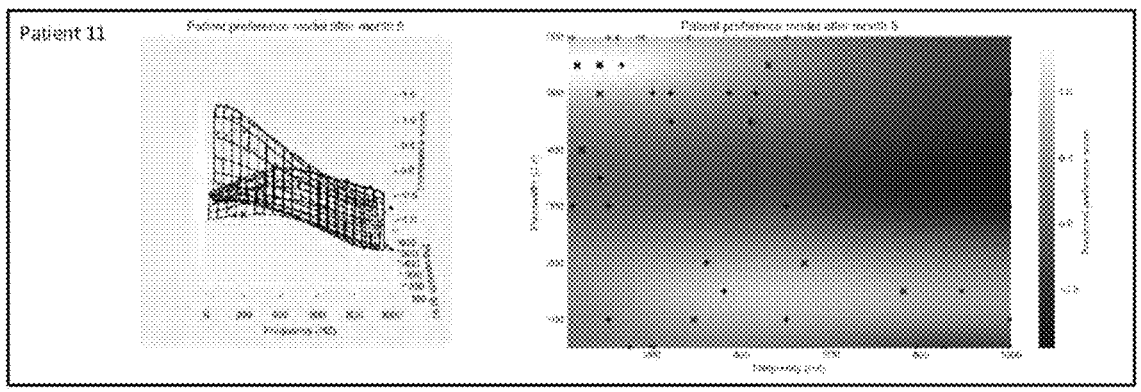
Figure 2F:
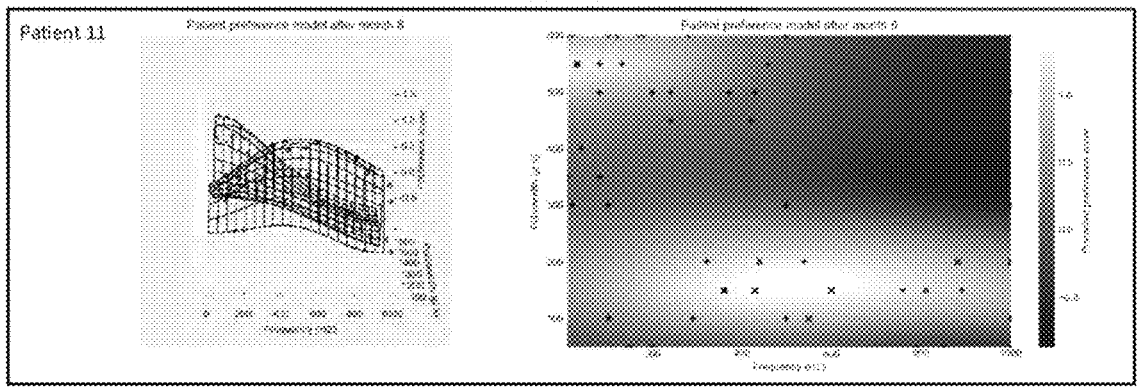
Figure 2G:
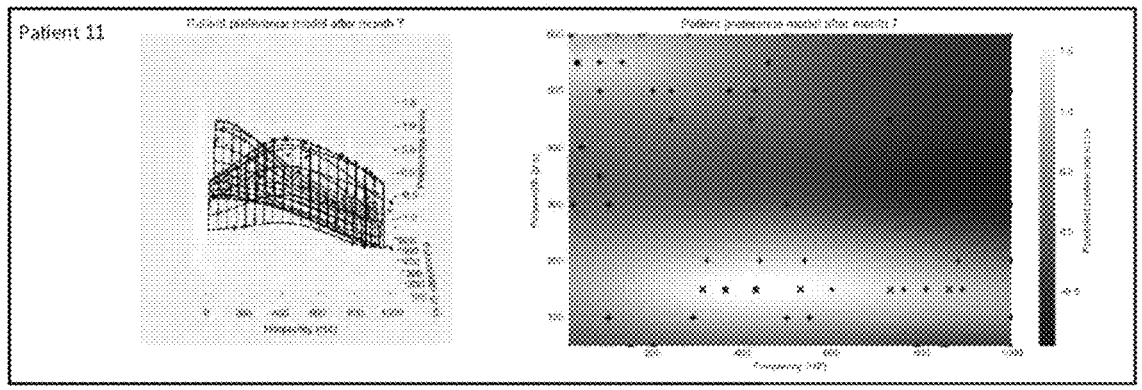
Figure 2H:
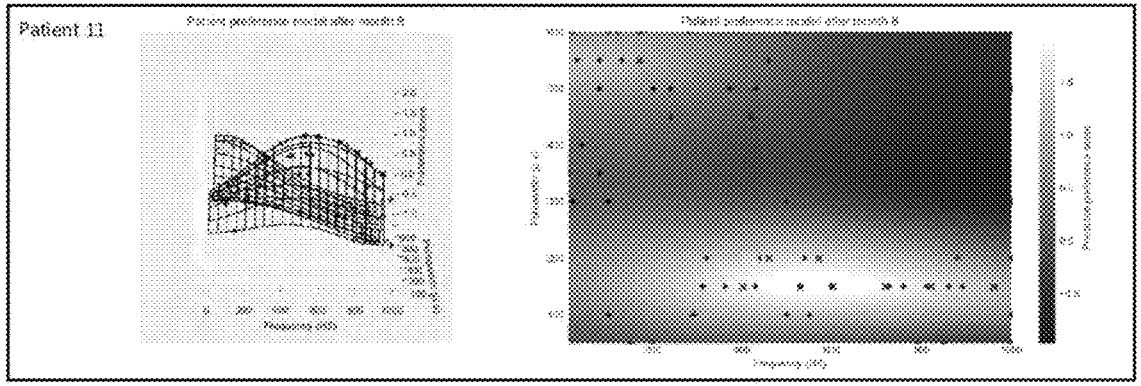
Figure 2I:
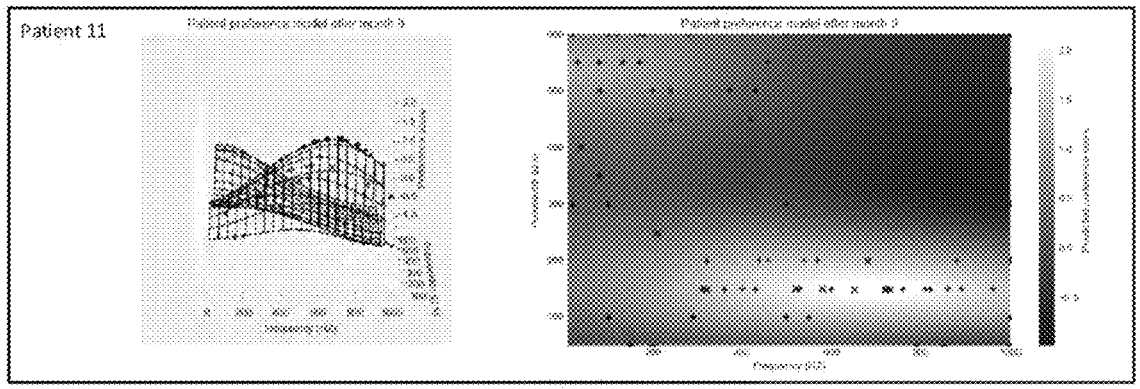
Figure 2J:
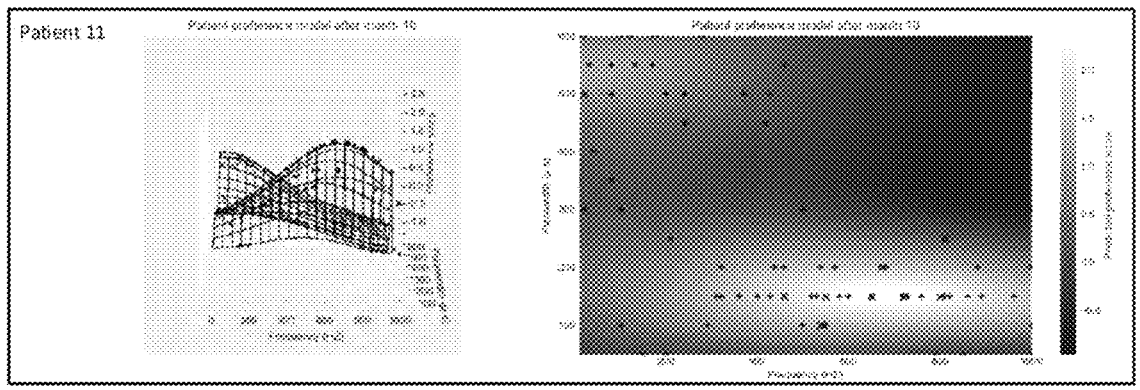
Figure 2K:
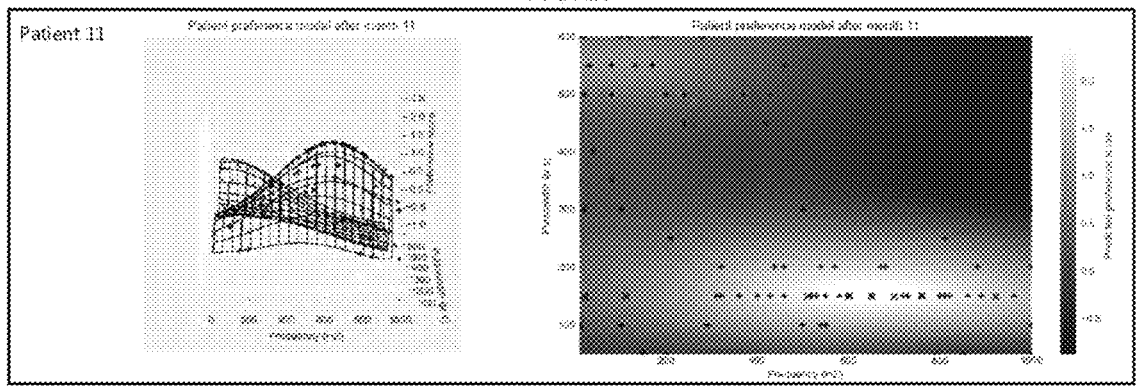
Figure 3A:
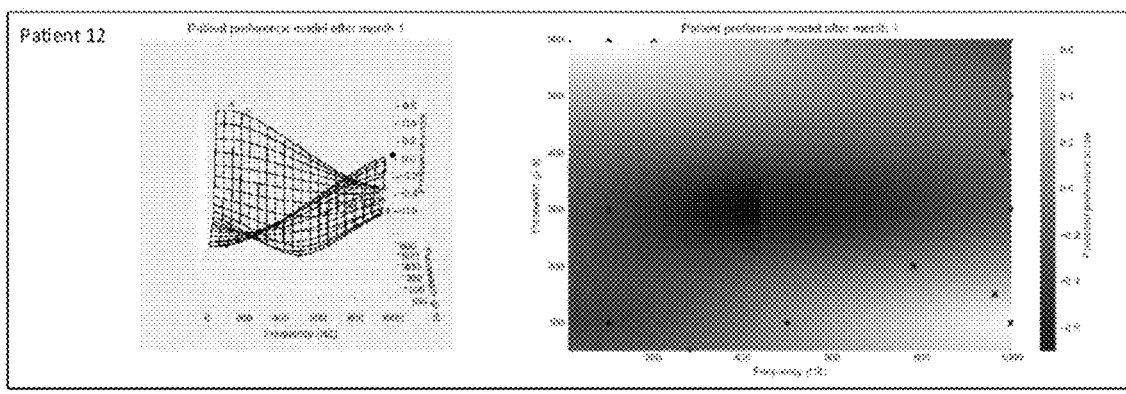
FIGS. 3A-3K depict a process for optimizing neurostimulation settings for a second example patient.
Figure 3B:
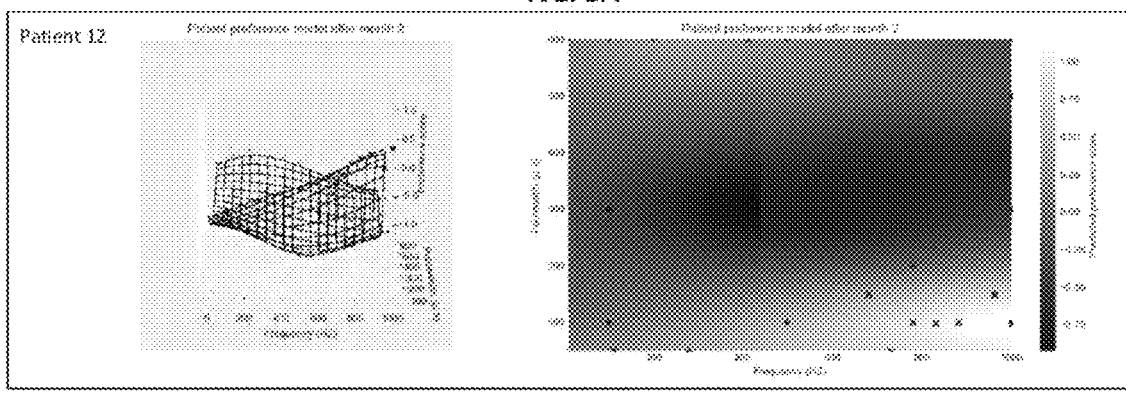
Figure 3C:
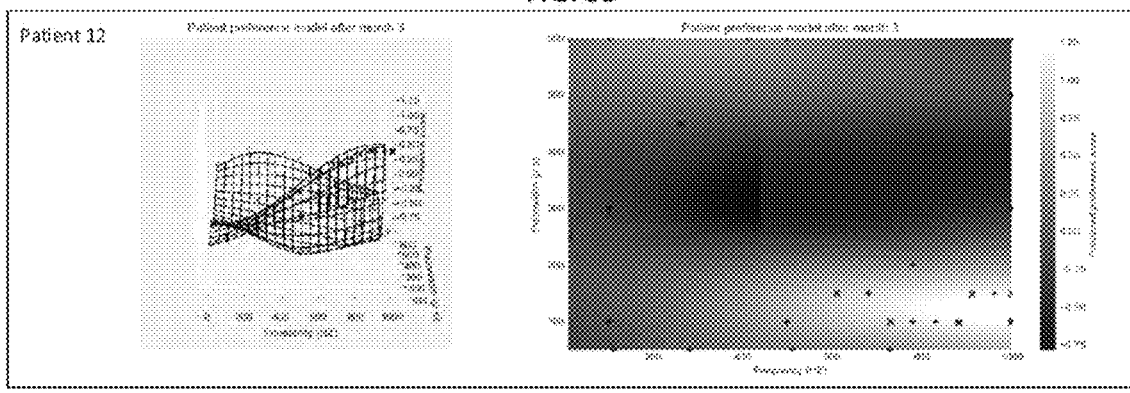
Figure 3D:
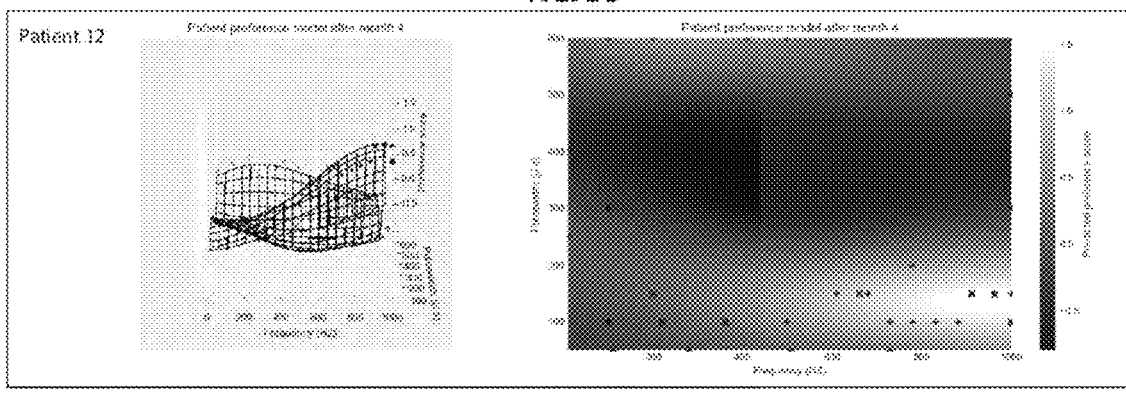
Figure 3E:
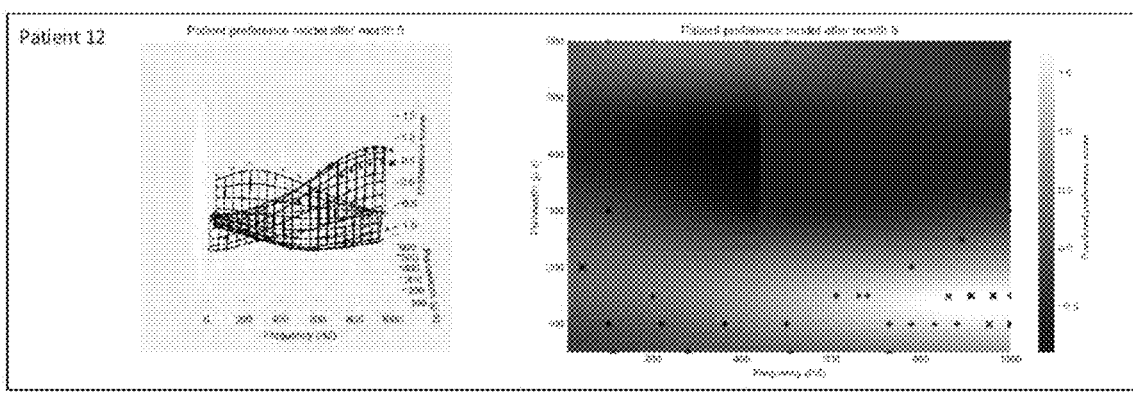
Figure 3F:
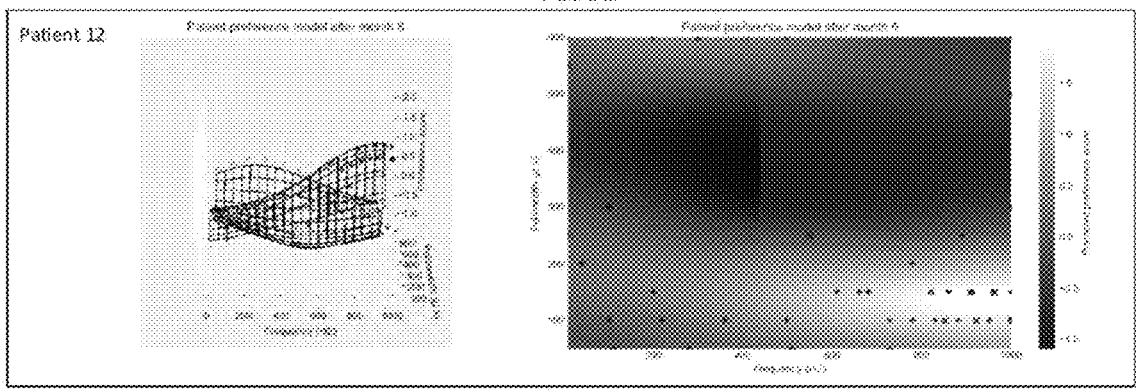
Figure 3G:
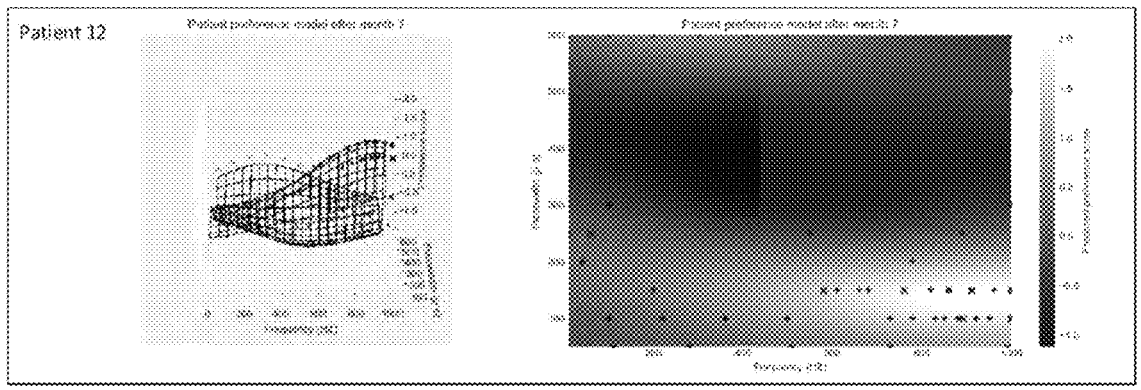
Figure 3H:
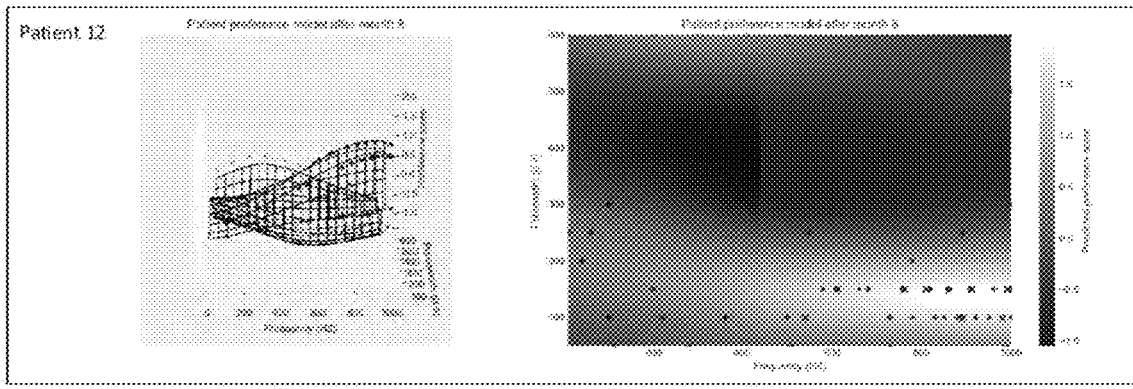
Figure 3I:
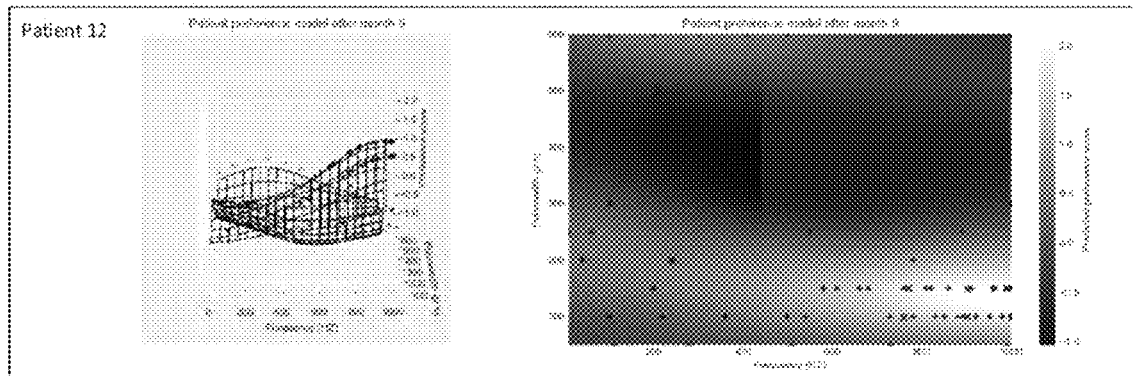
Figure 3J:
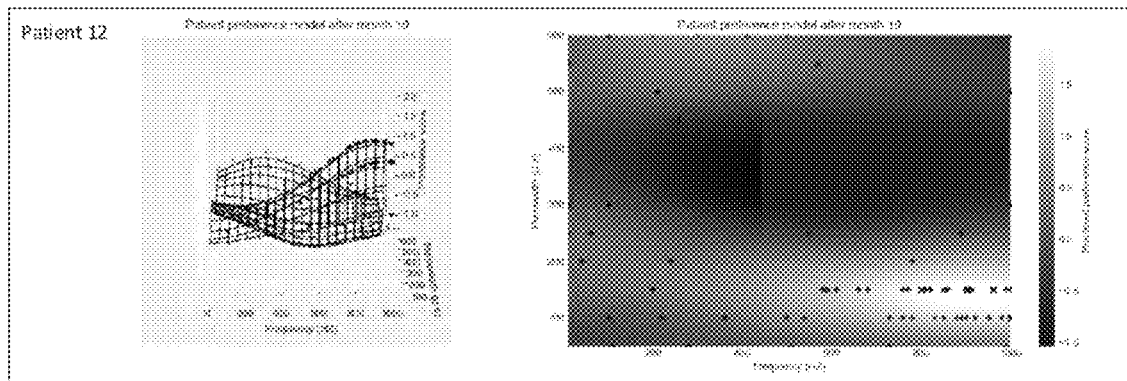
Figure 3K:
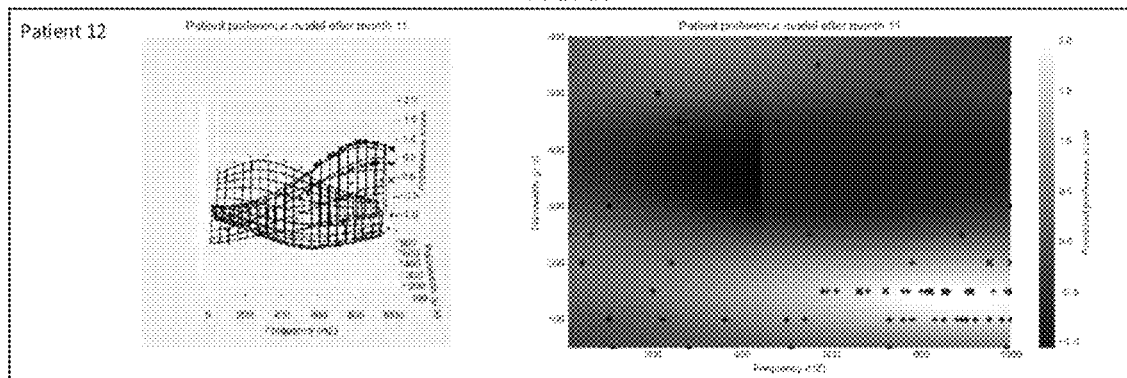
Figure 4A:
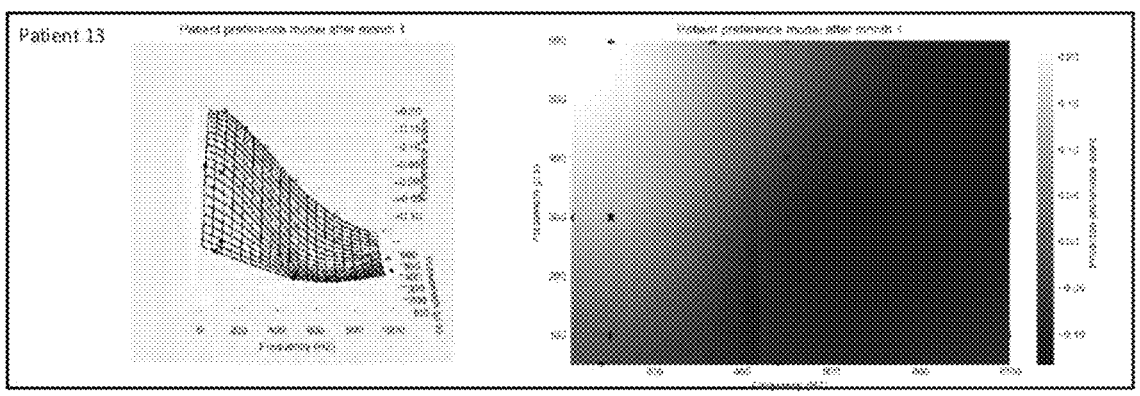
FIGS. 4A-4K depict a process for optimizing neurostimulation settings for a third example patient.
Figure 4B:
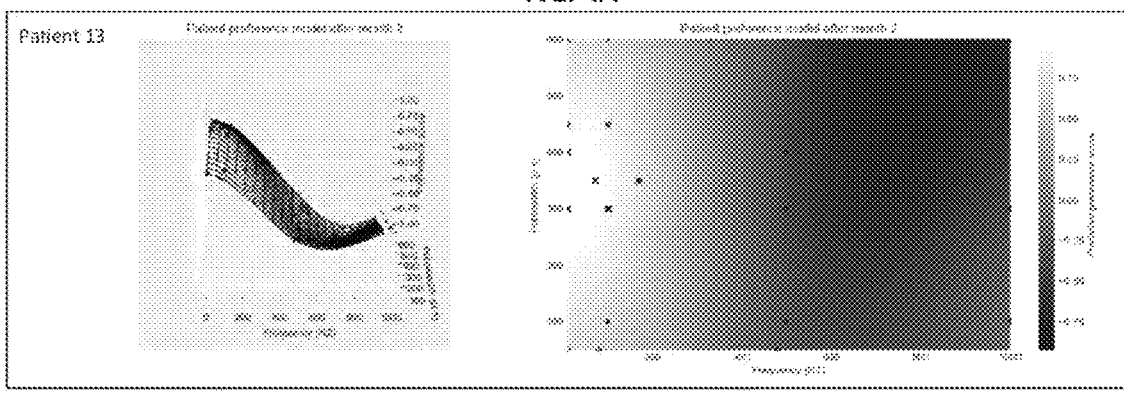
Figure 4C:
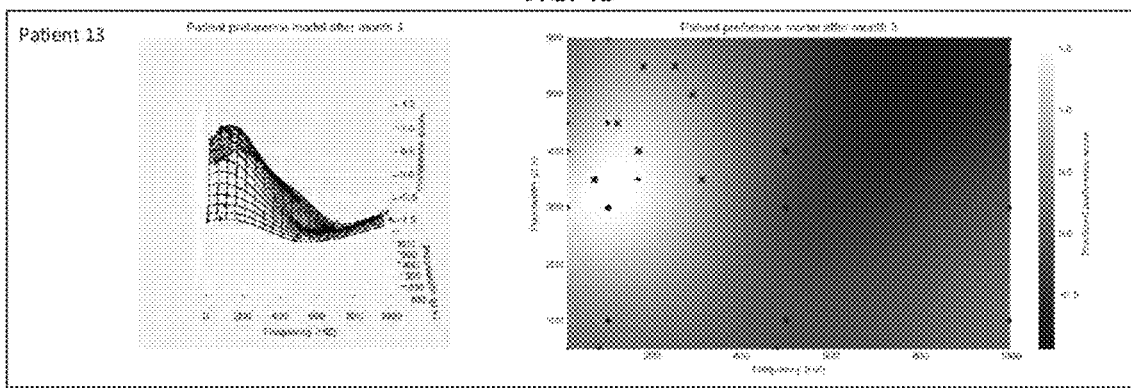
Figure 4D:
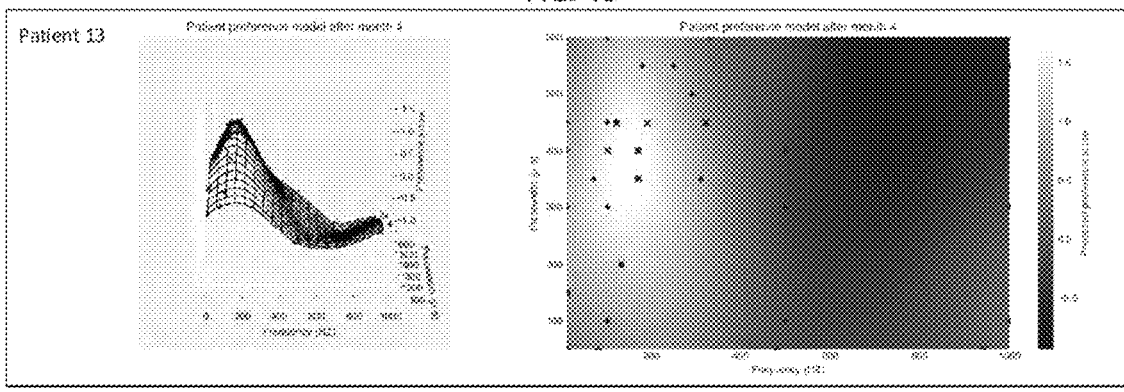
Figure 4E:
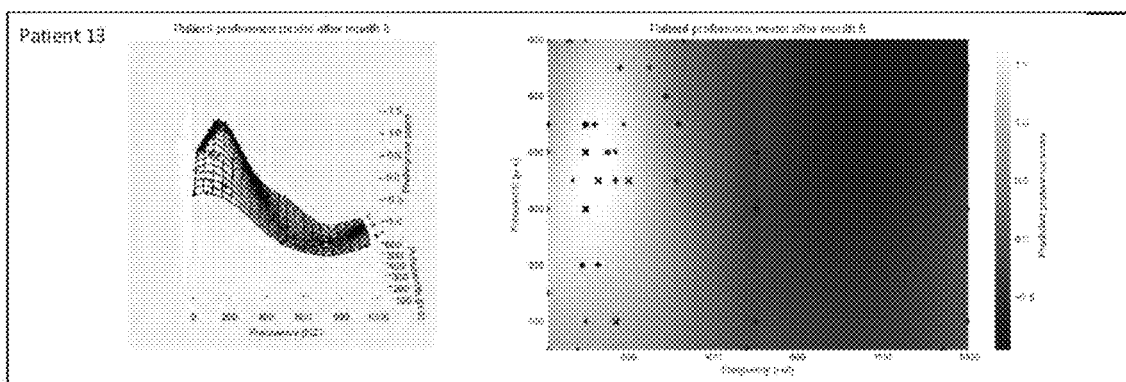
Figure 4F:
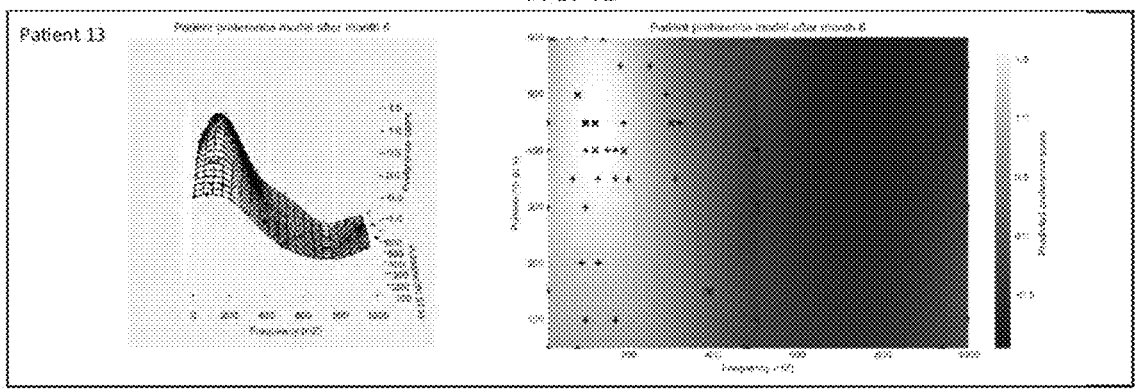
Figure 4G:
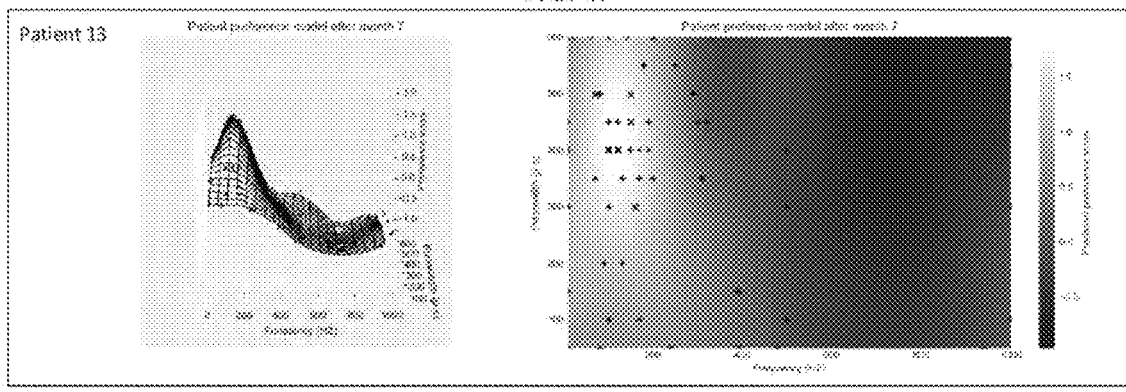
Figure 4H:
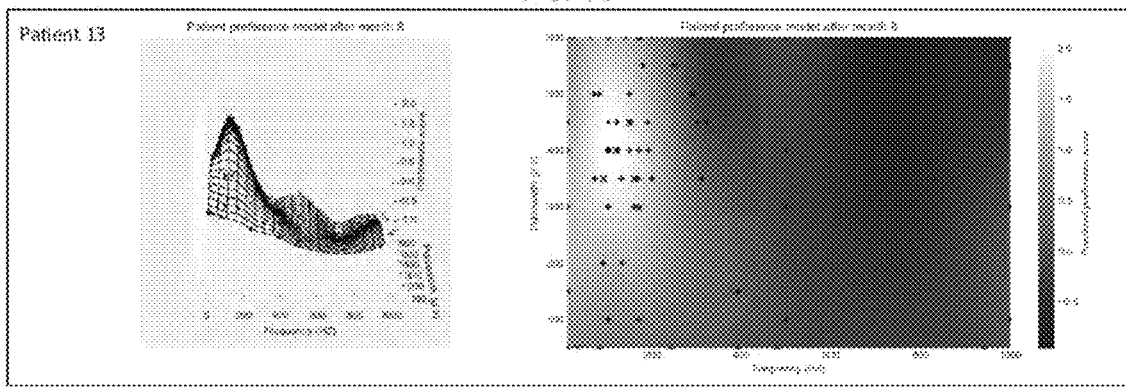
Figure 4I:
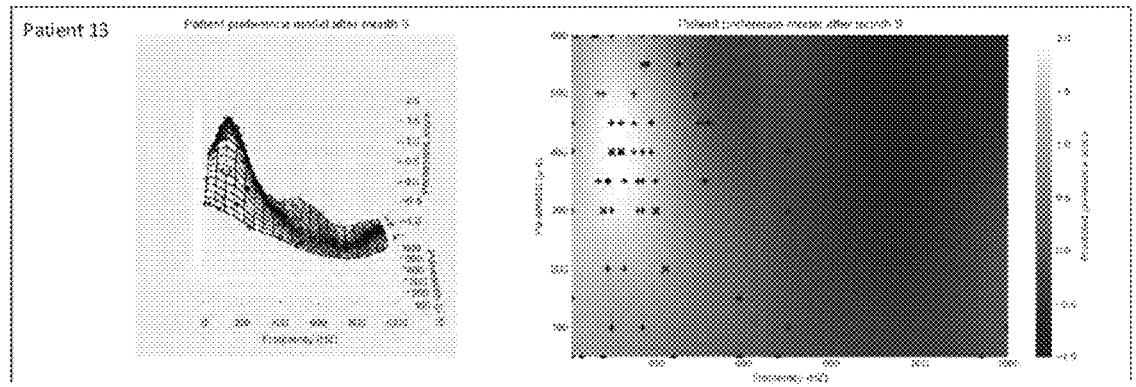
Figure 4J:
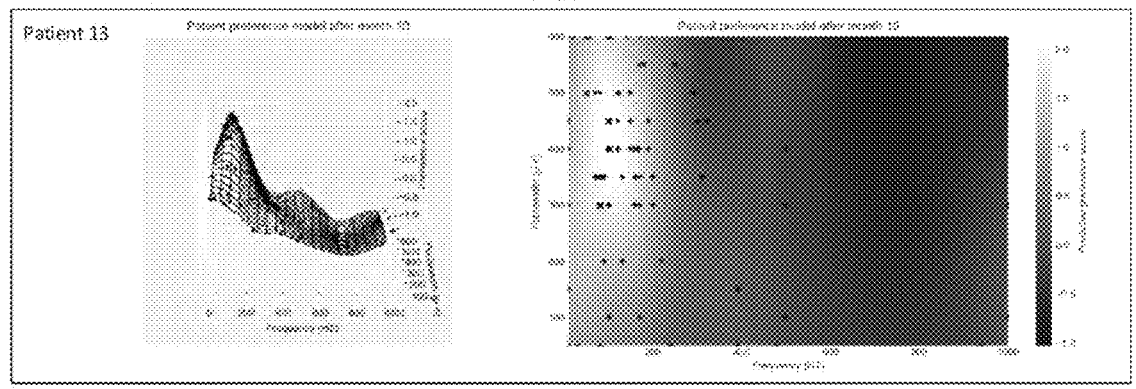
Figure 4K:
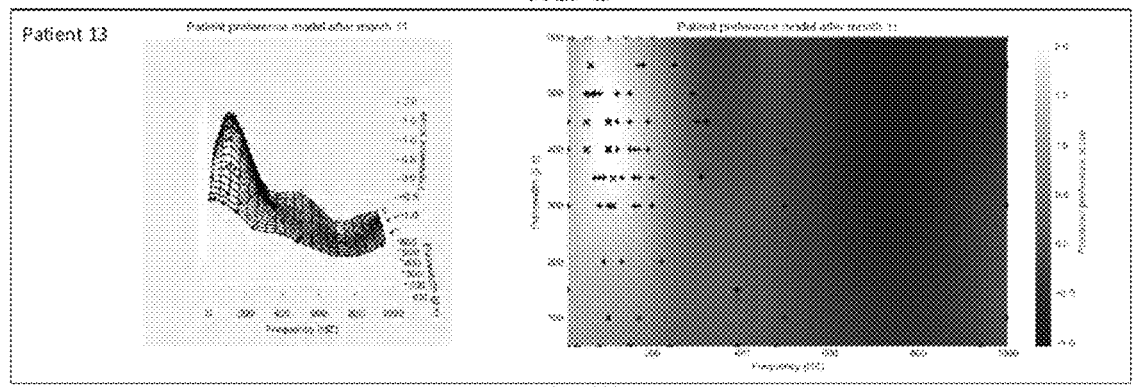
Figure 5A:
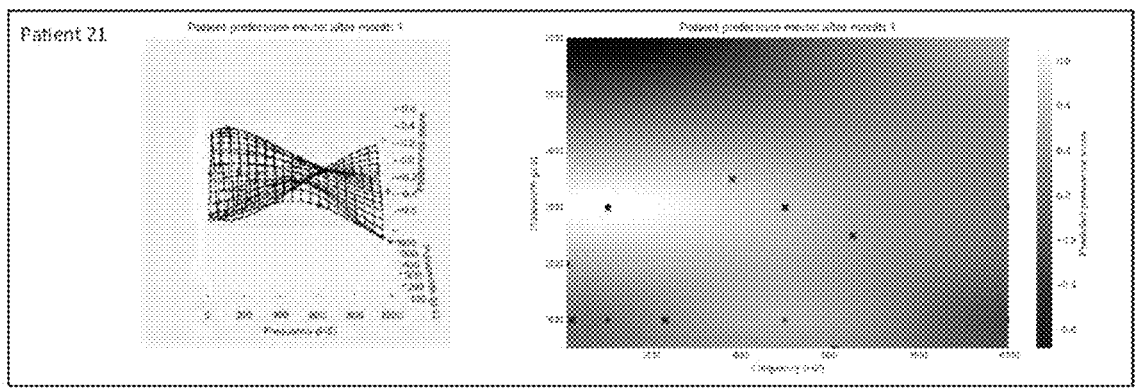
FIGS. 5A-5K depict a process for optimizing neurostimulation settings for a fourth example patient.
Figure 5B:
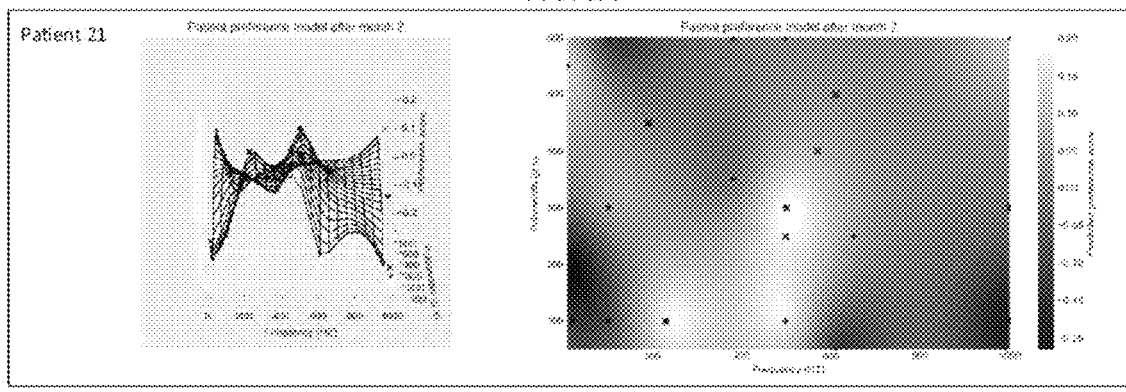
Figure 5C:
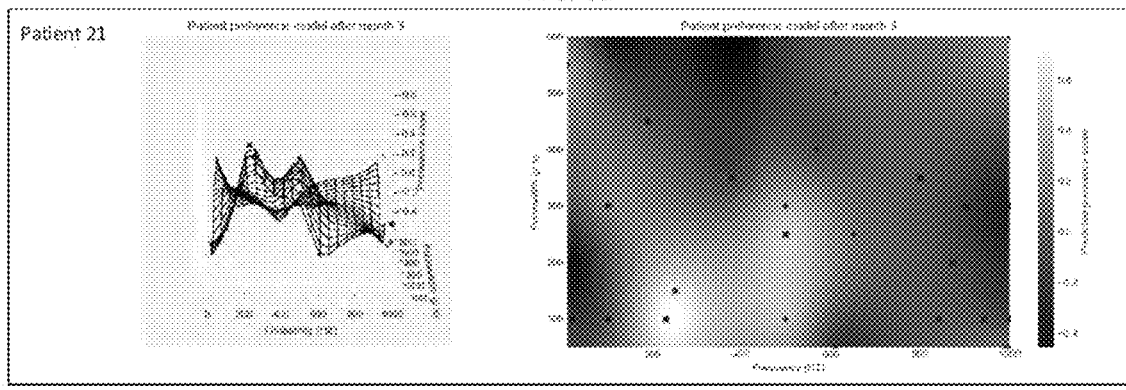
Figure 5D:
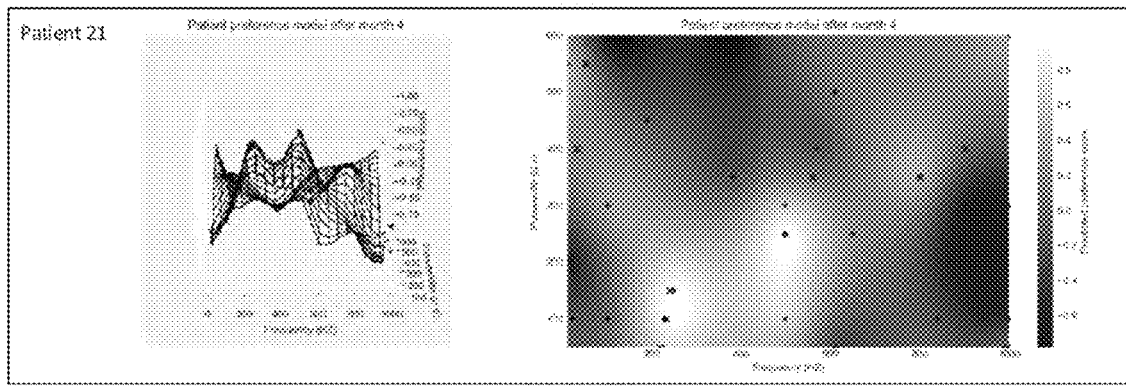
Figure 5E:
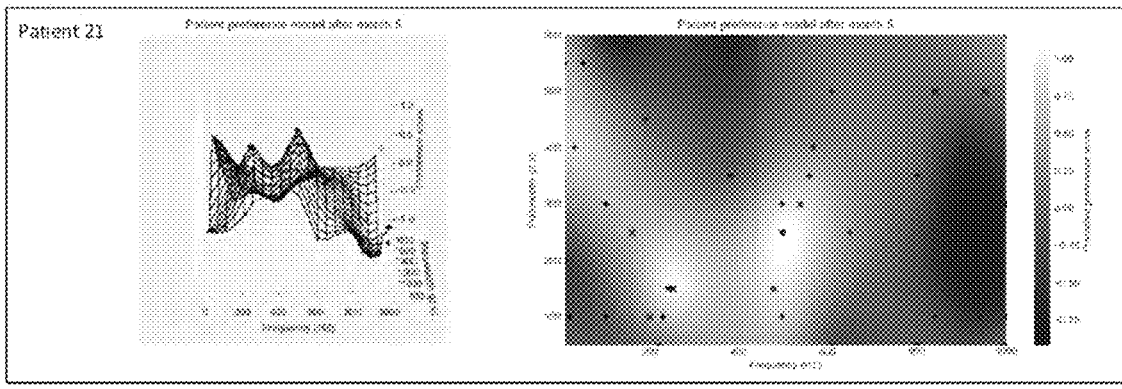
Figure 5F:
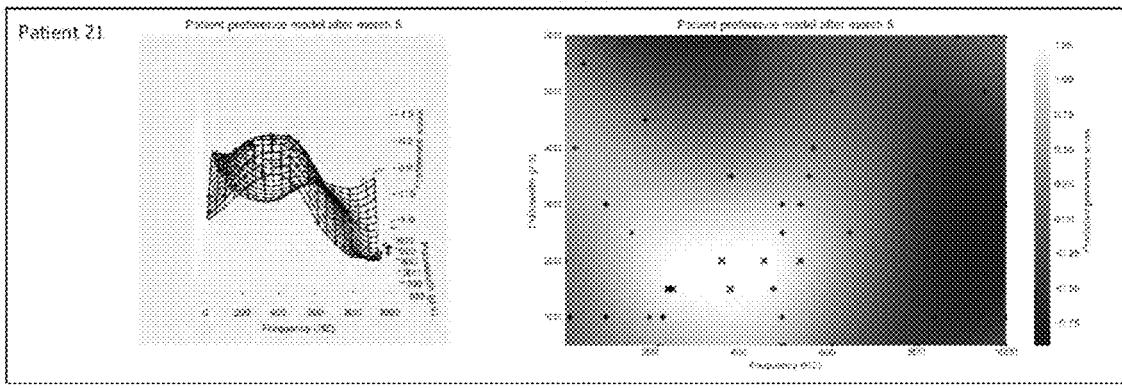
Figure 5G:
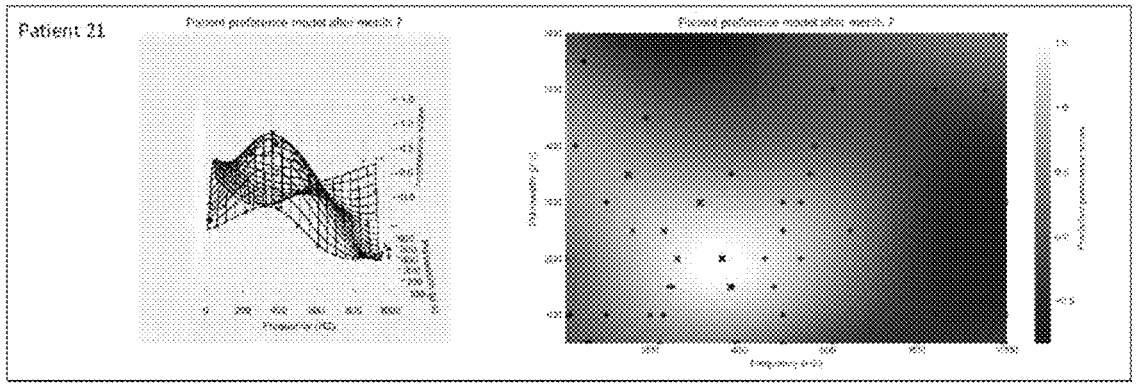
Figure 5H:
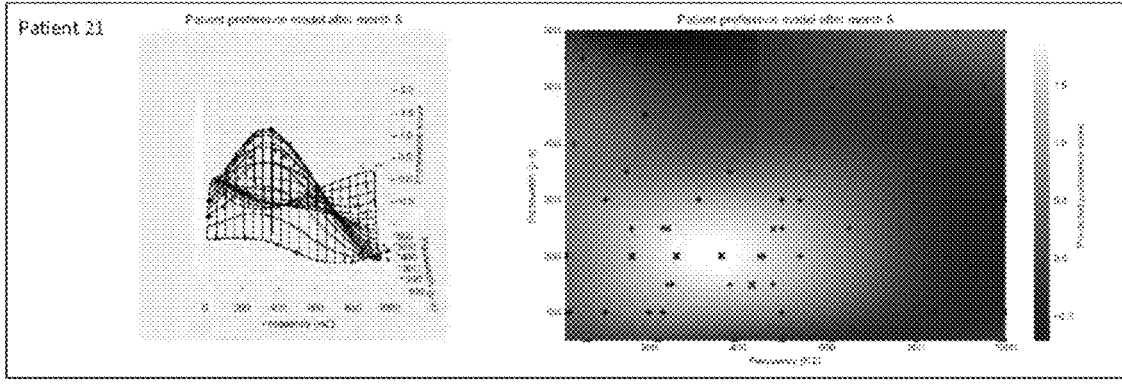
Figure 5I:
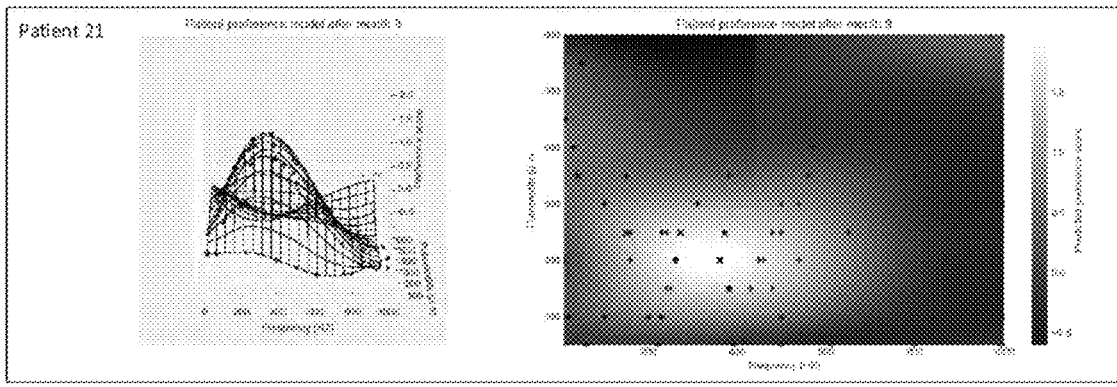
Figure 5J:
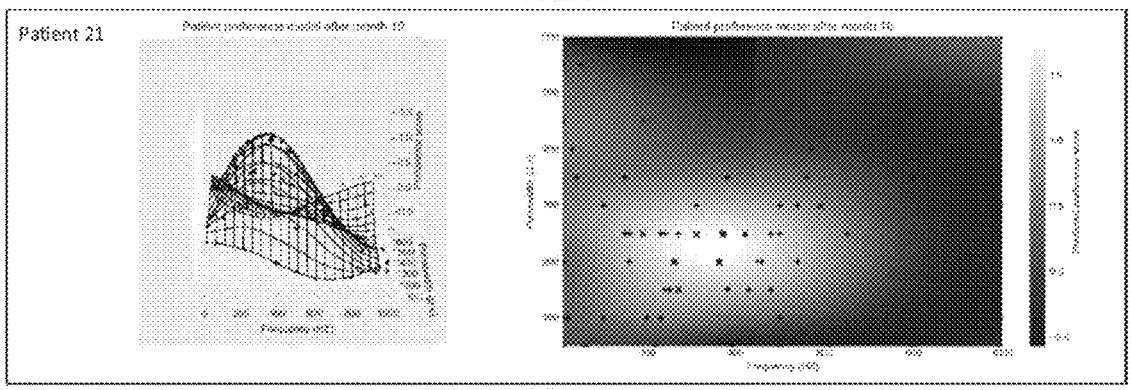
Figure 5K:
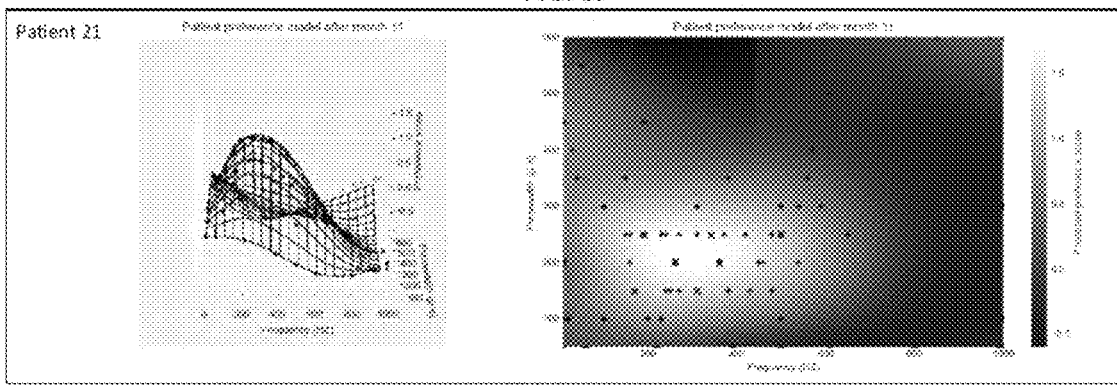
Figure 6A:
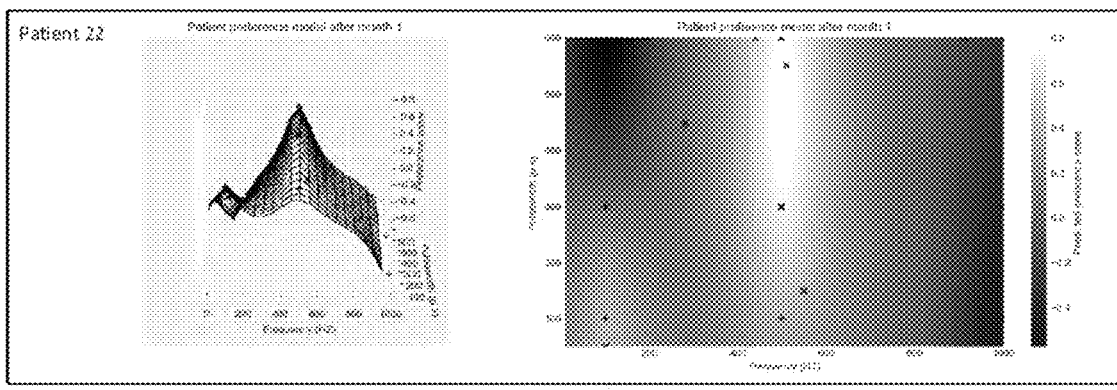
FIGS. 6A-6K depict a process for optimizing neurostimulation settings for a fifth example patient.
Figure 6B:
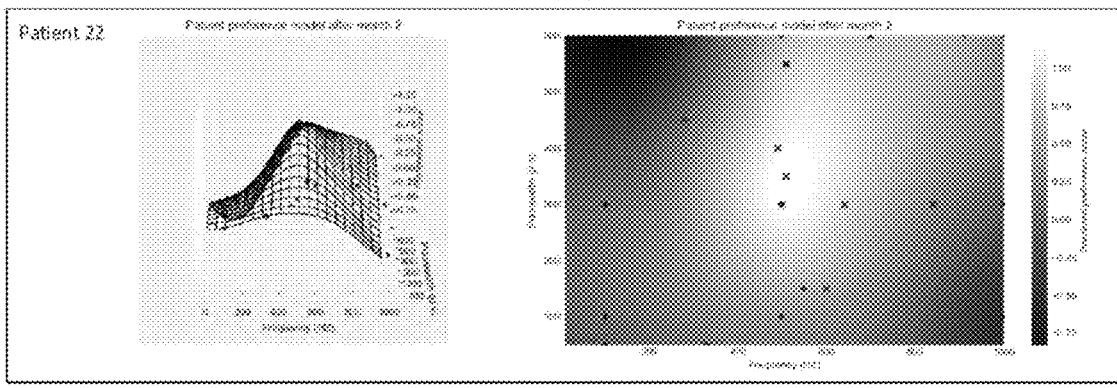
Figure 6C:
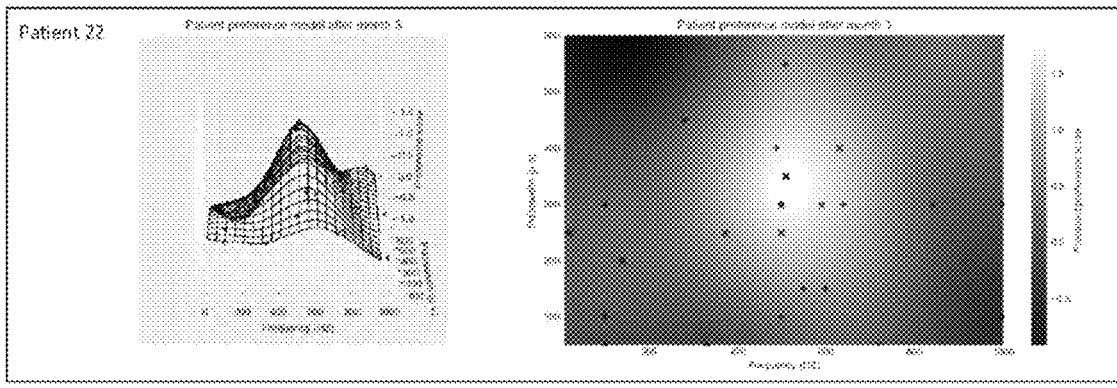
Figure 6D:
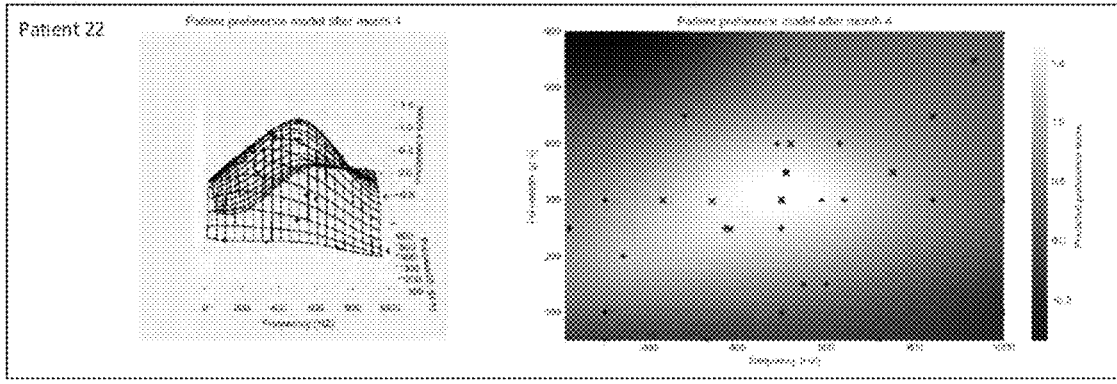
Figure 6E:
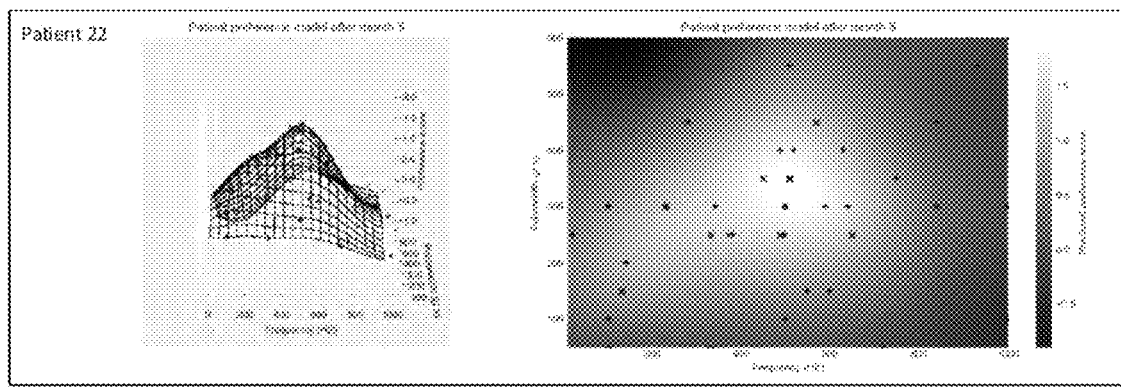
Figure 6F:
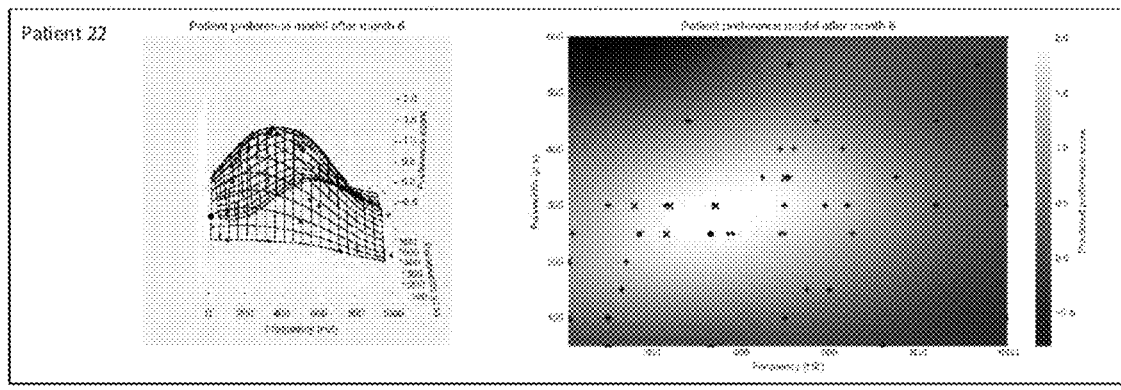
Figure 6G:
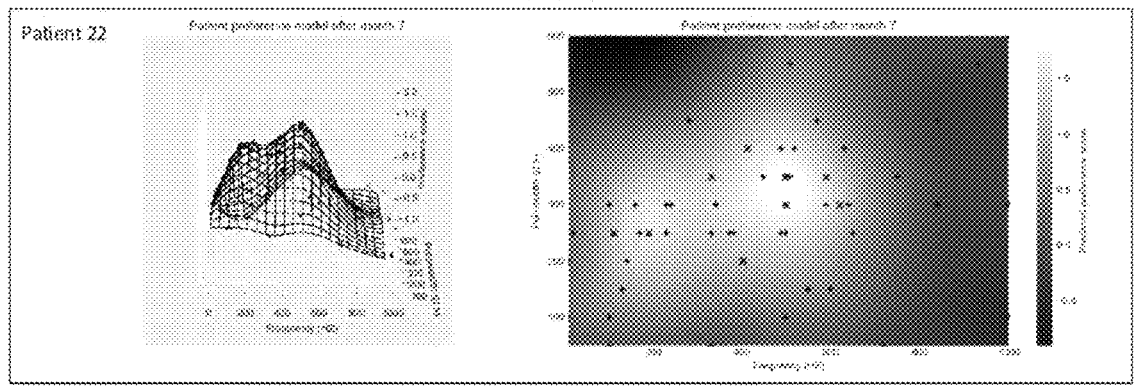
Figure 6H:
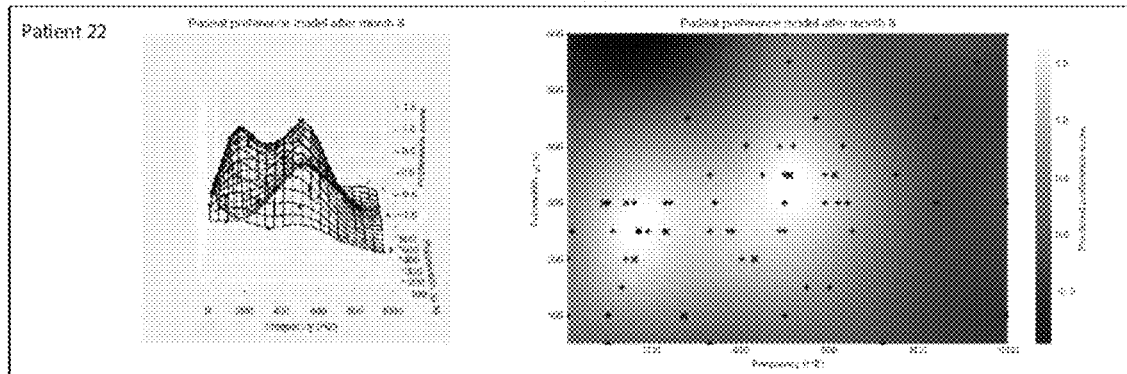
Figure 6I:
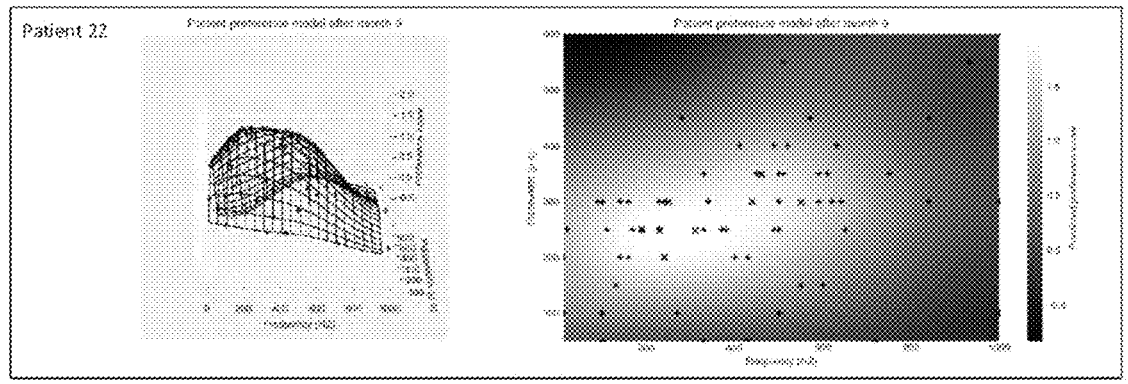
Figure 6J:
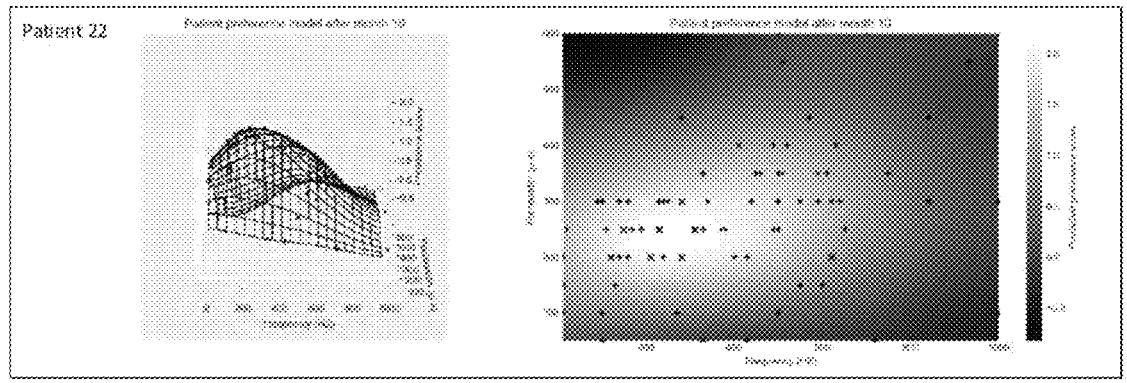
Figure 6K:
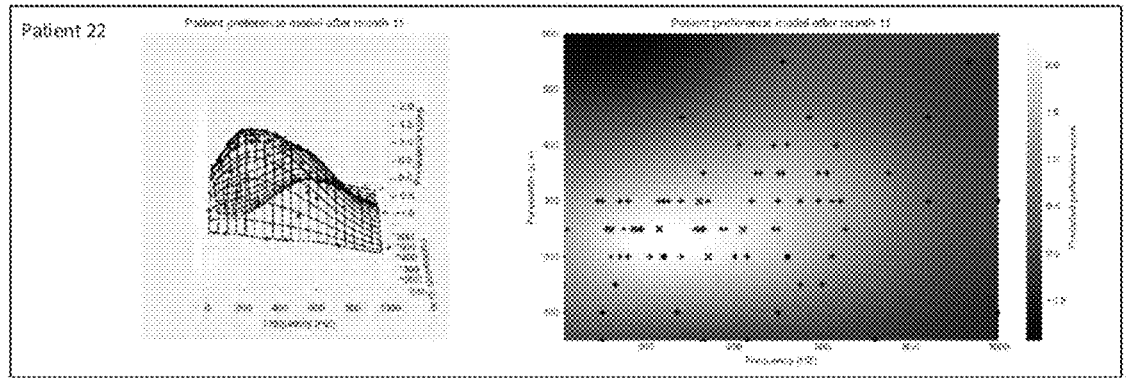
Figure 7A:
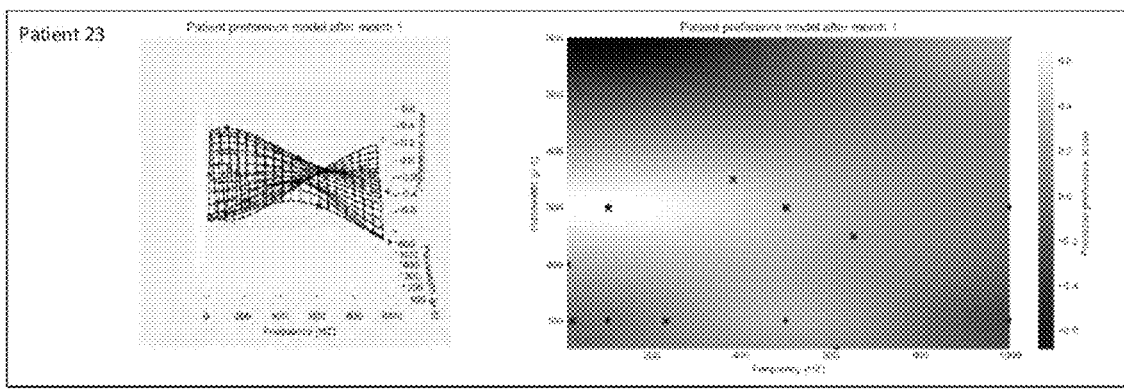
FIGS. 7A-7K depict a process for optimizing neurostimulation settings for a sixth example patient.
Figure 7B:
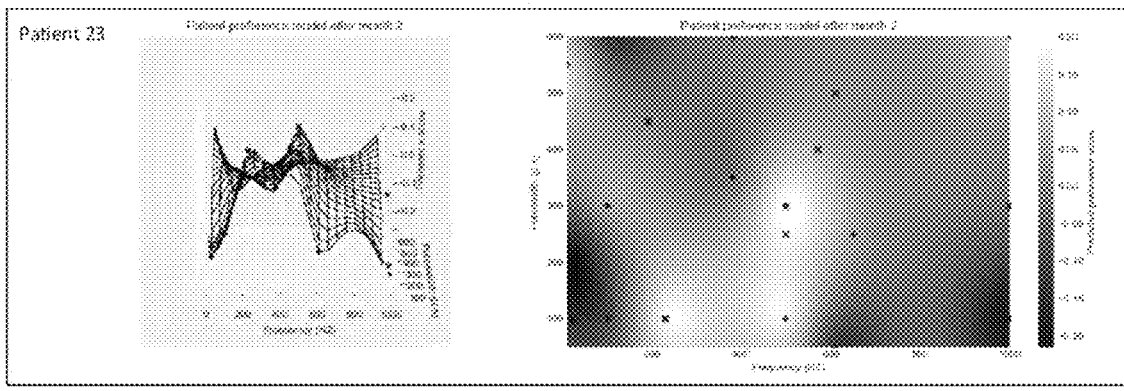
Figure 7C:
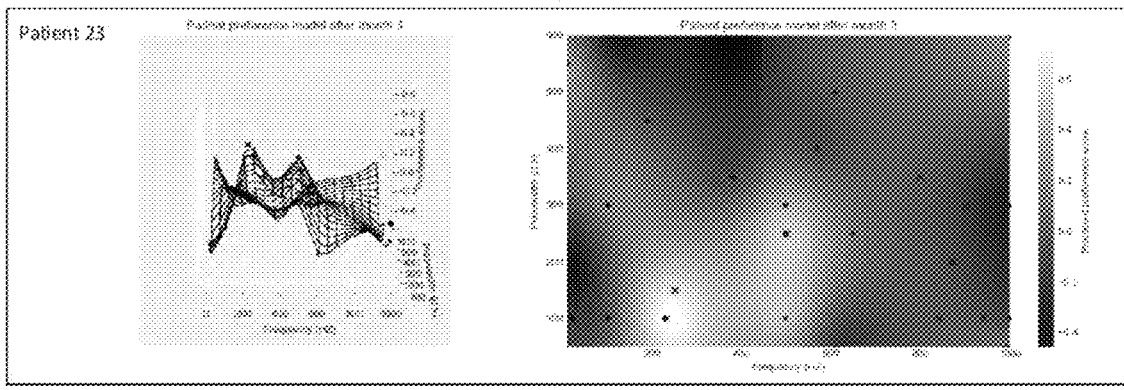
Figure 7D:
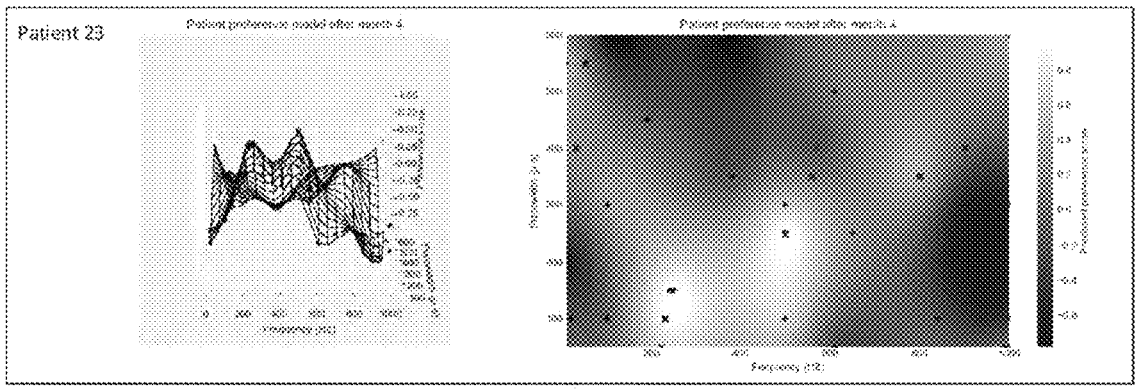
Figure 7E:
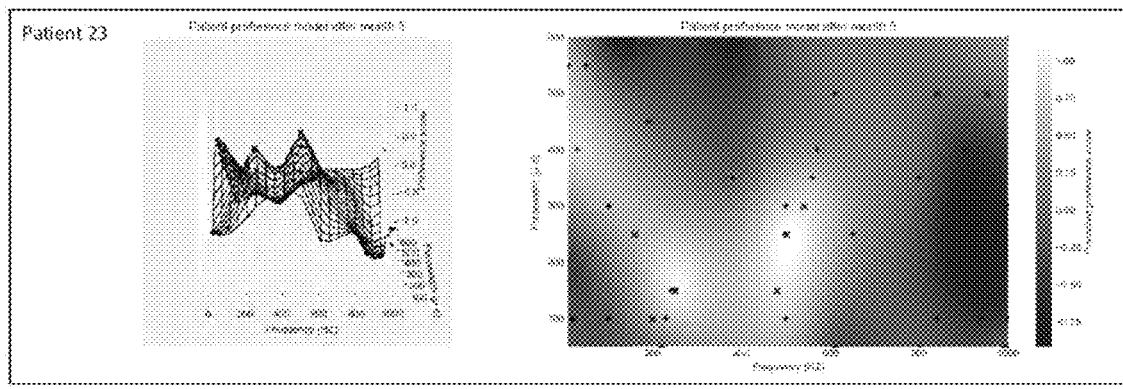
Figure 7F:
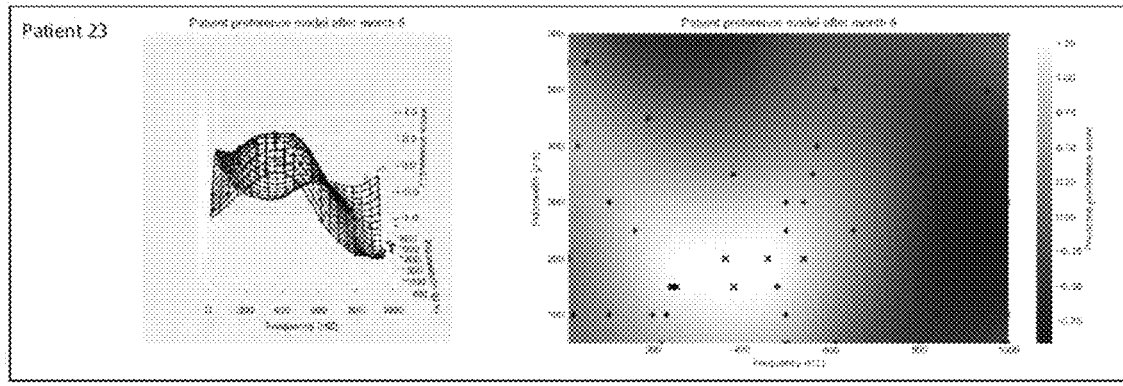
Figure 7G:
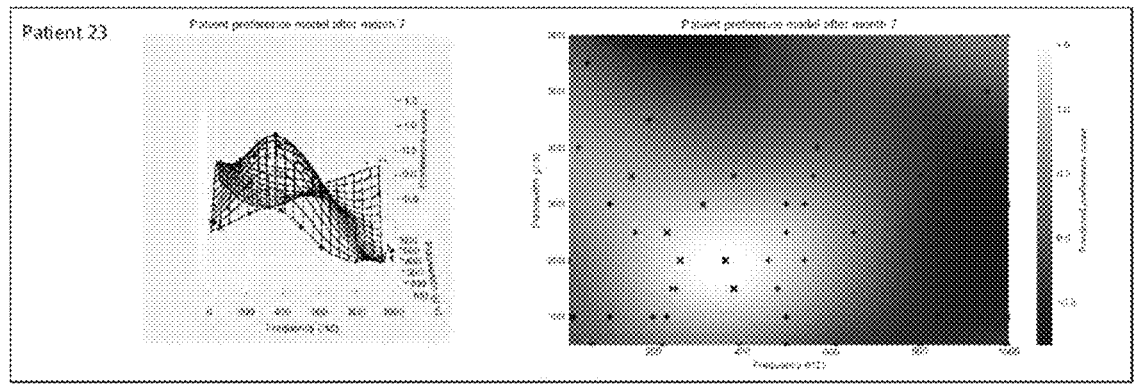
Figure 7H:
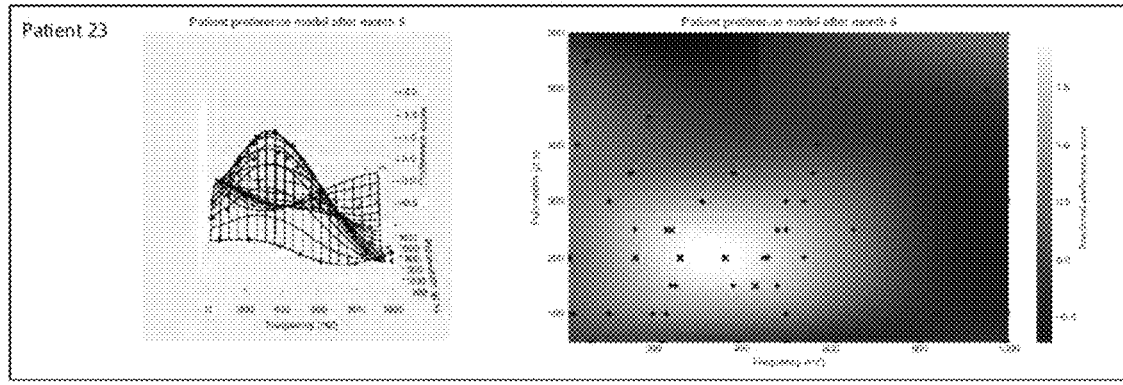
Figure 7I:
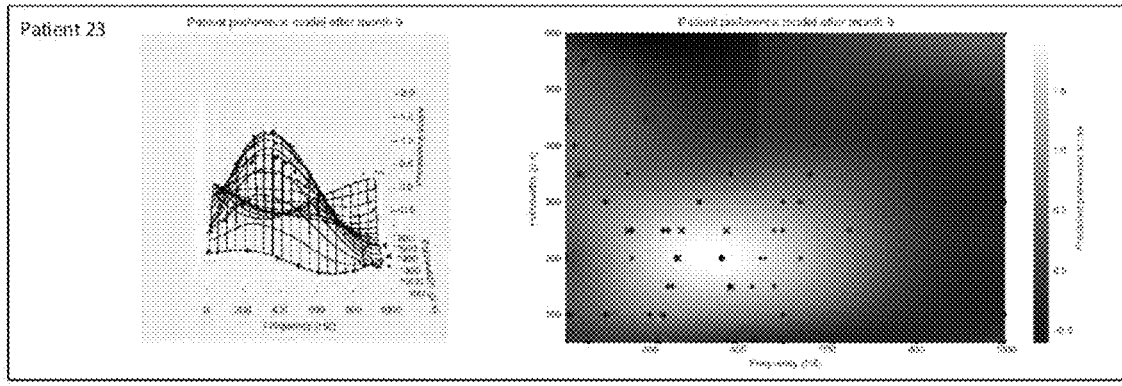
Figure 7J:
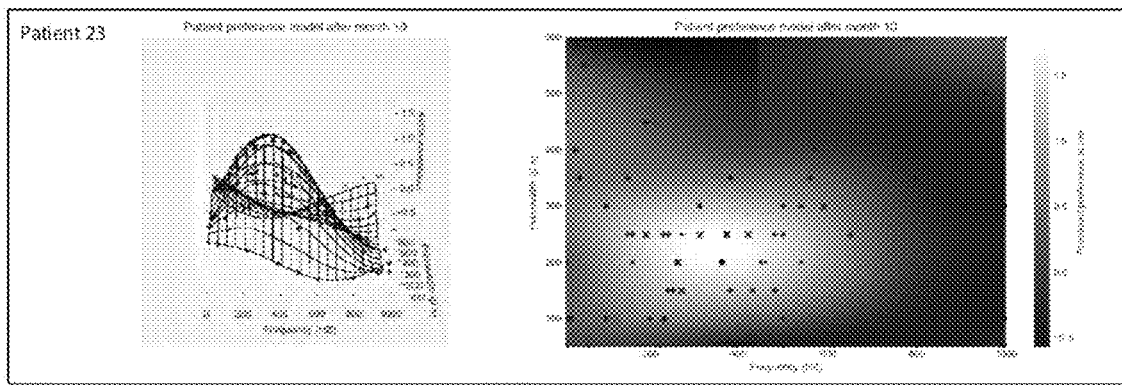
Figure 7K:
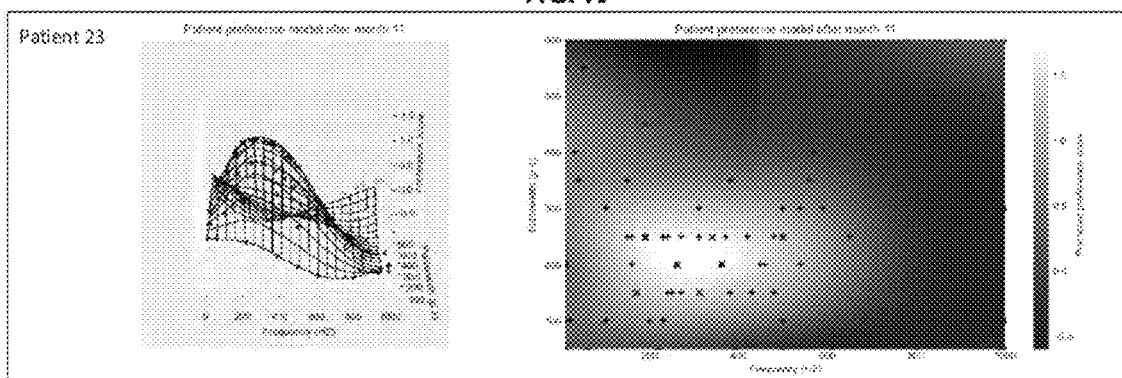
Figure 8A:
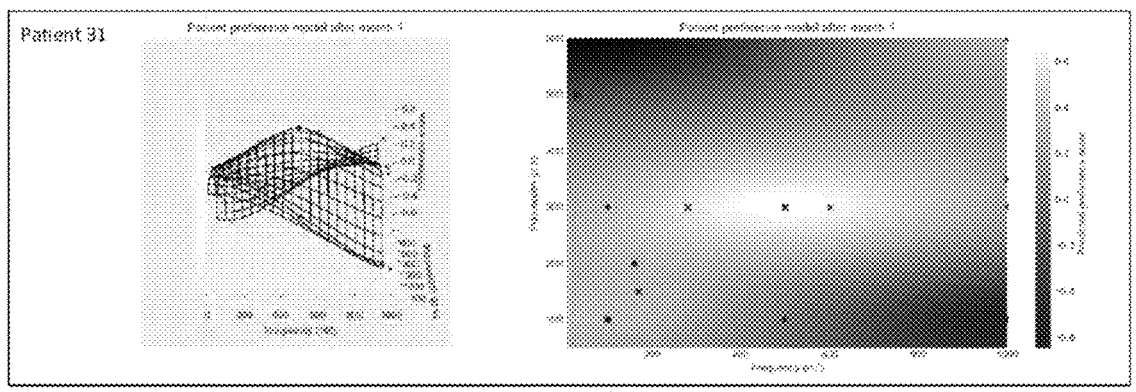
FIGS. 8A-8K depict a process for optimizing neurostimulation settings for a seventh example patient.
Figure 8B:
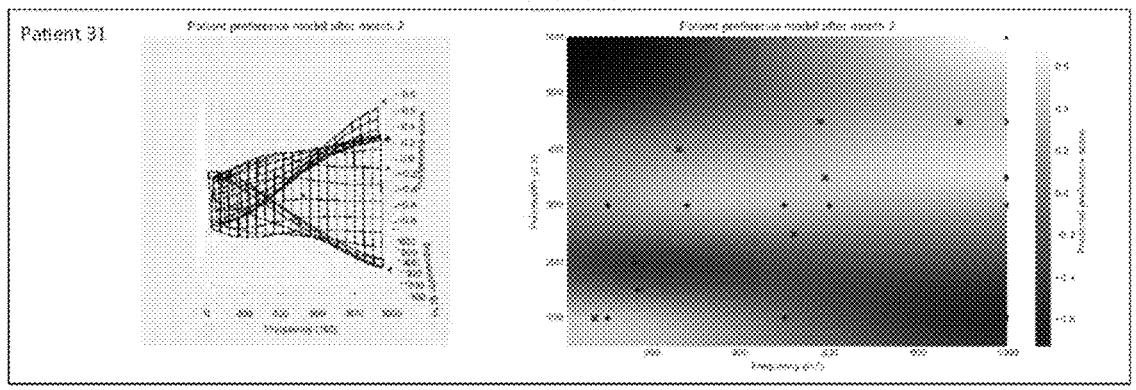
Figure 8C:
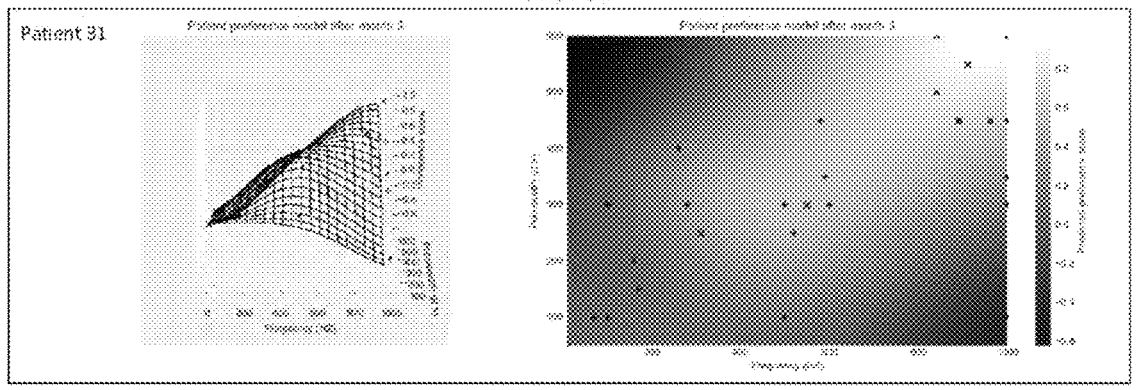
Figure 8D:
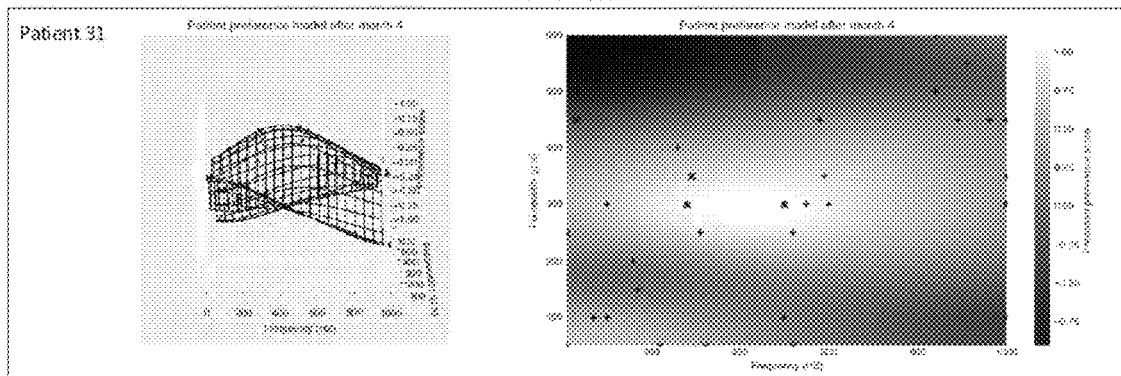
Figure 8E:
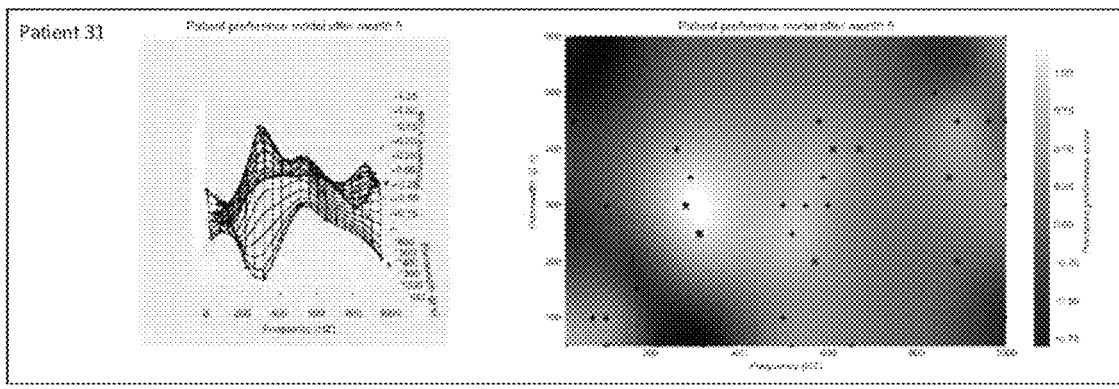
Figure 8F:
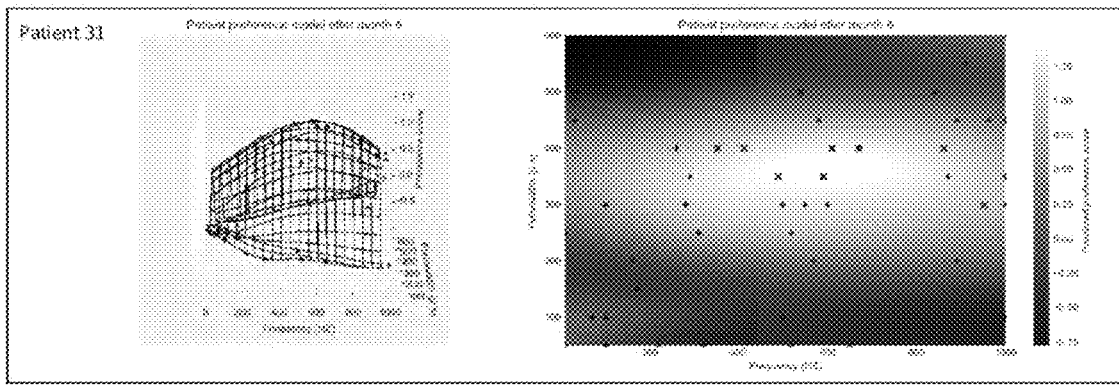
Figure 8G:
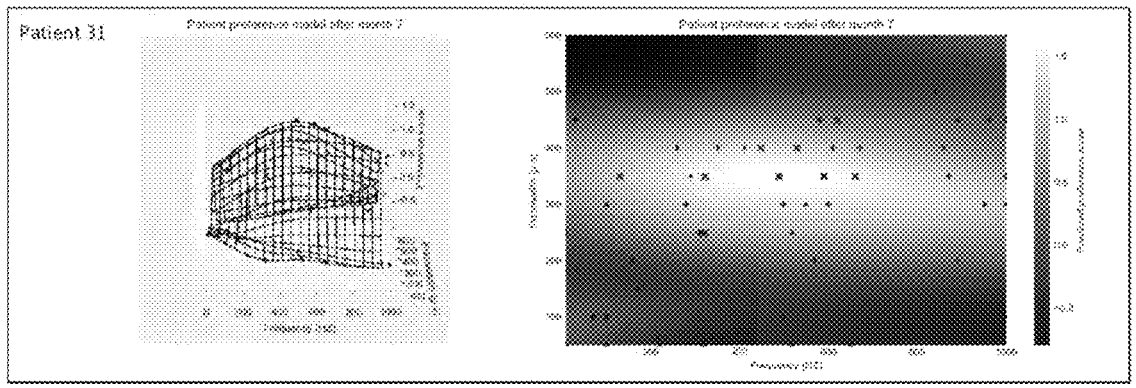
Figure 8H:
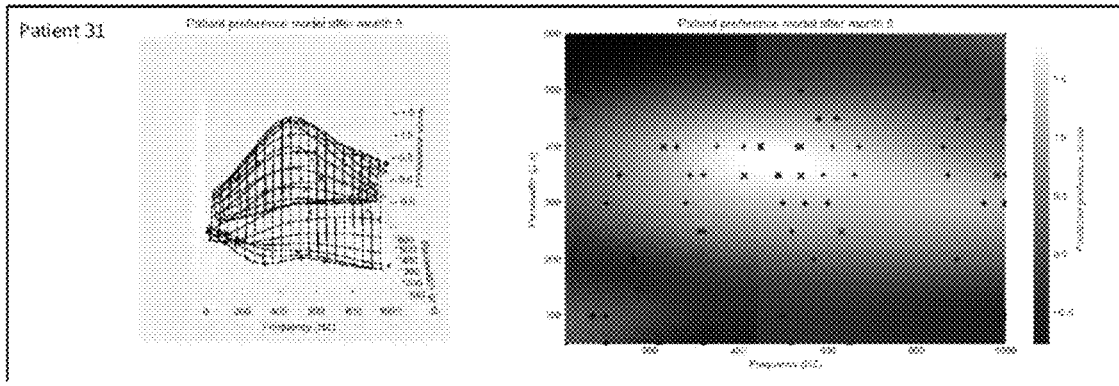
Figure 8I:
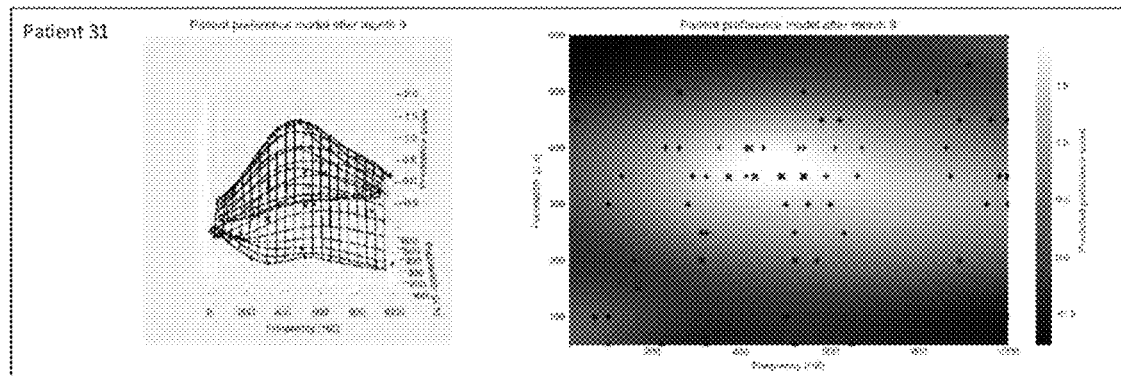
Figure 8J:
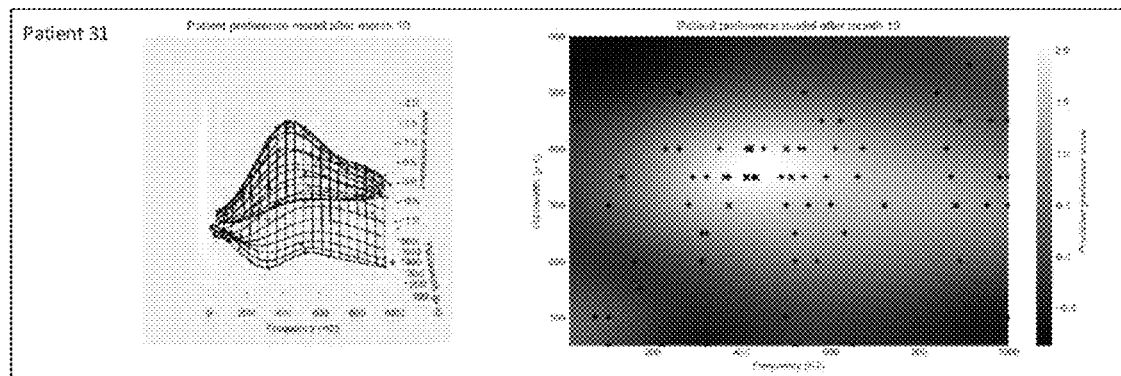
Figure 8K:
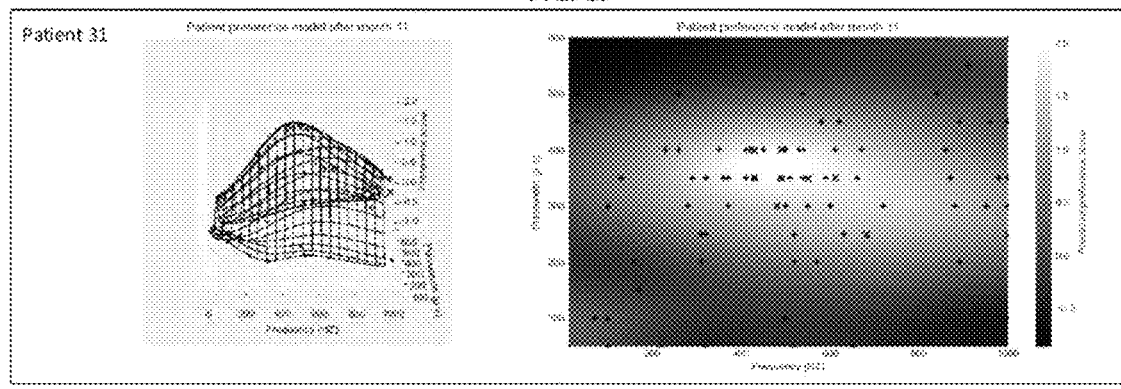
Figure 9A:
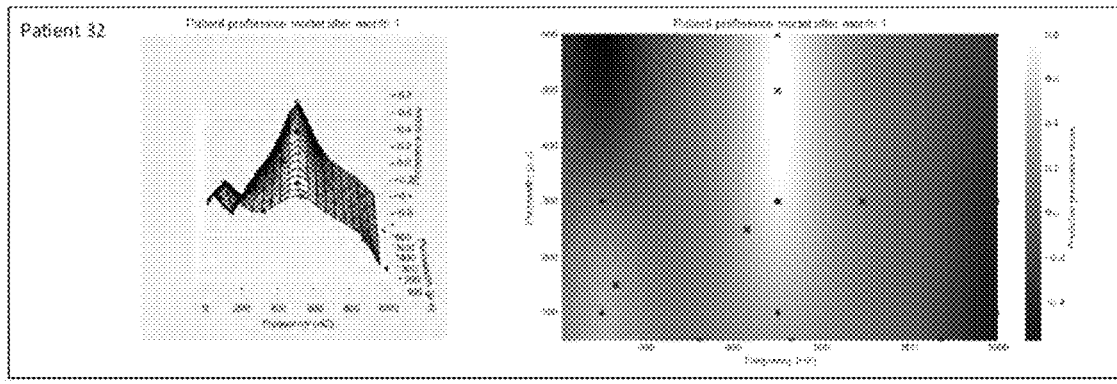
FIGS. 9A-9K depict a process for optimizing neurostimulation settings for a eighth example patient.
Figure 9B:
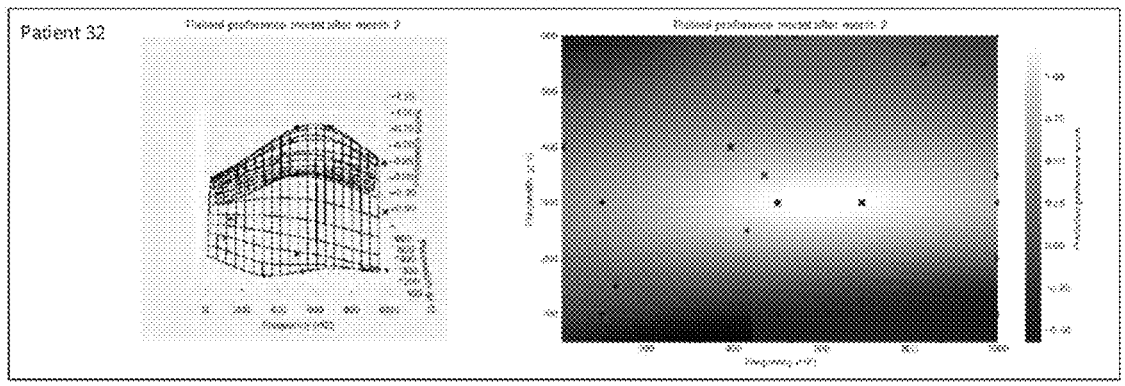
Figure 9C:
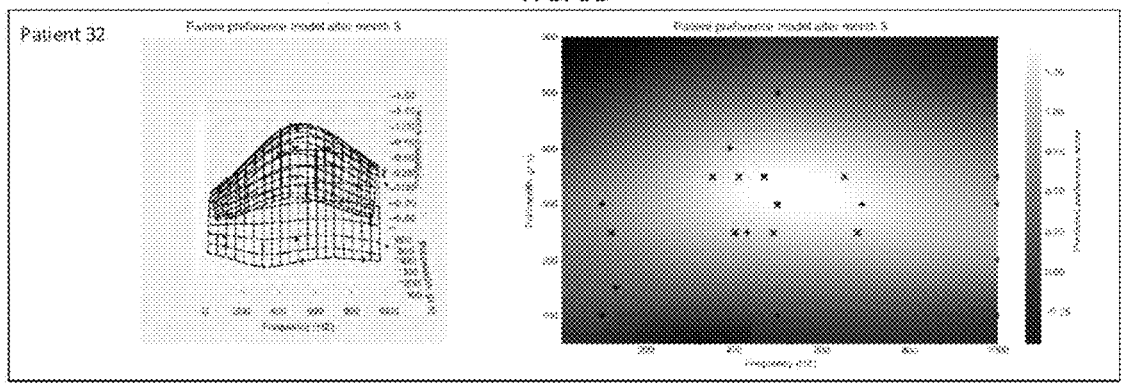
Figure 9D:
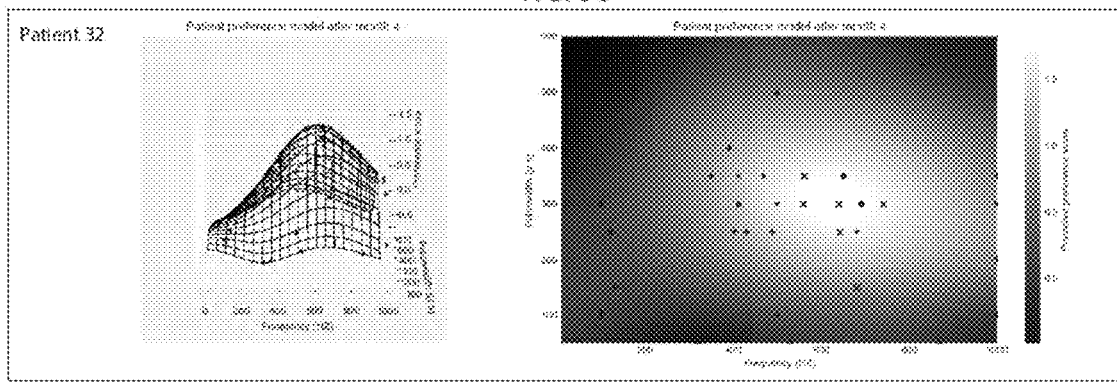
Figure 9E:
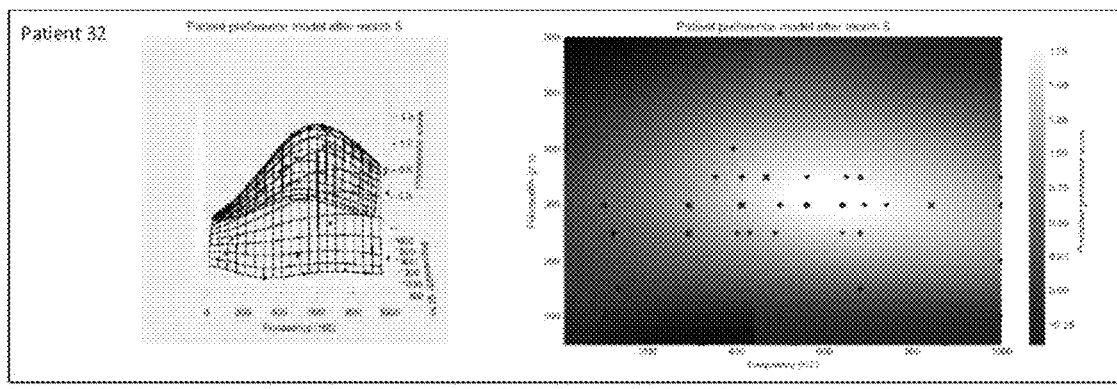
Figure 9F:
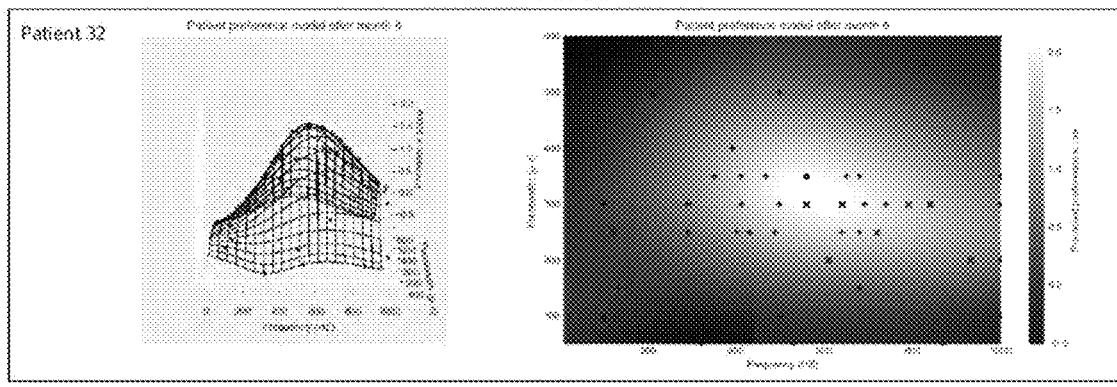
Figure 9G:
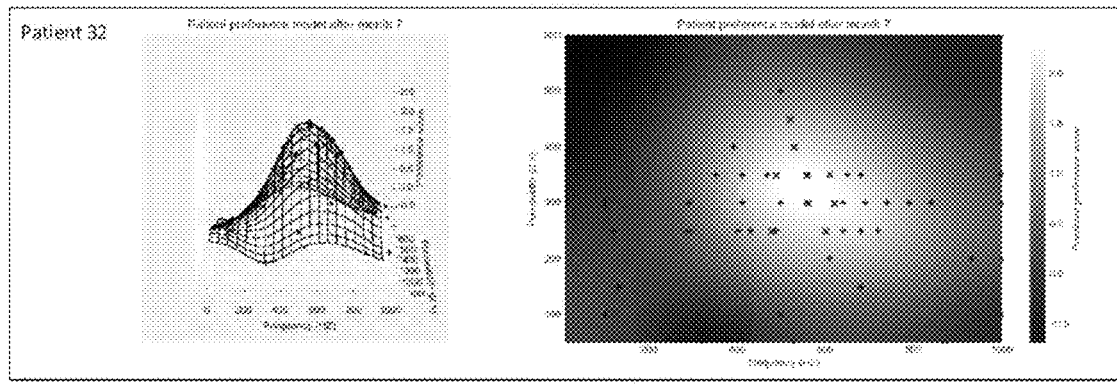
Figure 9H:
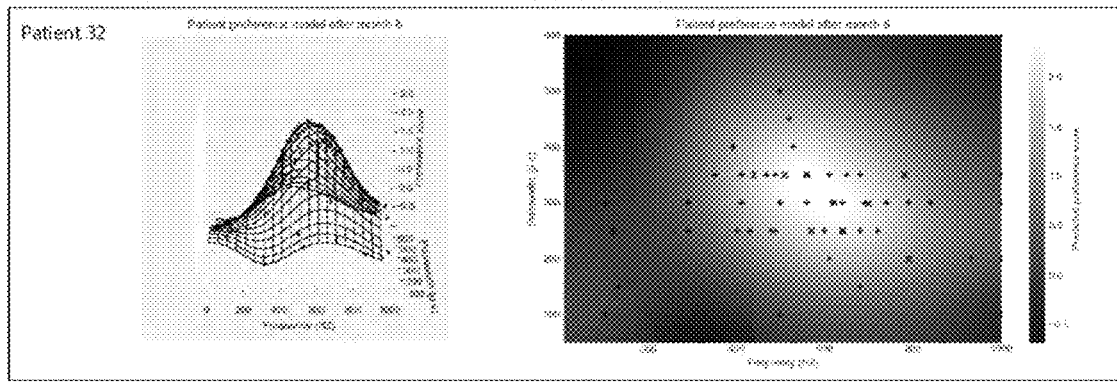
Figure 9I:
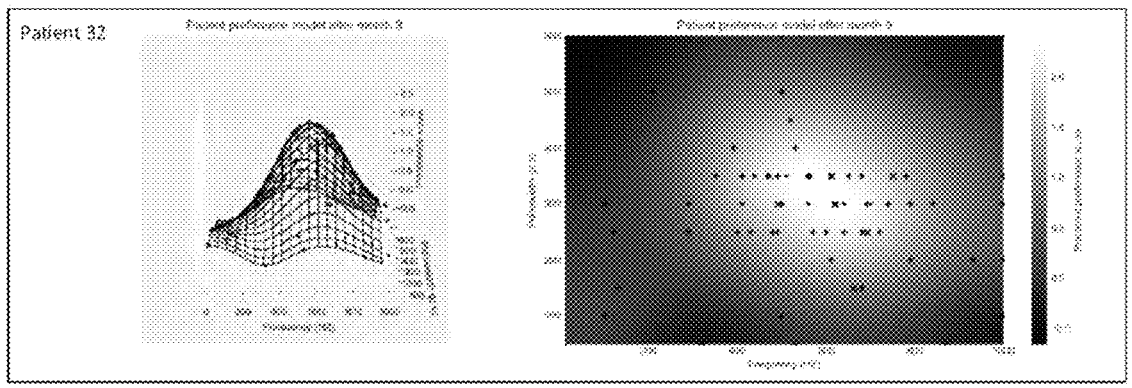
Figure 9J:
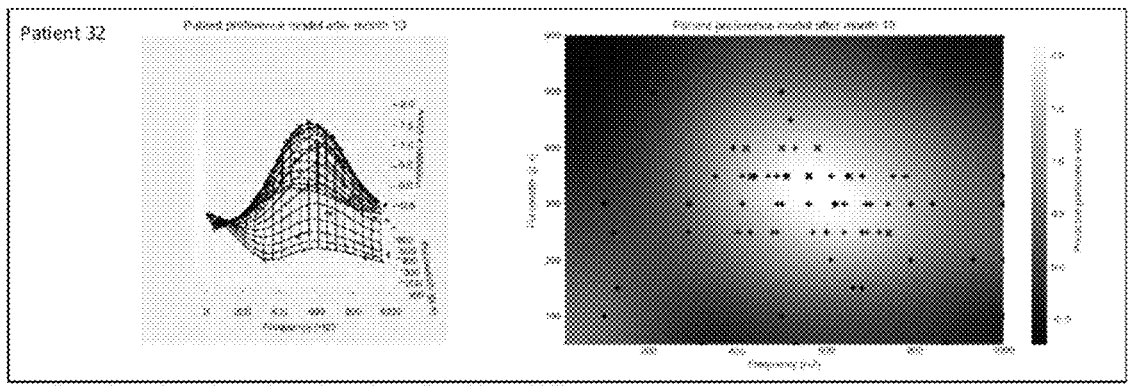
Figure 9K:
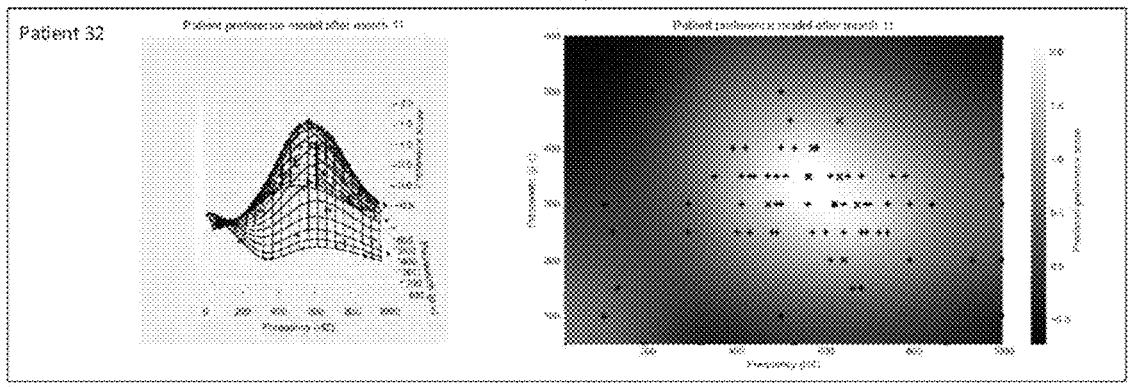
Figure 10A:
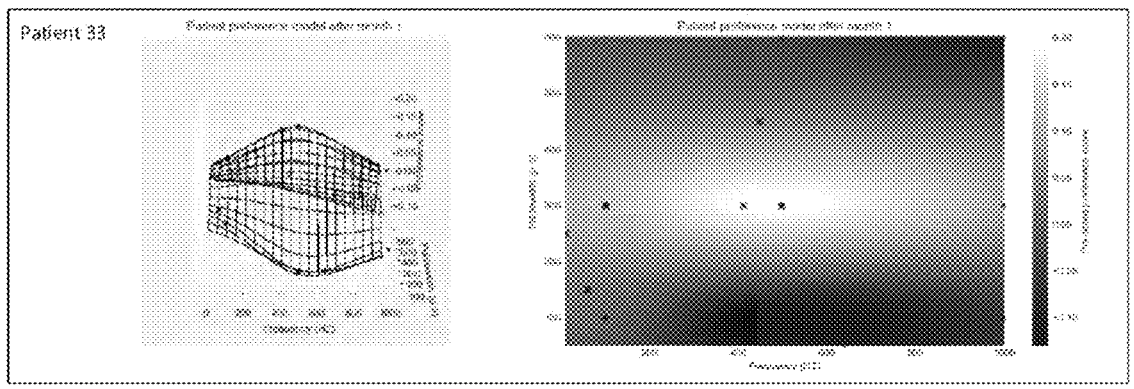
FIGS. 10A-10K depict a process for optimizing neurostimulation settings for a ninth example patient.
Figure 10B:
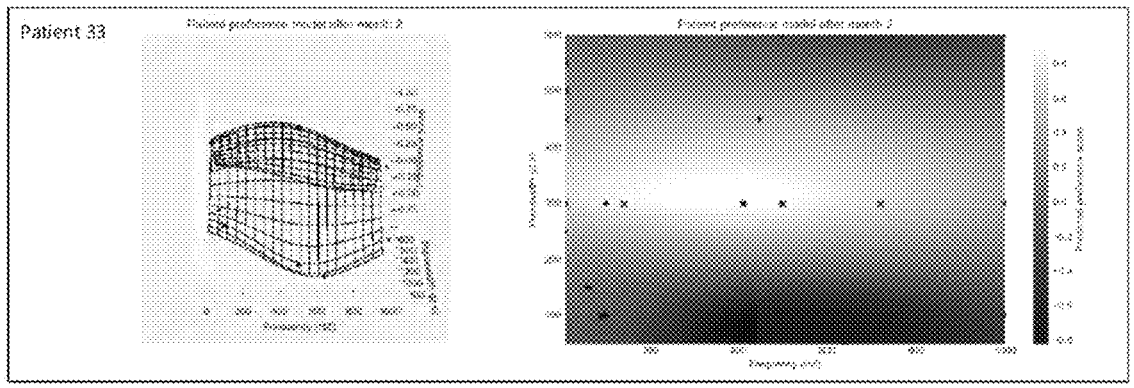
Figure 10C:
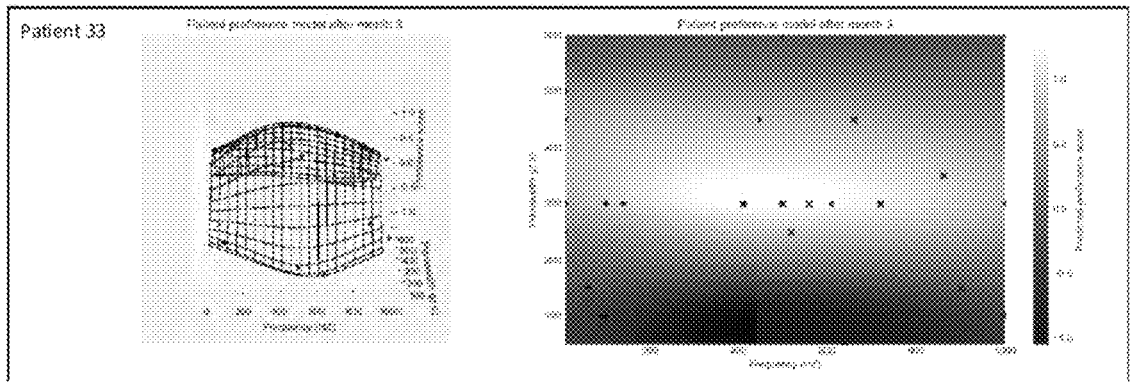
Figure 10D:
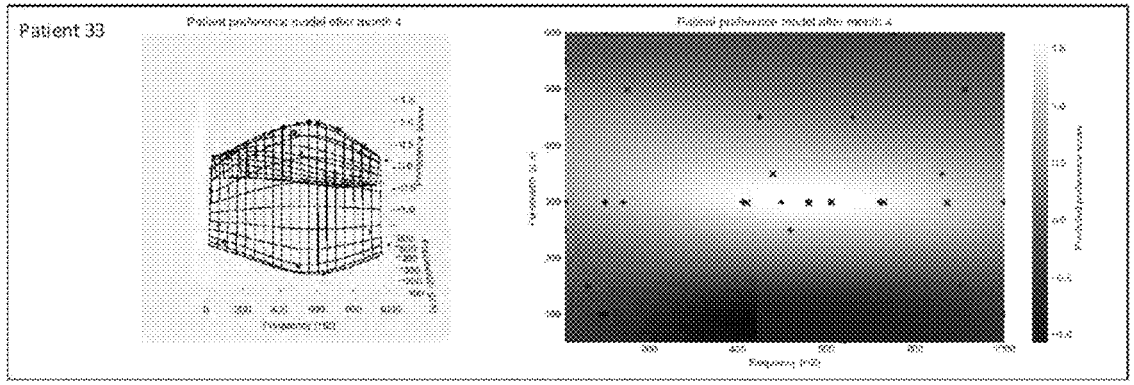
Figure 10E:
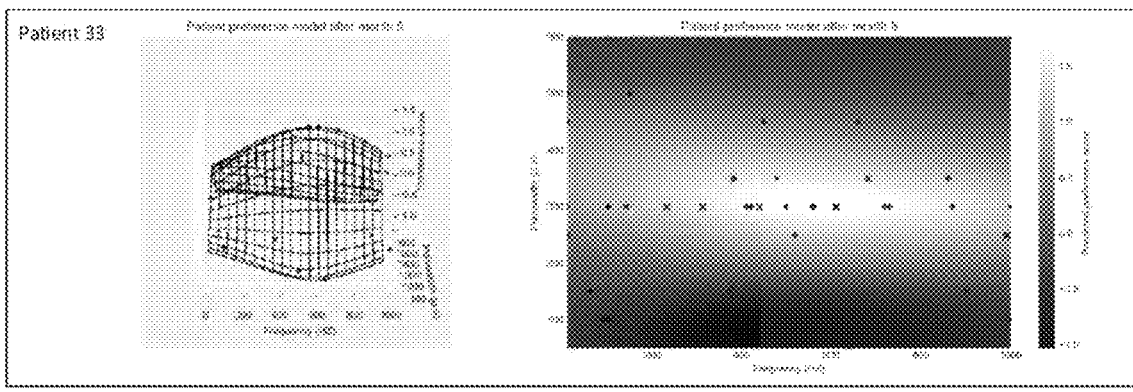
Figure 10F:
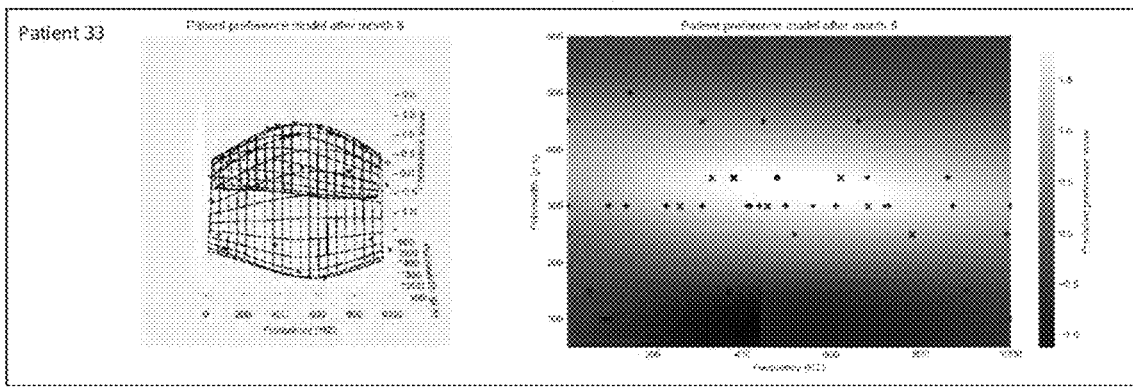
Figure 10G:
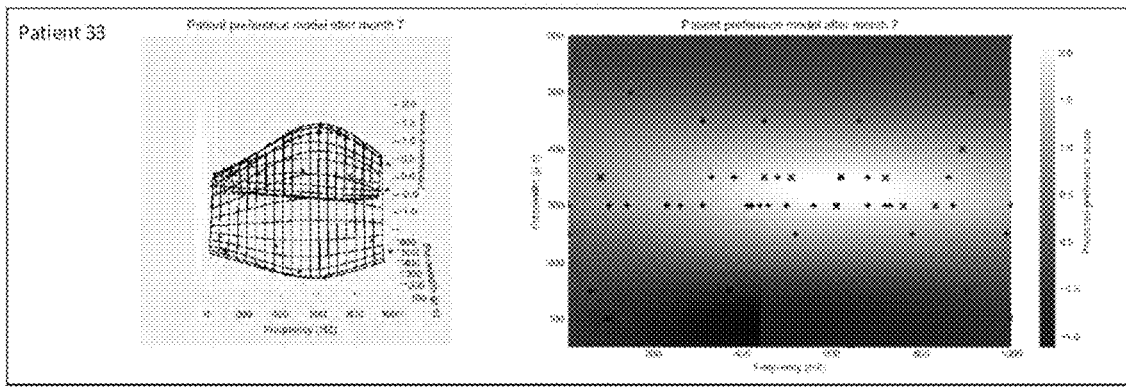
Figure 10H:
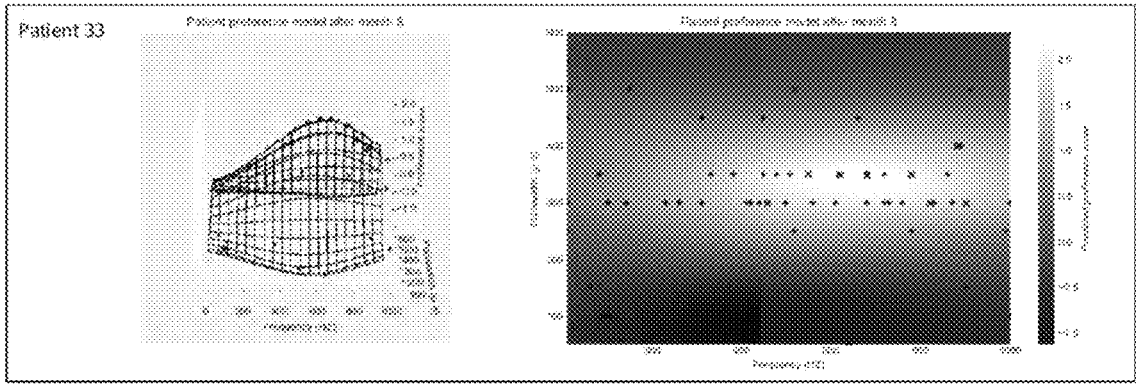
Figure 10I:
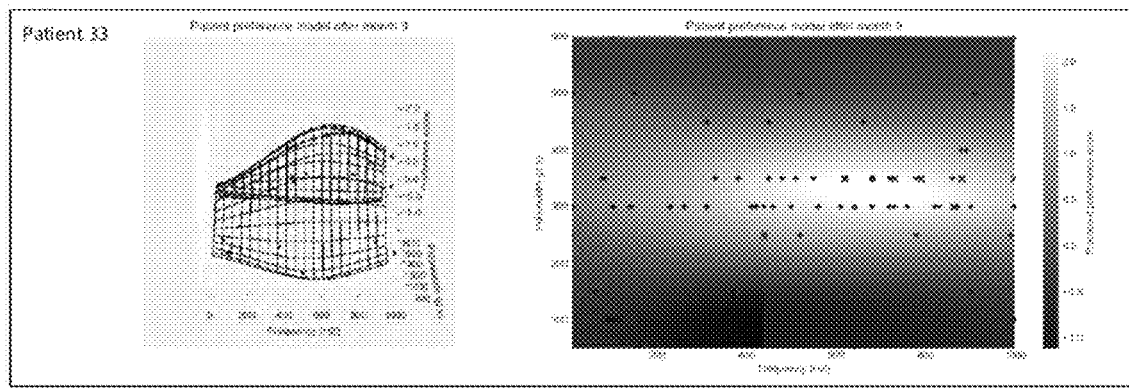
Figure 10J:
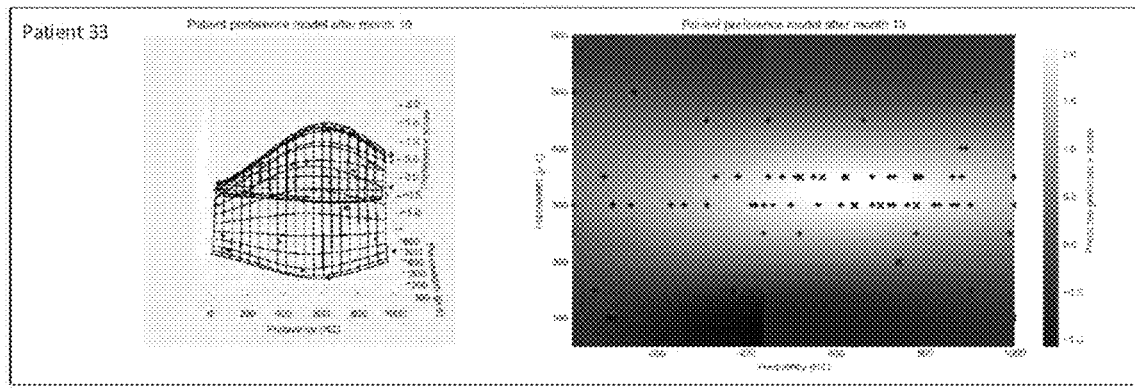
Figure 10K:
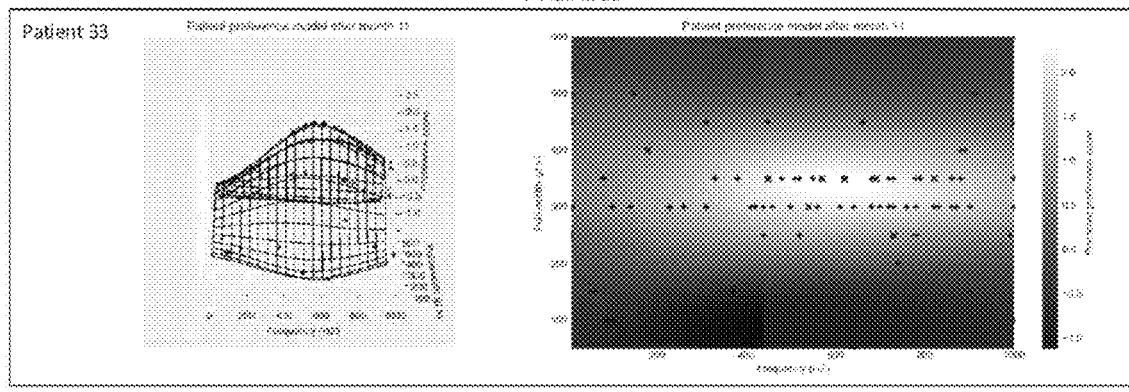

This process is repeated for successive months—FIG. 2D depicts test settings through month four, and a probit-generated preference score surface following receipt of preference data through the end of month four; FIG. 2E depicts the same through five months of testing; and so on.

Eleven months of optimization based on identification of new test settings and preference data received from the patient in response to those test settings are depicted in FIGS. 2A-2K. As is apparent in the preference score surfaces on the left of each of these figures and the corresponding grayscale heatmap depicting those corresponding preference score surfaces, for the example of FIGS. 2A-2K, the greatest changes in the preference score surface occur within the first six months; changes appear less significant in months seven through eleven.

FIGS. 4A-10K depict similar example optimization processes for eight additional simulated patients. As depicted, the results are similar as with the first example patient—namely, significant converge generally occurs within the first six months, with less significant refinement coming in the latter months.

Optimization processes are depicted for nine example patients in FIGS. 2A-10K. In many implementations, the method 100 (referring to FIG. 1) would be performed with a greater number of patients (e.g., 50, 100, 500, 1000, etc.). That process for nine example patients is illustrated and described herein to illustrate specific aspects of the example method 100—the next aspect of which is, with reference to FIG. 1, deriving a set of surface-characterizing points for each patient in the first population, as indicated at step 104.

Figure 11:
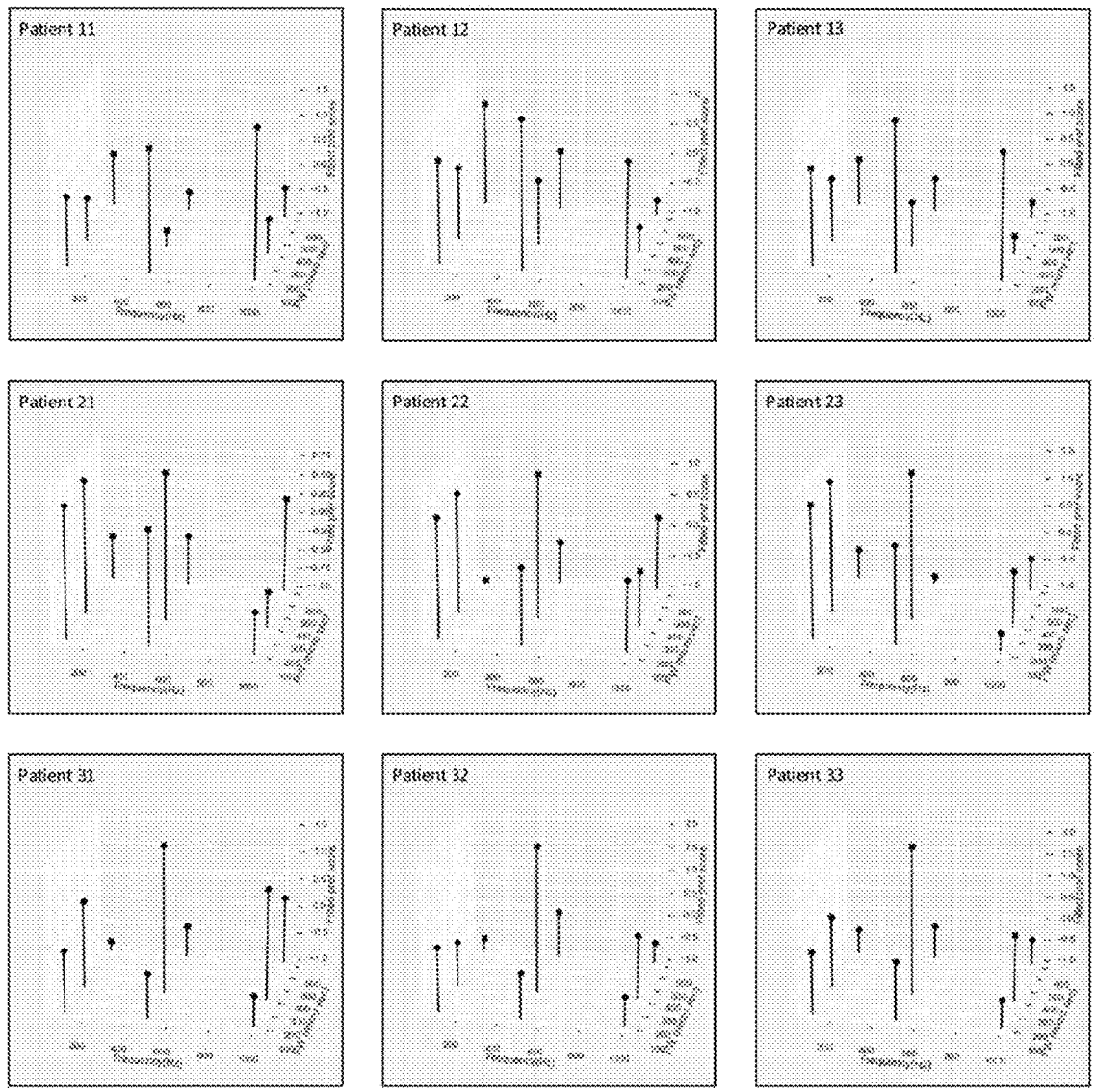
FIG. 11 illustrates the final preference score surfaces for each of the nine example patients whose optimization process was depicted in FIGS. 2A-10K.

Once neurostimulation settings have been optimized (e.g., at step 102 in FIG. 1) for each patient within a first population of patients, the final optimized settings can be analyzed. Specifically, a finite set of points that characterize the preference score surface for each patient can be derived, as shown at step 104 of FIG. 1. FIG. 11 illustrates the final preference score surfaces for each of the nine example patients whose optimization process was depicted in FIGS. 2A-10K. In FIG. 11, the final settings for each patient are depicted using a "ball-and-stick" representation to show the three-dimensional nature of the settings (e.g., the x-axis corresponding to frequency, the y-axis corresponding to pulse width, and the z-axis corresponding to the preference score).

In FIG. 11, the specific points that characterize each preference score surface have been selected to be the same points for each patient in the first population, to simplify visual comparison across patients. Specifically, in the example depicted, the points have been selected at the following pulse-width/frequency pairs {(100 uS, 150 Hz), (300 uS, 150 Hz), (600 uS, 150 Hz), (100 uS, 500 Hz), (300 uS, 500 Hz), (600 uS, 500 Hz), (100 uS, 1000 Hz), (300 uS, 1000 Hz), (600 uS, 1000 Hz)}.

Referring back to FIG. 1, once a set of surface-characterizing points have been derived at step 104, those surface-defining points can be compared to extract n clusters, as indicated at step 106. The number n can be selected to balance computational overhead (both in the extraction step and in the subsequent steps) against precision and speed of convergence.

In some implementations, comparing the surface-defining points can include calculating distances of each value relative to other values for each given surface-characterizing point, and these distances can be aggregated across all surface-characterizing points. For example, an aggregate calculation of distances of each value for Patient 11 can be calculated (at each surface-characterizing point-100 Hz/100 uS, 100 Hz/300 uS, 100 Hz/600 uS, 500 Hz/100 uS, etc.) relative to the same values for, in the example described and depicted herein, Patient 12, Patient 13, Patient 21, Patient 22, Patient 23, Patient 31, Patient 32 and Patient 33. Individual aggregate distance values can then be grouped in clusters, where values in each cluster have minimal distances relative to values outside the clusters. Again, the number of clusters can be optimized based on a balancing of computational overhead and precision/speed of convergence.

The foregoing is merely an example and high-level qualitative description. It will be appreciated by those having ordinary skill in the art that there are numerous, known methods for identifying clusters within a dataset; this high-level description is not intended to be limiting. As a non-limiting example, artificial intelligence ("AI")-based clustering algorithms can alternatively be used to extract the clusters from the population-based optimized neurostimulation settings. These AI-based clustering algorithms may include machine learning-based clustering algorithms, including those based on artificial neural networks, k-means clustering, mean-shift clustering, and the like.

Figure 12A:
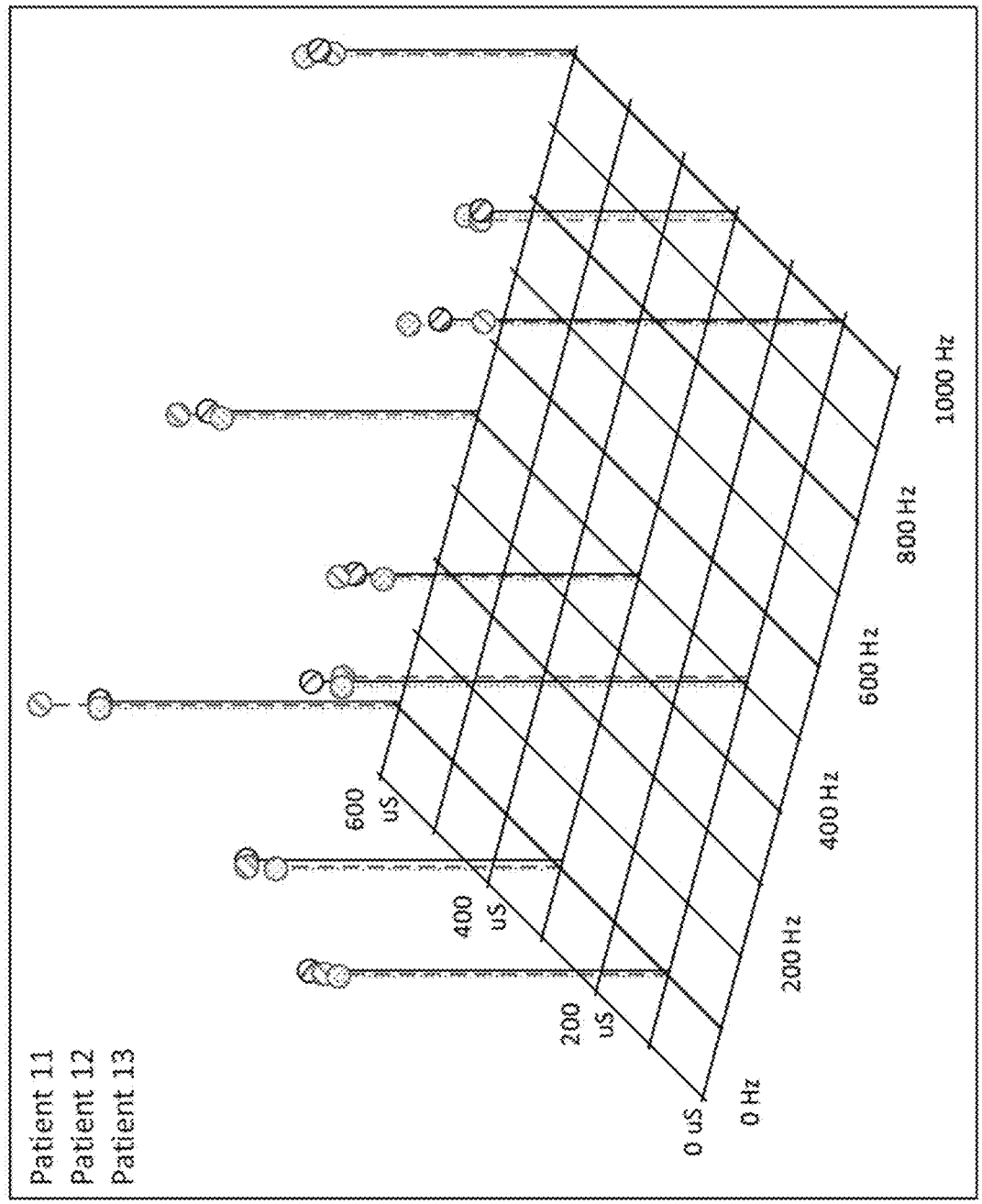
FIGS. 12A, 12B and 12C illustrate example clusters.
Figure 12B:
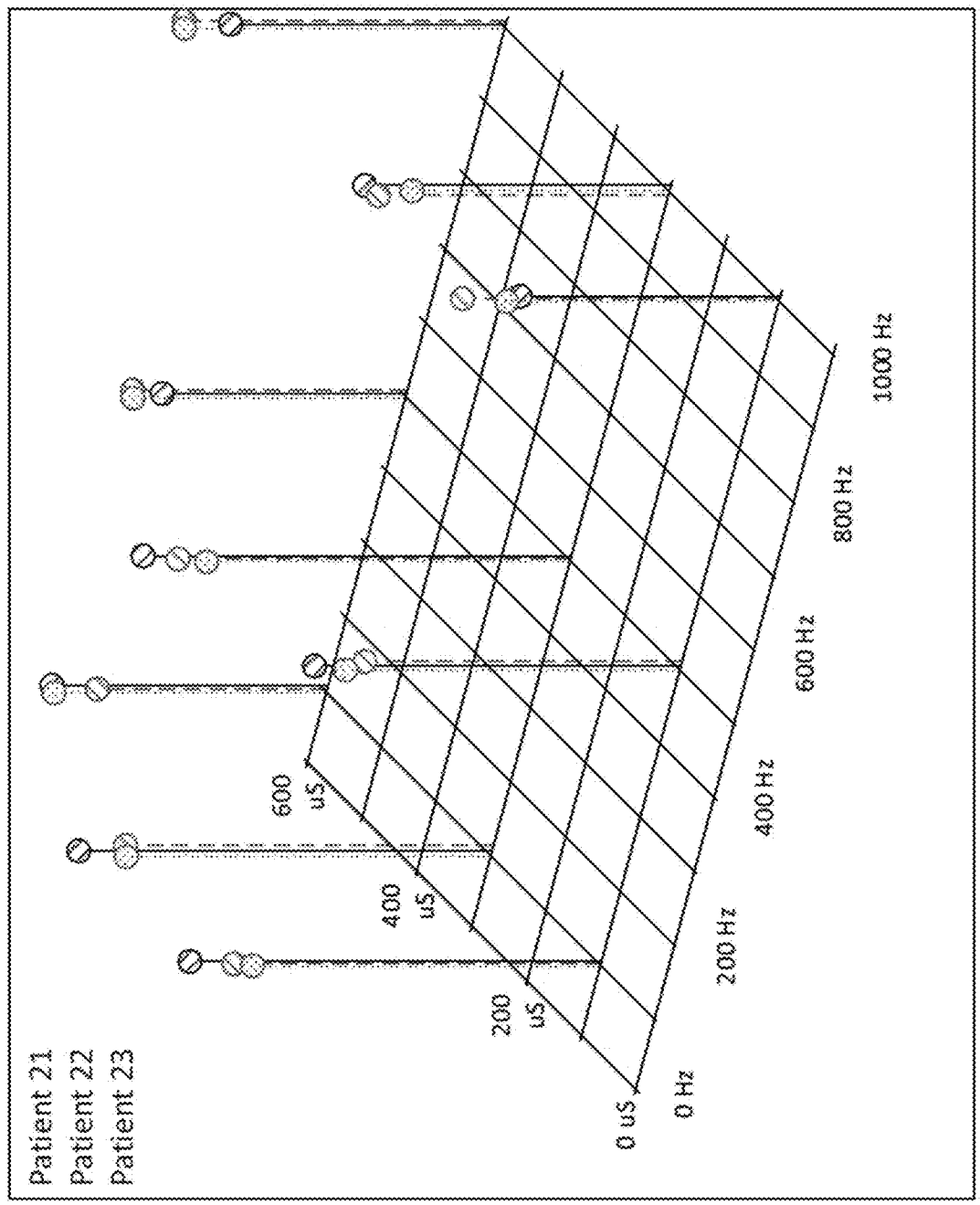
Figure 12C:
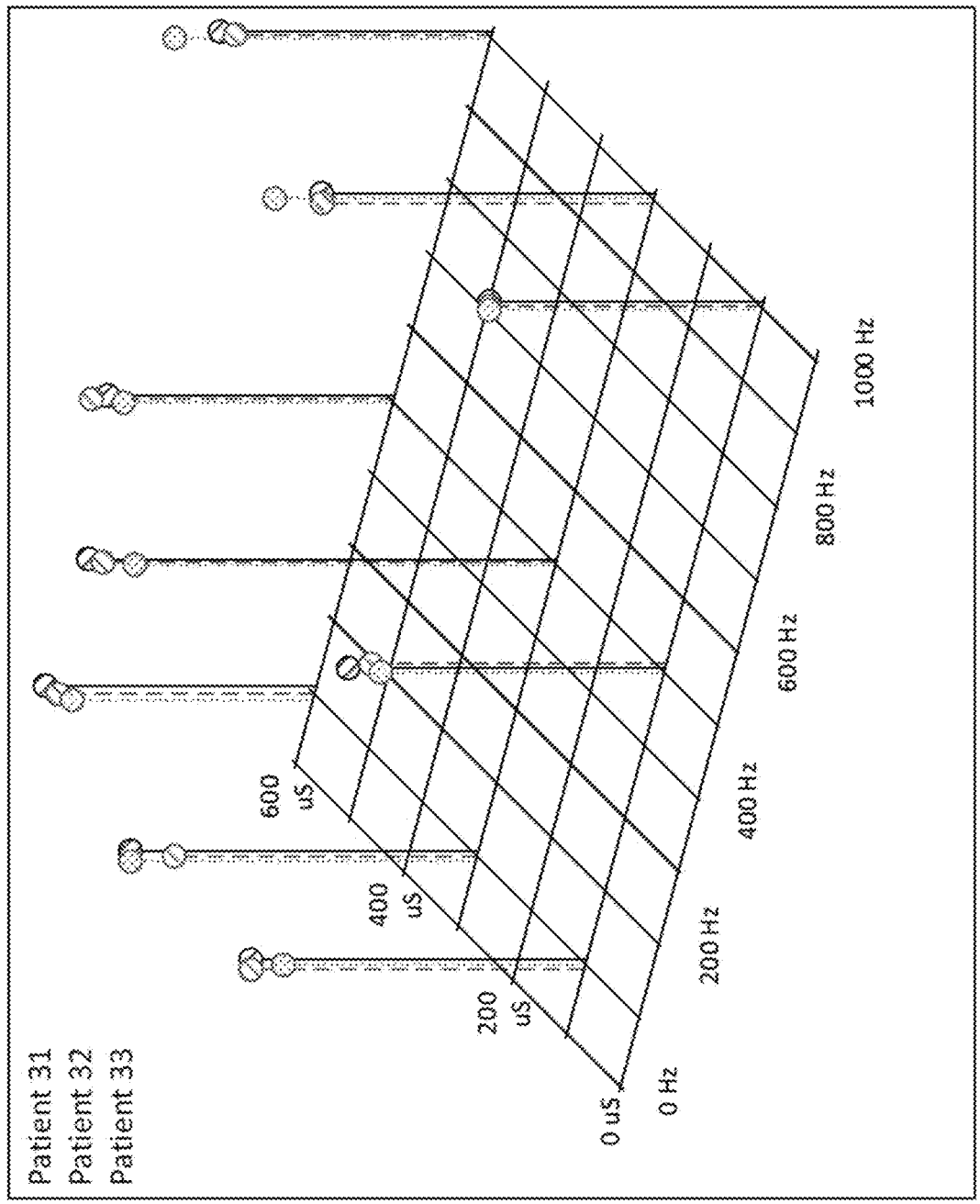

FIGS. 12A, 12B and 12C illustrate example clusters. As depicted, there are three clusters—which include Patient 11, Patient 12 and Patient 13 in the first cluster (see FIG. 12A); Patient 21, Patient 22 and Patient 23 in the second cluster (see FIG. 12B); and Patient 31, Patient 32 and Patient 33 in the third cluster (see FIG. 12C).

In some implementations, a larger number of clusters will be identified; and in other implementations, a smaller number of clusters will be identified. In some implementations, as depicted and described, clusters may be identified after a first population has been optimized and corresponding surface-characterizing data points have been identified. In other implementations, surface-characterizing data points and the clusters themselves may be identified and/or adjusted in real time, as optimization of a first patient population proceeds.

Once clusters have been identified, an average surface may be derived for each cluster, as indicated at step 108 of FIG. 1. While not explicitly illustrated in the figures, such a surface may correspond to a surface that best fits all of the data points in the cluster. With reference to FIGS. 12A, 12B and 12C, such a surface would fit the points at each surface-characterizing point (e.g., intersect, or closely intersect, the points at each surface-characterizing point).

Once average surfaces are derived, it is advantageous to identify a minimum number of test settings that can be presented to new patients to discriminate between the n clusters, as indicated at step 110 in FIG. 1. Settings that can efficiently discriminate between clusters can be identified by known brute-force distance calculation techniques. Qualitatively, such test settings may typically correspond to portions of the average surfaces of each cluster that are very different from each other. In cases where a subset of the surfaces overlap—such that one test setting my rule out one or more clusters but not precisely identify a single cluster—one or more subsequent test settings can be optimally chosen to efficiently identify a single cluster.

There are many brute-force and analytical methods to identify test settings to efficiently discriminate between clusters. What follows is a description of one example process. The example process is described in the context of treating chronic pain with neurostimulation by optimizing frequency and pulse width (amplitude could be optimized as well); but the example process is extendable to other conditions and parameters.

Figure 13A:
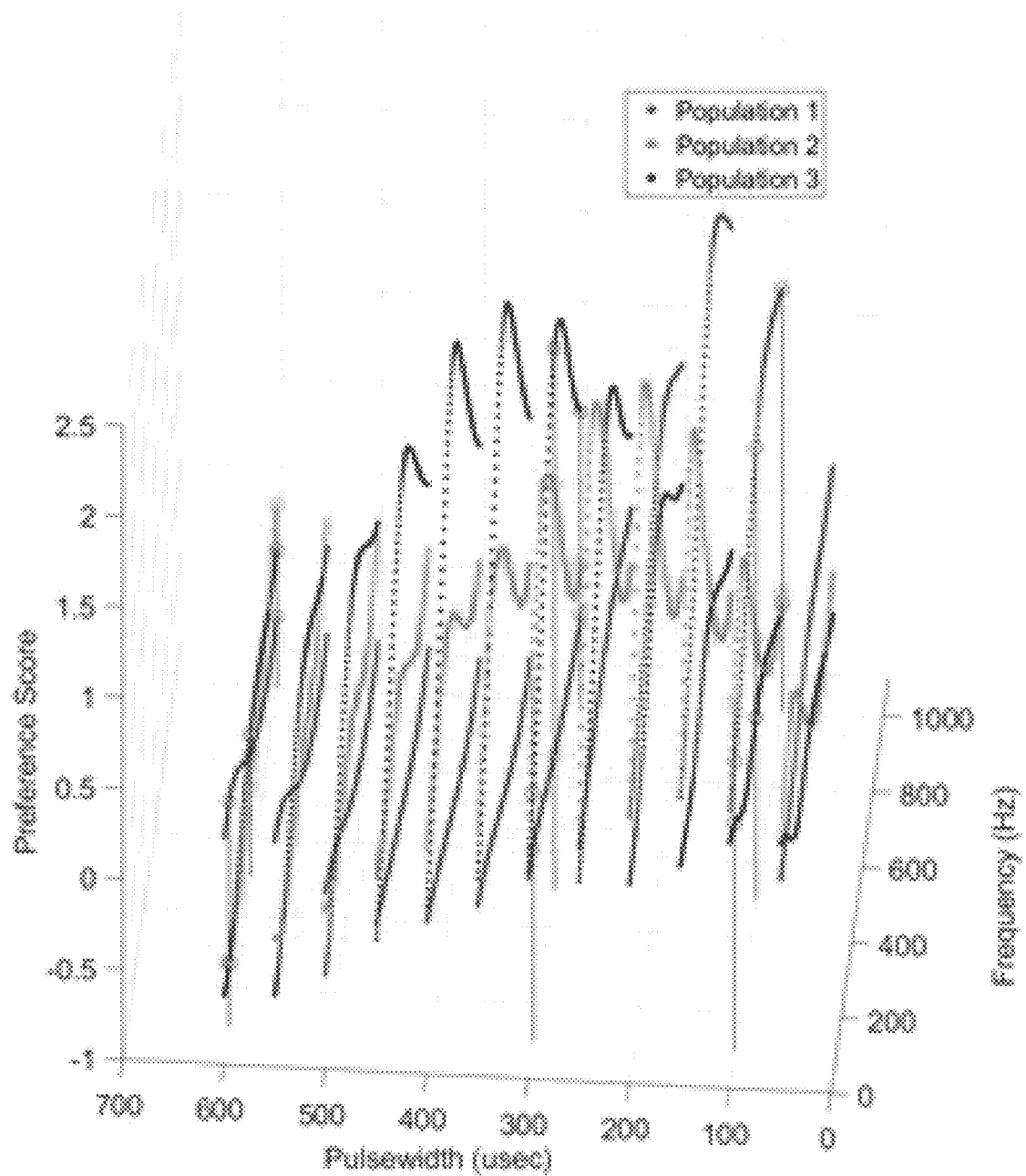
FIGS. 13A, 13B, 13C and 13D illustrate various aspects of an example method for determining test settings for discriminating between clusters.

Assume that for each setting there is a pain score: $P(s_i)$, at setting $s_i$. There are clusters $c_i$ in which the response to stimulation across settings is more similar than patient's response to stimulation from other clusters. The average pain score for patients for setting $s_i$ within a cluster $c_j$ will be identified as $P(s_i, c_j)$. Response surfaces from the three populations are shown in FIG. 13A, which depicts response surfaces from different patient populations who respond differently to stimulation settings. Stimulation settings, frequency and pulse width, are the x and y-axes, the preference score to the stimulation is the z-axis. The response surfaces for the three populations are shown in red, green, and blue. Nine settings represent samples from the populations, indicated by black lines that intercept the x-y plane and where they intersect the surfaces is represented as circles.

To identify settings that will be used to classify patients, the response for each stimulus setting can be treated as a vector of the responses for each cluster, $R(s_i)=[P(s_i,c_1),P(s_i,c_2), \ldots ,P(s_i,c_{Nclust})]$;

where Nclust is the number of available clusters that the patient could be a member of. The goal will be to select settings to test $T_i$ where i=1: Nset, where Nset is the number of settings that can be used for testing which will be used identify what cluster the patient is a member of.

Figure 13B:
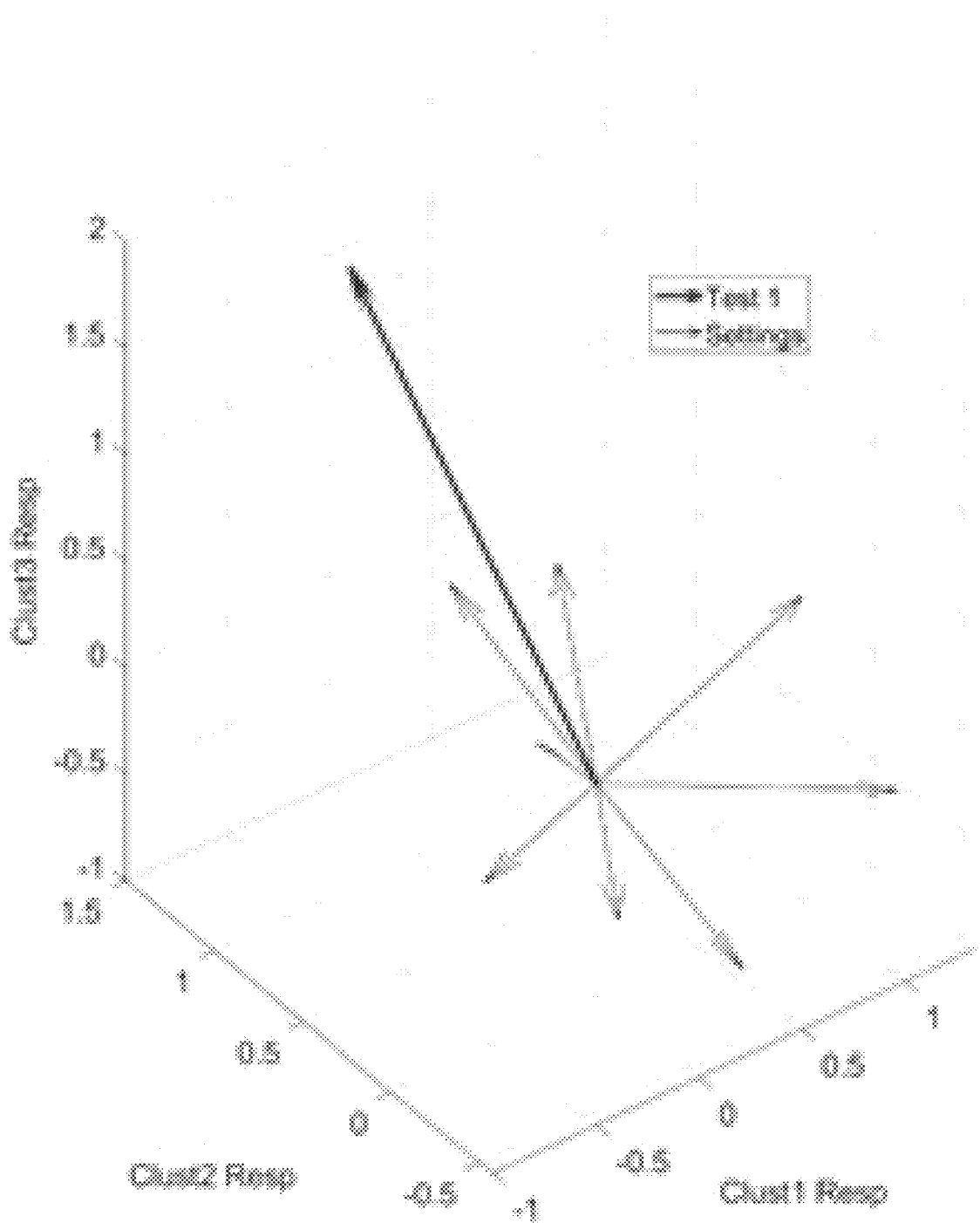

FIG. 13B illustrates the response space for the three clusters for each setting. The three axes represent the average stimulation value for each cluster. Each arrow represents a different stimulation setting. The goal is to identify stimulation settings that maximally differentiate the responses across the three population responses. The red vector represents the first test setting selected, which is the setting that has the greatest variance across the responses.

Selection of Setting 1: The first setting selected will be the one that has the greatest variability in the response across the clusters.

$$T_1 = \max_i \sum_j (P(s_i, c_j) - \bar{P}(c_j))^2$$

Where $\bar{P}(c_j)$ is the average response score (such as pain score or preference score) within cluster j. This first selected test setting is represented as the red vector in FIG. 13B.

Figure 13C:
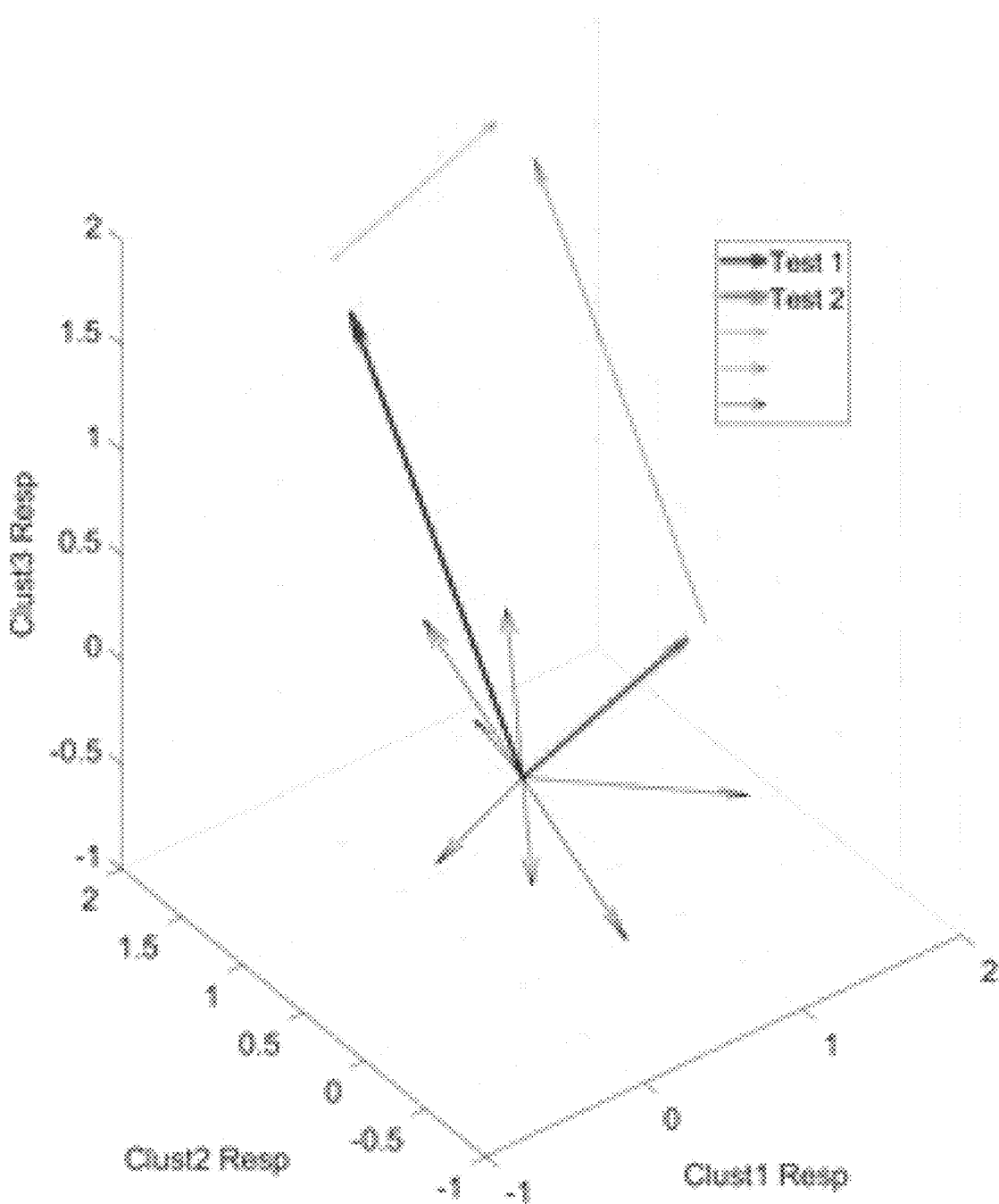

Selection of Setting 2: The goal of the subsequent settings are to find settings that are close to orthogonal to the previous settings to achieve settings responses that maximally differentiate the responses from the different clusters. Each response $R(s_i)$ represents a vector of responses across clusters to the same stimulus $s_i$. The response vector to the first test stimulus is $R(T_1)$. The goal of selecting the second test stimulus is to find a stimulus whose response vector is as close to orthogonal to the first vector as possible. This can be measured by maximizing the cross product between the first test point and the second test point's response:

$$T_2 = \max_i |R(T_1) \otimes R(s_i)|$$

Where $\otimes$ is the cross product between the two vectors and $\|\ \|$ is the norm of the resulting vector. FIG. 13C shows the vector with the greatest cross product to the first Test setting (T1). The cross product can be represented as the area of the parallelogram where the two edges are the vectors T1 and T2.

FIG. 13C depicts selection of the second test vector as the setting with the greatest cross product to the first test setting. The cross product between two vectors can graphically be represented as the area produced by the parallelogram created by the two vectors. This parallelogram is represented by the two vectors and their parallel vectors. By maximizing this area, we are maximizing the orthogonality and the length of the two vectors.

Figure 13D:
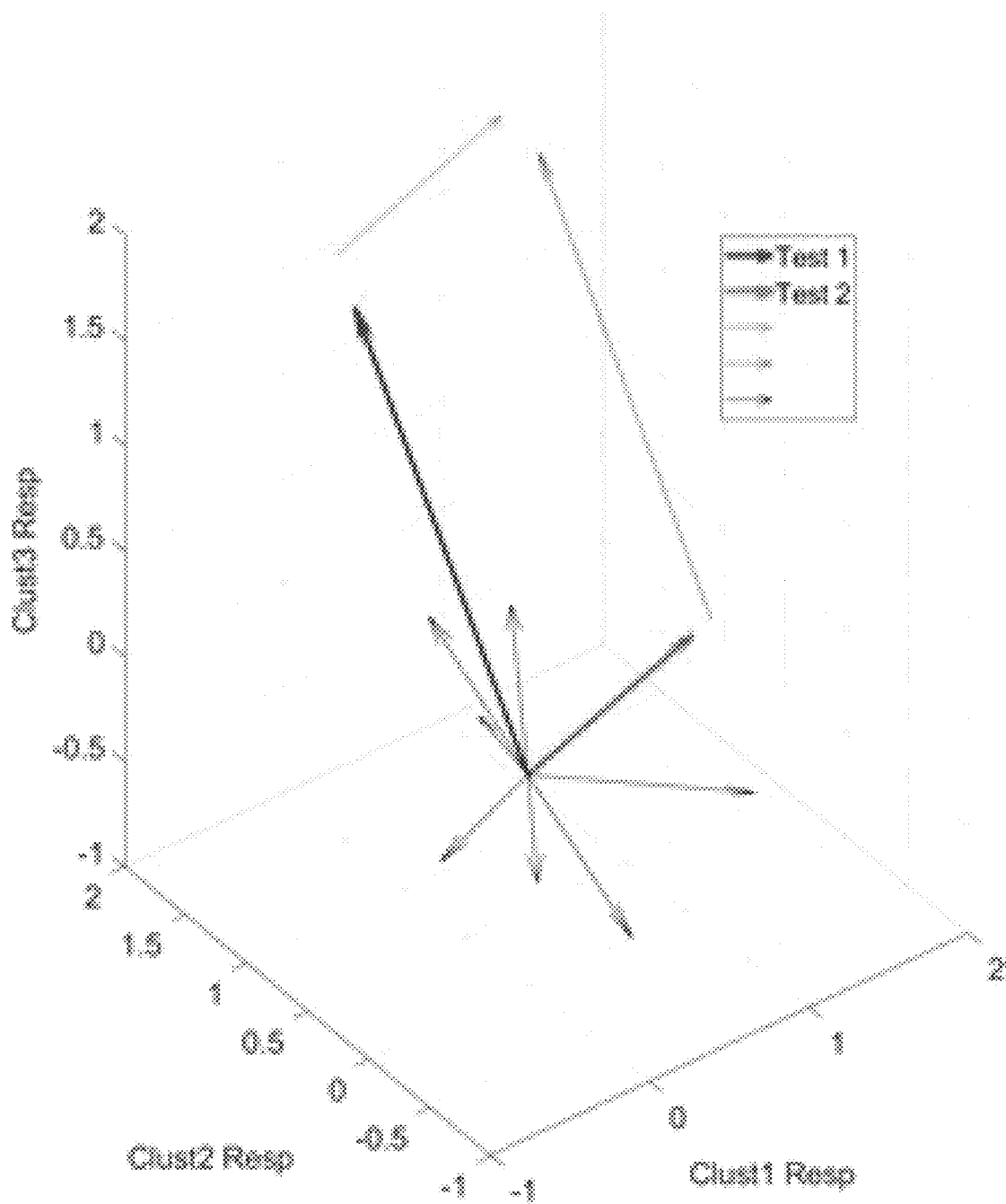

For the third setting, a setting that is close to orthogonal to the first two vectors and maximizes the parallelepiped between the three vectors is found by maximizing the following equation:

$$T_3 = \max_i R(s_i) \odot (R(T_1) \otimes R(T_2))$$

Where $\odot$ is the dot product between the response vector $R(s_i)$ and the cross product of $R(T_1)$ and $R(T_2)$. FIG. 13D shows the selected vector and the resulting parallelepiped generated by the three vectors. This results in selecting a setting that maximizes the volume of response space by selecting the three settings. FIG. 13D depicts selection of a third test setting. The selection of the third test setting maximizes the parallelepiped generated by the first three settings.

This approach can be used for three clusters. However, if there are more than three clusters, a generalization of the cross product may be used. The number of settings that can be selected this way is equal to the number of clusters. However, there may be opportunity, or necessity for redundancy and reliability to sample beyond the number of samples equal to the number of clusters. In this case, samples that maximize the convex hull of the response space can be selected. If the set of test settings response vectors already selected is defined as $\mathcal{T}_k=\{T_1, T_2, \ldots, T_k\}$, then the next test point can be selected as follows:

$$T_{k+1} = \max_i \|ConvHull(\{\mathcal{T}_k, s_i\})\|$$

where $\|ConvHull(\{\mathcal{T}_k,s_i\})\|$ is the volume of the convex hull created by the existing test settings and the addition of the setting response.

One alternative approach for selecting subsequent settings is to average test setting vectors together and continue using the same approach used in selecting the third setting:

$$\bar{R} = \sum_{i=1}^{k-2} R(T_i)$$

$$T_k = \max_i R(s_i) \odot \left(\bar{R} \otimes R(T_{k-1})\right)$$

Taking care to exclude settings in the maximization routine that have already been selected in the test set.

Once test settings (e.g., neurostimulation settings) have been determined at step 110 in FIG. 1 to efficiently discriminate between clusters, the test settings can be presented to each patient outside the first population (in the same manner that test settings are presented to patients in the first population for optimization), as indicated at step 112 of FIG. 1.

Provided the test settings are determined to efficiently discriminate between clusters, then a patient's preferences to the presented test settings can facilitate mapping of that patient to a specific cluster, as indicated at step 114 of FIG. 1. Qualitatively, the mapping process may involve application of known distance-calculating or line/surface-fitting algorithms, calculation of averages and standard deviations, identification of a highest correlation coefficient, etc.

In some implementations, a patient's response model may be built and similarity indices, such as a Pearson correlation coefficient or an earth mover distance, can be calculated to determine which cluster the patient likely belongs to. Statistical parameter estimation methods can also be used to estimate the likelihood of a patient belonging to any of the clusters. FIG. 14 depicts use of Pearson correlation coefficients to map the nine example patients into three clusters.

In some implementations, a patient is mapped to a cluster once, based on an initial set of test settings. In some implementations, such a mapping may be confirmed multiple times, based on preferences to test settings beyond the initial set; and the patient may be re-mapped to a different cluster if subsequent preference data indicates a remapping is appropriate.

Once a patient is mapped to a specific cluster, the average surface of that cluster can be leveraged to identify/filter new test settings, as indicated at step 116 of FIG. 1. In some implementations, maxima on the surface may be identified as new test settings. In some implementations, the Bayesian optimization process described above may be employed to identify multiple new test settings in the usual manner, but the average surface may be leveraged to filter in or out certain possible next test settings.

In some implementations, the identification of new settings and the number of settings needed may be dependent on how different each cluster is from the other clusters and how much noise is expected or present in patient feedback data.

In some implementation, the optimization process proceeds iteratively from here. That is, patient preference data is received from the last-presented test settings; a Bayesian optimization process, as described above, is performed to identify next settings at step 118 of FIG. 1, which are then again filtered at the repetition of step 116; or alternatively, the average surface of a mapped cluster is leveraged at the repetition of step 116 to identify new test settings.

This process can continue (e.g., the leveraging and optimizing steps) and until a satisfactory convergence between test settings and patient preference (e.g., until all, or a majority, of the test settings are highly preferred by a patient) has occurred.

In some implementations, application of the example method 100, depicted in FIG. 1, can result in faster convergence on preferred settings for particular patients than would otherwise occur (e.g., without use of clusters and corresponding average surfaces of those clusters).

Figure 15:
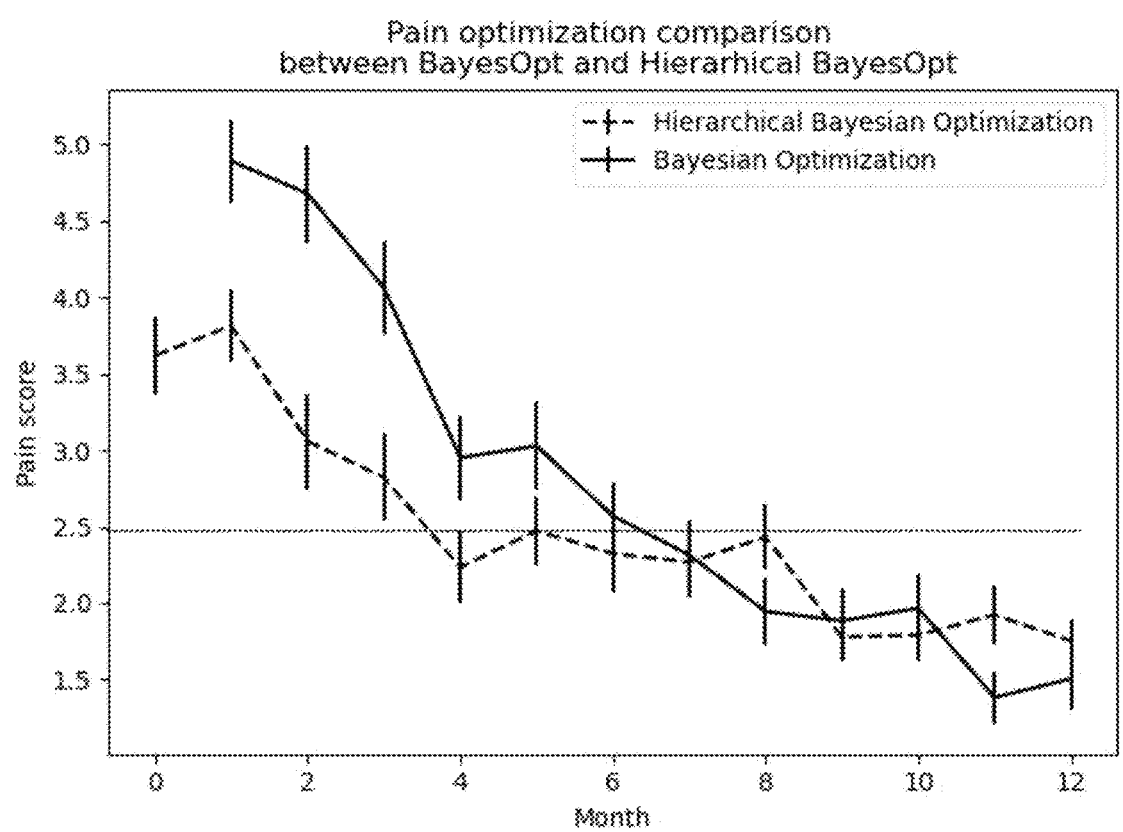
FIG. 15 depicts a simulated comparison between Bayesian optimization and hierarchical Bayesian optimization.

FIG. 15 depicts a simulated comparison between Bayesian optimization (without use of hierarchical, cluster-based optimization) and hierarchical Bayesian optimization. Specifically, the solid line plots the monthly average pain score and its standard error for nine synthetic patients (Patient 11, Patient 12, Patient 13, Patient 21, . . . ) from three clusters being optimized for 12 months using Bayesian optimization. The dashed line plots the monthly average pain score and its standard error for the same nine patients using the hierarchical Bayesian optimization. When using hierarchical optimization, one extra month is spent in the beginning to test settings to classify a patient into one of the three clusters. The settings tested in that month should be the ones that are informative to the classification.

As is shown in FIG. 15, the pain score drops to below 2.5 around month four using hierarchical Bayesian optimization; while this score does not drop below 2.5 until around month six using standard Bayesian optimization. Such an accelerated convergence can be very advantageous to patients.

The data presented here is simulated for just nine patients. With a greater number of patients, convergence may be even faster, depending on how representative individual clusters are of classes of actual patients having specific conditions and preferred responses to neurostimulation settings. The closer the correlation is between patients within a class and a cluster representing that class, the faster the convergence is expected; and that correlation is expected to improve as the volume of patient data grows (e.g., as the number of patients grows) and based on the parameters of the clusters (e.g., numbers of clusters, nuanced differences between the clusters, ability to efficiently discriminate between clusters).

Figure 17:
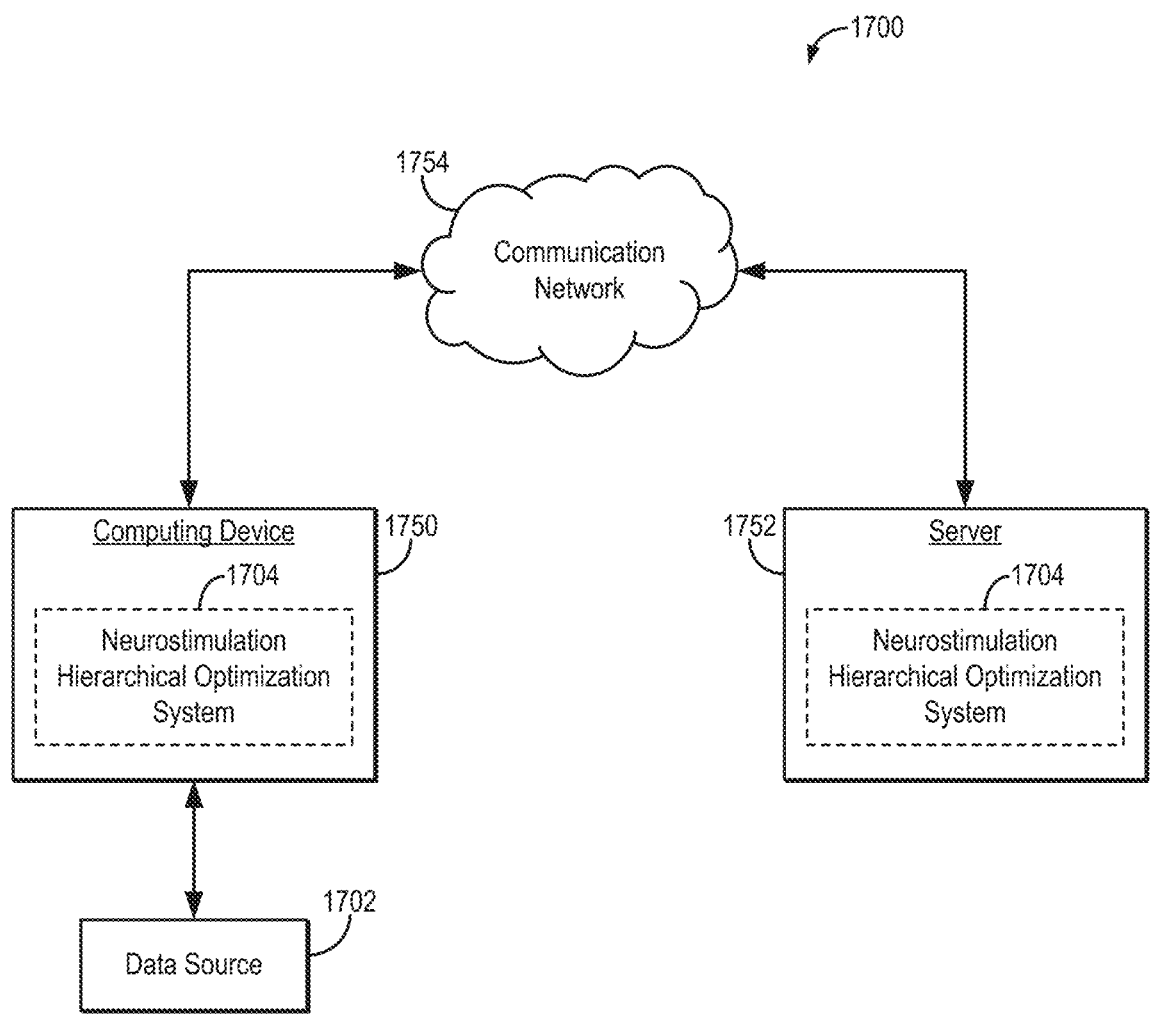
FIG. 17 is a block diagram of an example system that can implement the methods described in the present disclosure for determining user-based neurostimulation settings and/or for controlling the operation of a neurostimulation device based on those settings.

FIG. 17 illustrates an example of a system 1700 for hierarchical optimization of neurostimulation settings, or other controllable medical device settings, in accordance with some embodiments of the systems and methods described in the present disclosure. As shown in FIG. 17, a computing device 1750 can receive one or more types of data (e.g., neurostimulation settings from a first population of patients, user preference data) from data source 1702. In some embodiments, computing device 1750 can execute at least a portion of a neurostimulation hierarchical optimization system 1704 to optimization settings and/or control parameters for controlling a controllable medical device, such as a neurostimulator or other neuromodulator, from data received from the data source 1702.

Additionally or alternatively, in some embodiments, the computing device 1750 can communicate information about data received from the data source 1702 to a server 1752 over a communication network 1754, which can execute at least a portion of the neurostimulation hierarchical optimization system 1704. In such embodiments, the server 1752 can return information to the computing device 1750 (and/or any other suitable computing device) indicative of an output of the neurostimulation hierarchical optimization system 1704.

In some embodiments, computing device 1750 and/or server 1752 can be any suitable computing device or combination of devices, such as a desktop computer, a laptop computer, a smartphone, a tablet computer, a wearable computer, a server computer, a virtual machine being executed by a physical computing device, and so on. The computing device 1750 and/or server 1752 can also reconstruct images from the data.

In some embodiments, data source 1702 can be any suitable source of data (e.g., measurement data, neurostimulation settings from a first population of patients, user preference data), such as a controllable medical device (e.g., a neurostimulator or other neuromodulator), another computing device (e.g., a server storing measurement data, neurostimulation settings from a first population of patients, user preference data), and so on. In some embodiments, data source 1702 can be local to computing device 1750. For example, data source 1702 can be incorporated with computing device 1750 (e.g., computing device 1750 can be configured as part of a device for measuring, recording, estimating, acquiring, or otherwise collecting or storing data). As another example, data source 1702 can be connected to computing device 1750 by a cable, a direct wireless link, and so on. Additionally or alternatively, in some embodiments, data source 1702 can be located locally and/or remotely from computing device 1750, and can communicate data to computing device 1750 (and/or server 1752) via a communication network (e.g., communication network 1754).

In some embodiments, communication network 1754 can be any suitable communication network or combination of communication networks. For example, communication network 1754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), other types of wireless network, a wired network, and so on. In some embodiments, communication network 1754 can be a local area network, a wide area network, a public network (e.g., the Internet), a private or semi-private network (e.g., a corporate or university intranet), any other suitable type of network, or any suitable combination of networks. Communications links shown in FIG. 17 can each be any suitable communications link or combination of communications links, such as wired links, fiber optic links, Wi-Fi links, Bluetooth links, cellular links, and so on.

Figure 18:
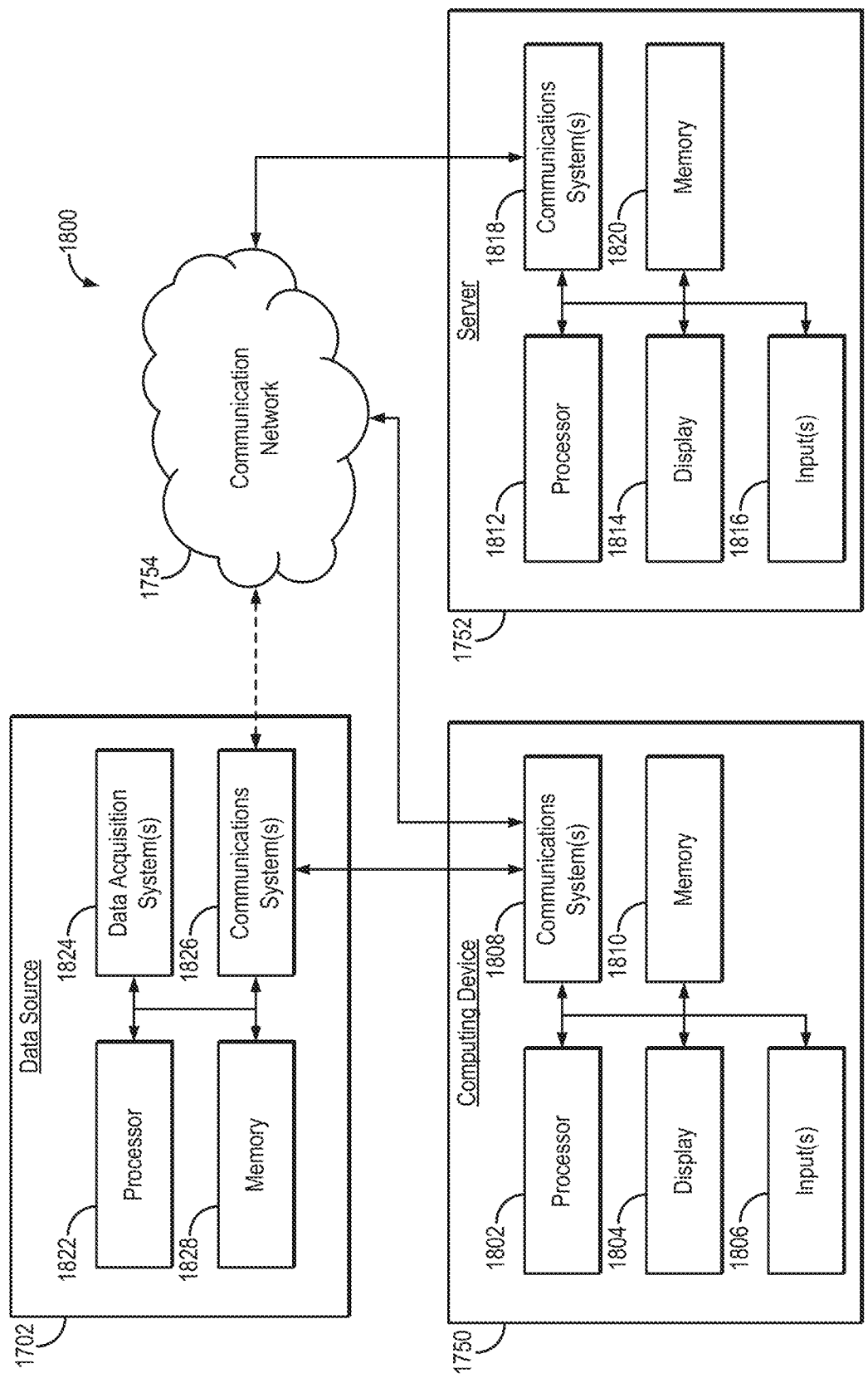
FIG. 18 is a block diagram of example components that can implement the system of FIG. 17.

Referring now to FIG. 18, an example of hardware 1800 that can be used to implement data source 1702, computing device 1750, and server 1752 in accordance with some embodiments of the systems and methods described in the present disclosure is shown.

As shown in FIG. 18, in some embodiments, computing device 1750 can include a processor 1802, a display 1804, one or more inputs 1806, one or more communication systems 1808, and/or memory 1810. In some embodiments, processor 1802 can be any suitable hardware processor or combination of processors, such as a central processing unit ("CPU"), a graphics processing unit ("GPU"), and so on. In some embodiments, display 1804 can include any suitable display devices, such as a liquid crystal display ("LCD") screen, a light-emitting diode ("LED") display, an organic LED ("OLED") display, an electrophoretic display (e.g., an "e-ink" display), a computer monitor, a touchscreen, a television, and so on. In some embodiments, inputs 1806 can include any suitable input devices and/or sensors that can be used to receive user input, such as a keyboard, a mouse, a touchscreen, a microphone, and so on.

In some embodiments, communications systems 1808 can include any suitable hardware, firmware, and/or software for communicating information over communication network 1754 and/or any other suitable communication networks. For example, communications systems 1808 can include one or more transceivers, one or more communication chips and/or chip sets, and so on. In a more particular example, communications systems 1808 can include hardware, firmware, and/or software that can be used to establish a Wi-Fi connection, a Bluetooth connection, a cellular connection, an Ethernet connection, and so on.

In some embodiments, memory 1810 can include any suitable storage device or devices that can be used to store instructions, values, data, or the like, that can be used, for example, by processor 1802 to present content using display 1804, to communicate with server 1752 via communications system(s) 1808, and so on. Memory 1810 can include any suitable volatile memory, non-volatile memory, storage, or any suitable combination thereof. For example, memory 1810 can include random-access memory ("RAM"), read-only memory ("ROM"), electrically programmable ROM ("EPROM"), electrically erasable ROM ("EEPROM"), other forms of volatile memory, other forms of non-volatile memory, one or more forms of semi-volatile memory, one or more flash drives, one or more hard disks, one or more solid state drives, one or more optical drives, and so on. In some embodiments, memory 1810 can have encoded thereon, or otherwise stored therein, a computer program for controlling operation of computing device 1750. In such embodiments, processor 1802 can execute at least a portion of the computer program to present content (e.g., images, user interfaces, graphics, tables), receive content from server 1752, transmit information to server 1752, and so on. For example, the processor 1802 and the memory 1810 can be configured to perform the methods described herein (e.g., the method 100 of FIG. 1).

In some embodiments, server 1752 can include a processor 1812, a display 1814, one or more inputs 1816, one or more communications systems 1818, and/or memory 1820. In some embodiments, processor 1812 can be any suitable hardware processor or combination of processors, such as a CPU, a GPU, and so on. In some embodiments, display 1814 can include any suitable display devices, such as an LCD screen, LED display, OLED display, electrophoretic display, a computer monitor, a touchscreen, a television, and so on. In some embodiments, inputs 1816 can include any suitable input devices and/or sensors that can be used to receive user input, such as a keyboard, a mouse, a touchscreen, a microphone, and so on.

In some embodiments, communications systems 1818 can include any suitable hardware, firmware, and/or software for communicating information over communication network 1754 and/or any other suitable communication networks. For example, communications systems 1818 can include one or more transceivers, one or more communication chips and/or chip sets, and so on. In a more particular example, communications systems 1818 can include hardware, firmware, and/or software that can be used to establish a Wi-Fi connection, a Bluetooth connection, a cellular connection, an Ethernet connection, and so on.

In some embodiments, memory 1820 can include any suitable storage device or devices that can be used to store instructions, values, data, or the like, that can be used, for example, by processor 1812 to present content using display 1814, to communicate with one or more computing devices 1750, and so on. Memory 1820 can include any suitable volatile memory, non-volatile memory, storage, or any suitable combination thereof. For example, memory 1820 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some embodiments, memory 1820 can have encoded thereon a server program for controlling operation of server 1752. In such embodiments, processor 1812 can execute at least a portion of the server program to transmit information and/or content (e.g., data, images, a user interface) to one or more computing devices 1750, receive information and/or content from one or more computing devices 1750, receive instructions from one or more devices (e.g., a personal computer, a laptop computer, a tablet computer, a smartphone), and so on.

In some embodiments, the server 1752 is configured to perform the methods described in the present disclosure. For example, the processor 1812 and memory 1820 can be configured to perform the methods described herein (e.g., the method 100 of FIG. 1).

In some embodiments, data source 1702 can include a processor 1822, one or more data acquisition systems 1824, one or more communications systems 1826, and/or memory 1828. In some embodiments, processor 1822 can be any suitable hardware processor or combination of processors, such as a CPU, a GPU, and so on. In some embodiments, the one or more data acquisition systems 1824 are generally configured to acquire data and can include electrophysiological sensors (e.g., electrodes), a user interface (e.g., to collect user feedback and preference data), which may include a graphical user interface, and so on. Additionally or alternatively, in some embodiments, the one or more data acquisition systems 1824 can include any suitable hardware, firmware, and/or software for coupling to and/or controlling operations of the controllable medical device (e.g., the neurostimulator or other neuromodulator). In some embodiments, one or more portions of the data acquisition system(s) 1824 can be removable and/or replaceable.

Note that, although not shown, data source 1702 can include any suitable inputs and/or outputs. For example, data source 1702 can include input devices and/or sensors that can be used to receive user input, such as a keyboard, a mouse, a touchscreen, a microphone, a trackpad, a trackball, and so on. As another example, data source 1702 can include any suitable display devices, such as an LCD screen, an LED display, an OLED display, an electrophoretic display, a computer monitor, a touchscreen, a television, etc., one or more speakers, and so on.

In some embodiments, communications systems 1826 can include any suitable hardware, firmware, and/or software for communicating information to computing device 1750 (and, in some embodiments, over communication network 1754 and/or any other suitable communication networks). For example, communications systems 1826 can include one or more transceivers, one or more communication chips and/or chip sets, and so on. In a more particular example, communications systems 1826 can include hardware, firmware, and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1828 can include any suitable storage device or devices that can be used to store instructions, values, data, or the like, that can be used, for example, by processor 1822 to control the one or more data acquisition systems 1824, and/or receive data from the one or more data acquisition systems 1824; to generate images from data; present content (e.g., data, images, a user interface) using a display; communicate with one or more computing devices 1750; and so on. Memory 1828 can include any suitable volatile memory, non-volatile memory, storage, or any suitable combination thereof. For example, memory 1828 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some embodiments, memory 1828 can have encoded thereon, or otherwise stored therein, a program for controlling operation of data source 1702. In such embodiments, processor 1822 can execute at least a portion of the program to generate images, transmit information and/or content (e.g., data, images, a user interface) to one or more computing devices 1750, receive information and/or content from one or more computing devices 1750, receive instructions from one or more devices (e.g., a personal computer, a laptop computer, a tablet computer, a smartphone, etc.), and so on.

Figure 19:
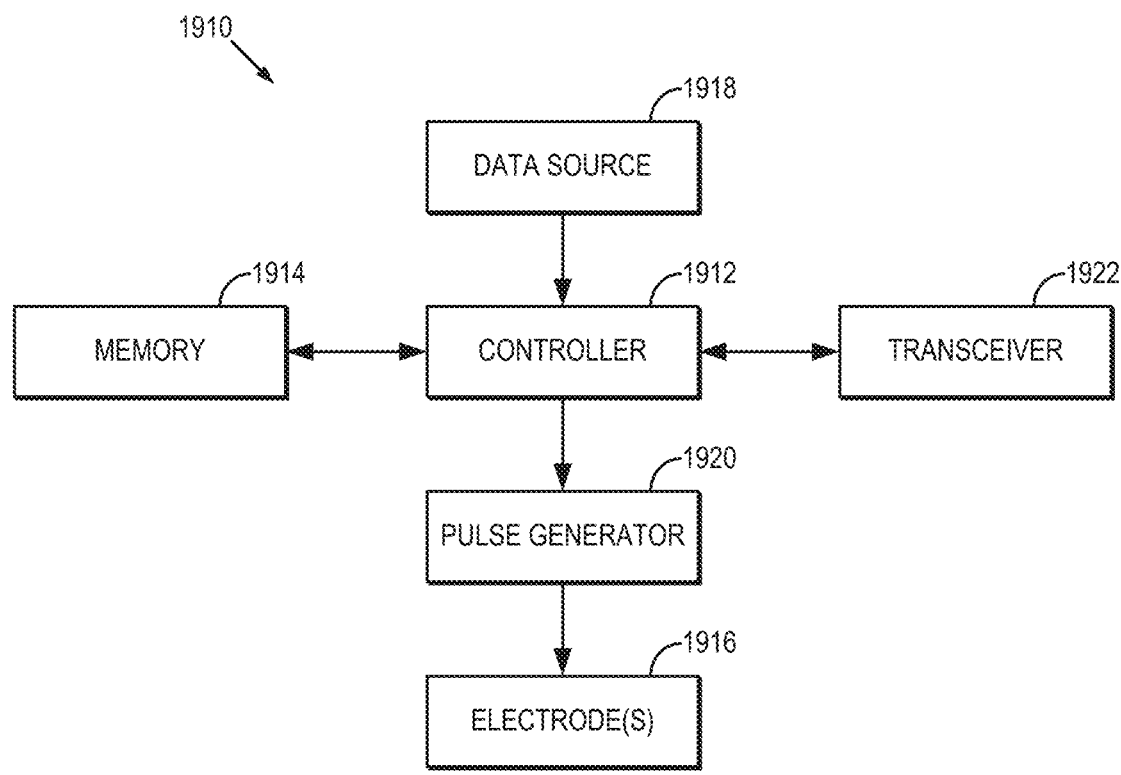
FIG. 19 is a block diagram of an example neurostimulation system that can implement the methods described in the present disclosure.

Referring now to FIG. 19, an example neurostimulation system 1910 that can implement the methods described above is illustrated. In general, the neurostimulation system 1910 includes a controller 1912, a memory 1914, and at least one electrode 1916. The neurostimulation system 1910 can be implemented as an implantable medical device, such as an implanted brain stimulation system, and implanted spinal cord stimulation system, and so on.

In general, the at least one electrode 1916 is capable of delivering electrical stimulation. In some embodiments, the at least one electrode 1916 is capable of both sensing electrophysiological activity and delivering electrical stimulation. Thus, in these embodiments, the at least one electrode 1916 also forms at least one sensor. A data source 1918 provides data to the controller 1912. The data may include neurostimulation settings (e.g., population based settings, user-based settings), user feedback or preference data, and so on.

The controller 1912 includes a processor to execute instructions embedded in or otherwise stored on the memory 1914 to implement the methods described above. The memory 1914 can also store user preference data and other data for processing, as well as settings (e.g., stimulation parameters) to be provided to the controller 1912 for directing the at least one electrode 1916 to provide electrical stimulation to a subject.

At least one electrode 1916 operates under control of the controller 1912 to deliver electrical stimulations to the subject in response thereto. Processing circuitry in the controller 1912 detects and processes data received by the data source 1918 to determine the optimized stimulation parameters based on the methods and algorithms described above. The optimized stimulation parameters are provided as instructions to a pulse generator 1920, which in response to the instructions provides an electrical signal to the at least one electrode 1916 to deliver the electrical stimulations to the subject.

The neurostimulation system 1910 can also include a transceiver 1922 and associated circuitry for communicating with a programmer or other external or internal device. As one example, the transceiver 1922 can include a telemetry coil.

In operation, the neurostimulation system 1910 receives data from the data source 1918. These data are provided to the controller 1912 where they are processed. The controller 1912 analyzes the data and estimates therefrom optimal user-based neurostimulation parameters, as described above. The optimized user-based neurostimulation parameters are provided to the pulse generator 1920 to control the at least one electrode 1916 to generate electrical stimulation that will achieve the desired effect in the subject.

In some embodiments, any suitable computer-readable media can be used for storing instructions for performing the functions and/or processes described herein. For example, in some embodiments, computer-readable media can be transitory or non-transitory. For example, non-transitory computer-readable media can include media such as magnetic media (e.g., hard disks, floppy disks), optical media (e.g., compact discs, digital video discs, Blu-ray discs), semiconductor media (e.g., RAM, flash memory, EPROM, EEPROM), any suitable media that is not fleeting or devoid of any semblance of permanence during transmission, and/or any suitable tangible media. As another example, transitory computer-readable media can include signals on networks, in wires, conductors, optical fibers, circuits, or any suitable media that is fleeting and devoid of any semblance of permanence during transmission, and/or any suitable intangible media.

As used herein in the context of computer implementation, unless otherwise specified or limited, the terms "component," "system," "module," "framework," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

The present disclosure has described one or more preferred embodiments, and it should be appreciated that many equivalents, alternatives, variations, and modifications, aside from those expressly stated, are possible and within the scope of the invention.

The invention claimed is:

1. A method for generating neurostimulation control settings for controlling a neurostimulation system, the method comprising:
    (a) receiving, by a controller of the neurostimulation system, population-based optimized neurostimulation settings comprising neurostimulation settings corresponding to patients in a population of patients;
    (b) extracting, using the controller, a plurality of clusters of neurostimulation settings from the population-based optimized neurostimulation settings;
    (c) determining, by the controller, a set of test settings that efficiently discriminate between the plurality of clusters;
    (e) presenting the set of test settings to a user via the controller;
    (f) iteratively applying, via the controller to the neurostimulation system, each test setting in the set of test settings;
    (g) receiving, by the controller, user preference data indicative of the user's preference for settings within the set of test settings;
    (h) determining at least one user-based neurostimulation setting using the controller to map the user to one of the clusters in the plurality of clusters based on the user preference data;
    (i) storing the determined at least one user-based neurostimulation setting; and
    (j) controlling the neurostimulation system using the stored user-based neurostimulation settings.

2. The method of claim 1, wherein determining the at least one user-based neurostimulation setting comprises iteratively updating the at least one user-based neurostimulation setting.

3. The method of claim 2, wherein iteratively updating the at least one user-based neurostimulation setting comprises:
    generating, using the controller, an average surface for each cluster in the plurality of clusters, wherein each average surface corresponds to a surface that fits data points within each respective cluster; and
    in each of a plurality of iterations:
        identifying, by the controller, a new set of test settings based on the average surface corresponding to the cluster to which the user is mapped;
        presenting the new set of test settings to the user via the controller;
        iteratively applying, via the controller to the neurostimulation system, each test setting in the new set of test settings;
        receiving, by the controller, updated user preference data indicative of the user's preference for settings within the new set of test settings; and
        updating the at least one user-based neurostimulation setting based on the updated user preference data.

4. The method of claim 3, wherein the at least one user-based neurostimulation setting is updated based on a Bayesian optimization.

5. The method of claim 4, wherein the average surface is used to filter potential test settings in the new set of test settings.

6. The method of claim 3, wherein updating the at least one user-based neurostimulation setting includes generating a probit function from the user preference data and updating the at least one user-based neurostimulation setting using the probit function.

7. The method of claim 1, wherein extracting the plurality of clusters of neurostimulation settings from the population-based optimized neurostimulation settings comprises:
    extracting a set of surface-characterizing data points for each patient represented in the population-based optimized neurostimulation settings;
    comparing the surface-characterizing data points to each other in order to identify and extract the plurality of clusters.

8. The method of claim 7, wherein the surface-characterizing data points comprise a set of points that characterize a preference score surface for each patient.

9. The method of claim 7, wherein comparing the surface-characterizing data points to each other comprises calculating a distance metric between pairs of surface-characterizing data points.

10. The method of claim 9, wherein the plurality of clusters are identified and extracted by aggregating distance metrics across the set of surface-characterizing data points.

11. The method of claim 1, wherein determining the set of test settings that efficiently discriminate between the plurality of clusters comprises:
   determining a plurality of responses across the population-based optimized neurostimulation settings; and
   identifying as the set of test settings, neurostimulation settings that maximally differentiate responses across the plurality of responses.

12. The method of claim 1, wherein determining the at least one user-based neurostimulation setting comprises mapping the user preference data to one of the clusters in the plurality of clusters.

13. The method of claim 12, wherein mapping the user preference data to one of the clusters in the plurality of clusters is based on a distance metric.

14. The method of claim 12, wherein mapping the user preference data to one of the clusters in the plurality of clusters is based on one of a line fitting algorithm or a surface fitting algorithm.

15. The method of claim 12, wherein mapping the user preference data to one of the clusters in the plurality of clusters comprises:
   constructing a response model from the user preference data;
   calculating similarity indices based on the response model and the plurality of clusters; and
   mapping the user preference data to the one of the clusters in the plurality of clusters based on the similarity indices.

16. The method of claim 1, wherein the user comprises one of a subject within whom the neurostimulation system is implanted or a medical provider associated with a subject within whom the neurostimulation system is implanted.

17. A method for controlling a neurostimulation system implanted in a human user, the method comprising:
   (a) accessing via a controller of the neurostimulation system, population-based optimized neurostimulation settings comprising neurostimulation settings ranked according to preference by patients in a population of patients;
   (b) extracting for each patient represented in the population-based optimized neurostimulation settings, using the controller, a set of surface-characterizing data points that characterize a preference score surface for each patient;
   (c) extracting, using the controller, a plurality of clusters of neurostimulation settings from the population-based optimized neurostimulation settings using the set of surface-characterizing data points for each patient;
   (d) generating, via the controller, an average surface for each of the plurality of clusters, each average surface corresponding to a surface that fits the surface-characterizing data points within each respective cluster;
   (e) determining, by the controller, a set of test settings that efficiently discriminate between the plurality of clusters;
   (f) presenting the set of test settings to the human user via the controller;
   (g) receiving, by the controller, user preference data indicative of the user's preference for settings within the set of test settings;
   (h) determining at least one user-based neurostimulation setting using the controller to map the user to one of the clusters in the plurality of clusters based on the user preference data;
   (i) iteratively updating the at least one user-based neurostimulation setting, using the controller, wherein the average surface associated with the one of the clusters in the plurality of clusters is used to at least one of identify new test settings in each iteration or filter new test settings in each iteration; and
   (j) controlling the neurostimulation system, via the controller, using the updated at least one user-based neurostimulation settings.

18. The method of claim 17, wherein iteratively updating the at least one user-based neurostimulation setting comprises optimizing the at least one user-based neurostimulation setting based on a Bayesian optimization.

19. The method of claim 17, wherein determining the set of test settings that efficiently discriminate between the plurality of clusters comprises:
   determining a plurality of responses across the population-based optimized neurostimulation settings; and
   identifying as the set of test settings, neurostimulation settings that maximally differentiate responses across the plurality of responses.

* * * * *